(12) United States Patent
Kamtekar et al.

(10) Patent No.: US 10,655,168 B2
(45) Date of Patent: May 19, 2020

(54) MODIFIED BIOTIN-BINDING PROTEINS FOR IMMOBILIZATION

(71) Applicant: Pacific Biosciences of California, Inc., Menlo Park, CA (US)

(72) Inventors: Satwik Kamtekar, Mountain View, CA (US); Lubomir Sebo, Hayward, CA (US); Leewin Chern, Fremont, CA (US); Thomas Linsky, Mountain View, CA (US); Jeremiah Hanes, Woodside, CA (US); Erik Miller, Berkeley, CA (US); Ying Yang, Fremont, CA (US); Stephen Yue, Eugene, OR (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 16/230,480

(22) Filed: Dec. 21, 2018

(65) Prior Publication Data

US 2019/0249237 A1    Aug. 15, 2019

Related U.S. Application Data

(60) Provisional application No. 62/609,680, filed on Dec. 22, 2017.

(51) Int. Cl.
    *C12Q 1/6848* (2018.01)
    *C12N 9/22* (2006.01)
    *C07K 14/36* (2006.01)

(52) U.S. Cl.
    CPC ............ *C12Q 1/6848* (2013.01); *C07K 14/36* (2013.01); *C12N 9/22* (2013.01)

(58) Field of Classification Search
    CPC ......... C12Q 1/6848; C12N 9/22; C07K 14/36
    See application file for complete search history.

(56) References Cited

U.S. PATENT DOCUMENTS

| | | |
|---|---|---|
| 6,917,726 B2 | 7/2005 | Levene et al. |
| 7,033,764 B2 | 4/2006 | Korlach et al. |
| 7,041,812 B2 | 5/2006 | Kumar et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,302,146 B2 | 11/2007 | Turner et al. |
| 7,315,019 B2 | 1/2008 | Turner et al. |
| 7,763,423 B2 | 7/2010 | Roitman et al. |
| 7,907,800 B2 | 3/2011 | Foquet et al. |
| 7,968,702 B2 | 6/2011 | Wegener et al. |
| 7,981,632 B2 | 7/2011 | Schmidt |
| 8,153,375 B2 | 4/2012 | Travers et al. |
| 8,236,499 B2 | 8/2012 | Patel et al. |
| 8,715,930 B2 | 5/2014 | Pham et al. |
| 8,802,600 B2 | 8/2014 | Rank et al. |
| 8,906,670 B2 | 12/2014 | Gray et al. |
| 8,993,307 B2 | 3/2015 | Zaccarin et al. |
| 8,994,946 B2 | 3/2015 | McCaffrey et al. |
| 9,062,091 B2 | 6/2015 | Bjornson et al. |
| 9,399,766 B2 | 7/2016 | Kamtekar et al. |
| 9,547,003 B2 | 1/2017 | Howarth |
| 2001/0023288 A1* | 9/2001 | Wilbur ............... A61K 31/4188 530/391.1 |
| 2002/0039738 A1* | 4/2002 | Williams ............... C07H 19/10 435/6.12 |
| 2002/0168678 A1* | 11/2002 | Williams ............... C07H 19/10 435/6.12 |
| 2003/0044781 A1 | 3/2003 | Korlach et al. |
| 2003/0124576 A1 | 7/2003 | Kumar et al. |
| 2007/0036511 A1 | 2/2007 | Lundquist et al. |
| 2007/0072196 A1 | 3/2007 | Xu et al. |
| 2008/0032301 A1 | 2/2008 | Rank et al. |
| 2009/0208957 A1 | 8/2009 | Korlach et al. |
| 2009/0298075 A1 | 12/2009 | Travers et al. |
| 2010/0093555 A1 | 4/2010 | Bjornson et al. |
| 2010/0152424 A1 | 6/2010 | Korlach et al. |
| 2010/0167299 A1 | 7/2010 | Korlach |
| 2011/0059505 A1 | 3/2011 | Hanzel et al. |
| 2011/0189659 A1 | 8/2011 | Clark et al. |
| 2011/0220844 A1* | 9/2011 | Tulsky ................ C09B 68/4257 252/301.36 |
| 2012/0014837 A1 | 1/2012 | Fehr et al. |
| 2012/0019828 A1 | 1/2012 | McCaffrey et al. |
| 2012/0021525 A1 | 1/2012 | Fehr et al. |
| 2012/0034602 A1 | 2/2012 | Emig et al. |
| 2012/0085894 A1 | 4/2012 | Zhong et al. |
| 2013/0327644 A1 | 12/2013 | Turner et al. |
| 2013/0338010 A1 | 12/2013 | Turner et al. |
| 2014/0051068 A1 | 2/2014 | Cherf et al. |
| 2014/0094374 A1 | 4/2014 | Kamtekar et al. |
| 2014/0094375 A1 | 4/2014 | Kamtekar et al. |
| 2014/0179877 A1* | 6/2014 | Nilsson ................ A61K 31/704 525/418 |
| 2014/0272097 A1* | 9/2014 | Jung ......................... B41J 2/01 427/2.1 |
| 2015/0065353 A1 | 3/2015 | Turner et al. |
| 2016/0273026 A1* | 9/2016 | Webster ............... C12Q 1/6811 |
| 2017/0088592 A1 | 3/2017 | Liu et al. |

(Continued)

FOREIGN PATENT DOCUMENTS

| | | | |
|---|---|---|---|
| WO | 2007041342 A2 | 4/2007 | |
| WO | 2007123763 A2 | 11/2007 | |
| WO | 2009114182 A1 | 9/2009 | |

OTHER PUBLICATIONS

Niemeyer et al., 1999, DNA-Directed Immobilization: Efficient, Reversible, and Site-Selective Surface Binding of Proteins by Means of Covalent DNA-Streptavidin Conjugates, Analytical Biochemistry, 268: 54-63.*

(Continued)

*Primary Examiner* — Amber D Steele
(74) *Attorney, Agent, or Firm* — Monica Elrod-Erickson

(57) ABSTRACT

Compositions comprising covalently modified and mutated biotin-binding proteins, particularly biotin-binding proteins having a negative charge at physiological pH, are provided. Methods of producing such proteins are also provided, as are methods of immobilizing, sequencing, and making nucleic acids employing such proteins.

23 Claims, 12 Drawing Sheets

Specification includes a Sequence Listing.

(56) References Cited

U.S. PATENT DOCUMENTS

| | | | |
|---|---|---|---|
| 2017/0136433 A1 | 5/2017 | Sun et al. |
| 2017/0145495 A1 | 5/2017 | Sebo et al. |
| 2017/0145496 A1 | 5/2017 | Sebo et al. |
| 2017/0145502 A1 | 5/2017 | Shen et al. |
| 2017/0184580 A1 | 6/2017 | Shen et al. |

OTHER PUBLICATIONS

Ohara et al., 1995, A New Solid-Phase Chemical DNA Sequencing Method Which Uses Streptavidin-Coated Magnetic Beads, DNA Research, 2: 123-128.*

Agrawal et al., "Structural Characterization of Core-Bradavidin in Complex with Biotin," PLoS ONE (2017) 12(4):e0176086.

Argaraña, et al., "Molecular Cloning and Nucleotide Sequence of the Streptatividin Gene," Nucleic Acids Res. (1986) 14(4): 1871-1882.

Aslan, et al., "Engineered Single-Chain Dimeric Streptavidins with an Unexpected Strong Preference for Biotin-4-Fluorescein," J. Proc. Natl. Acad. Sci. USA (2005) 102(24):8507-8512.

Aslan, et al., "Engineering a Novel, Stable Dimeric Streptavidin with Lower Isolectric Point," Journal of Biotechnology (2007) 128:213-225.

Azido-PEG8-NHS ester. Datasheet [online] BroadPharm [retrieved on Apr. 25, 2019]. Retrieved from the Internet: https://broadpharm.com/web/product.php?catalog=BP-21606.

Baugh, et al., "A Distal Point Mutation in the Streptavidin-Biotin Complex Preserves Structure but Diminishes Binding Affinity: Experimental Evidence of Electronic Polarization Effects?" Biochemistry (2010) 49:4568-4570.

Bayer et al., "Preparation of Deglycosylated Egg White Avidin," Appl. Biochem. Biotechnol. (1995) 53(1):1-9.

Besanceney-Webler et al., "Increasing the Efficacy of Bioorthogonal Click Reactions for Bioconjugation" Angew. Chem. Int. Ed. (2011) 50:8051-8056.

Brune et al., "Dual Plug-and-Display Synthetic Assembly Using Orthogonal Reactive Proteins for Twin Antigen Immunization", Bioconjugate Chem. (2017) 28:1544-1551.

Carne, AF, "Chemical modification of proteins," Methods Mol Biol. 1994; 32:311-20.

Carrico, IS, "Chemoselective modification of proteins: hitting the target," Chem Soc Rev. Jul. 2008; 37(7):1423-31.

Chalker, JM et al., "Chemical modification of proteins at cysteine: opportunities in chemistry and biology," Chem Asian J. May 4, 2009;4(5):630-40.

Chivers et al., "A Streptavidin Variant with Slower Biotin Dissociation and Increased Mechanostability," Nature Methods (2010) 7(5):391-393.

Chivers et al., "How the Biotin-Streptavidin Interaction was Made Even Stronger: Investigation via Crystallography and Chimaeric Tetramer," Biochem J. (2011) 435(1):55-63.

DeTitta et al., "Carboxybiotin translocation mechanisms suggested by diffraction studies of biotin and its vitamers" Proc Natl Acad Sci USA. (1980) 77(1):333-7.

DiMarco et al., "Overview of the Main Methods Used to Combine Proteins with Nanosystems: Absorption, Bioconjugation, and Encapsulation," International Journal of Nanomedicine (2010) 5:37-49.

Driscoll et al., "Atomic-Scale Imaging of DNA Using Scanning Tunneling Microscopy," Nature (1990) 346(6281):294-296.

Dubacheva et al., "Controlling Multivalent Binding Through Surface Chemistry: Model Study on Streptavidin," JACS 139:4157-67. (2017).

Eid et al., "Real-Time DNA Sequencing From Single Polymerase Molecules," Science (2009) 323:133-138.

Fairhead et al., "SpyAvidin hubs enable precise and ultrastable orthogonal nanoassembly" J. Am. Chem. Soc. (2014) 136: 12355-12363.

Garlick and Giese, "Dissociative binding of alpha- and beta-sulphoxides of biotinylamidoethyl-3-(4-hydroxy-3-[125I]iodophenyl)propionamide to avidin" Biochemical Journal (1990) 268(3):611-613.

Gilbert et al, "Extracellular Self-Assembly of Functional and Tunable Protein Conjugates from Bacillus Subtilis," ACS Synthetic Biology (2017) 6:957-67.

Gitlin, et al., "Studies on the Biotin-Binding Site of Streptavidin," Biochem. J. (1988) 256:279-282.

Goodwin et al., Application of Single Molecule Detection to DNA Sequencing, Nucleosides & Nucleotides (1997) 16(5-6):543-550.

Hackenberger CP and Schwarzer D., "Chemoselective ligation and modification strategies for peptides and proteins," Angew Chem Int Ed Engl. 2008;47(52):10030-74.

Helppolainen et al., "Bradavidin II from Bradyrhizobium Japonicum: A New Avidin-Like Biotin-Binding Protein," Biochimic et Biophysica Acta (2008) 1784(7-8):1002-10.

Helppolainen et al., "Rhizavidin from Rhizobiumetli: the First Natural Dimer in the Avidin Protein Family," Biochem. J. (2007) 405: 397-405.

Hendrickson, et al., "Crystal Structure of Core Streptavidin Determined From Multiwavelength Anomalous Diffraction of Synchrotron Radiation," Proc. Natl. Acad. Sci. USA (1989) 86:2190-2194.

Howarth et al., "A Monovalent Streptavidin with Single Femtomolar Biotin Binding Site," Nat Methods (2006) 3: 267-273.

Howarth, "Smart Superglue in Streptococci? The Proof is in the Pulling," J. Biol. Chem. (2017) 292(21):8998-9.

Howorka et al., "Sequence-Specific Detection of Individual DNA Strands Using Engineered Nanopores," Nature Biotechnology (2001) 19(7):636-639.

Hyster, et al., "Biotinylated Rh(III) Complexes in Engineered Streptavidin for Accelerated Asymmetric C—H Activation," Science (2012) 338:500-503.

Hytonen et al., "Avidin Related Protein 2 Shows Unique Sructural and Functional Features Among the Avidin Protein Family," BMC Biotechnology (2005) 5:28.

Hytonen et al., "Chicken Avidin-Related Protein 4/5 Shows Superior Thermal Stability When Compared with Avdiin While Retaining High Affinity to Biotin," Journ. of Biol. Chem. (2004) 279:9337-43.

Jacobsen et al., "Amine Landscaping to Maximize Protein-Dye Fluorescence and Ultrastable Protein-Ligand Interaction," Cell Chemical Biology (2017) 24:1-8.

Kalia and Raines, "Advances in Bioconjugation," Curr. Org. Chem. (2020) 14(2):138-47.

Klumb, et al., "Energetic Roles of Hydrogen Bonds at the Ureido Oyegen Binding Pocket in the Streptavidin-Biotin Complex," Biochemistry (1998) 37(21):7657-63.

Korlach et al., "Long, Processive Enzymatic DNA Synthesis Using 100% Dye-Labeled Terminal Phosphate-Linked Nucleotides," Nucleosides, Nucleotides and Nucleic Acids (2008), 27:1072:1083.

Korlach et al., "Selective Aluminum Passivation for Targeted Immobilization of Single DNA Polymerase Molecules in Zero-Mode Waveguide Nanostructures," PNAS U.S.A. (2008) 105(4): 1176-1181.

Kurzban, et al., "The Quaternary Structure of Streptavidin in Urea," J. Biol. Chem. (1991) 266(22):14470-14477.

Lawrence et al., "Supercharging Proteins Can Impart Unusual Resilience," JACS (2007) 129:10110-12; including Supporting Information.

Levene et al., "Zero-mode Waveguides for Single-molecule Analysis at High Concentration" Science (2003) 299:682-686.

Livnah et al., "Three-Dimensional structures of Avidin and the Avidin-Biotin Complex," Proc. Natl. Acad. Sci. USA (1993) 90:5076-80.

Lundquist et al., "Parallel Confocal Detection of Single Molecules in Real Time," Optics Letters (2008) 33(9):1026-8.

Maatta et al., "Structural and Functional Characteristics of Xenavidin, the First Frog Avidin from Xenopus Tropicalis," BMC Structural Biology (2009) 9:63.

(56) References Cited

OTHER PUBLICATIONS

Marttila et al., "Recombinant NeutraLite Avidin: A Non-Glycosylated, Acidic Mutant of Chicken Avidin that Exhibits High Affinity for Biotin and Low Non-Specific Binding Properties," FEBS Letters (2000) 467(1):31-6.

Matsumoto et al., "Site-specific tetrameric streptavidin-protein conjugation using sortase A" Journal of Biotechnology (2011) 152:37-42.

Meller et al., "Rapid Nanopore Discrimination Between Single Polynucleotide Molecules," PNAS (2000)97)3):1079-1084.

Meyer et al., "Reduced Antibody Response to Streptavidin Through Site-Directed Mutagenesis," Protein Science (2001) 10:491-503.

M-PEG9-NHS ester. Datasheet [online] BroadPharm [retrieved on Apr. 25, 2019]. Retrieved from the Internet: https://broadpharm.com/web/product.php?catalog=BP-22624.

International Search Report and Written Opinion dated May 31, 2019 for related case PCT/US2018/067268.

Propargyl-PEG8-NHS ester. Datasheet [online] BroadPharm [retrieved on Apr. 25, 2019]. Retrieved from the Internet: https://broadpharm.com/web/product.php?catalog=BP-23778.

Propargyl-PEG9-alcohol. Datasheet [online] BroadPharm [retrieved on Apr. 25, 2019]. Retrieved from the Internet: https://broadpharm.com/web/product.php?catalog=BP-22056.

Rigler et al., "DNA-Sequencing at the Single Molecule Level," Journ. of Biotech. (2001) 86(3):161.

Sano, et al., "Molecular Engineering of Streptavidin," Annals of the New York Academy of Sciences 799 (Enzyme Engineering XIII) (1996) pp. 383-390.

Schmidt, et al., "One-Step Affinity Purification of Bacterially Produced Proteins by Means of the "Strep Tag" and Immobilized Recombinant Core Streptavidin," Journal of Chromatography A (1994) 676:337-345.

Shaw, "Selective Chemical Modification of Proteins," Physiol. Rev. (1970) 50(2):244-96.

Srisawat, et al., "Streptavidin Aptamers: Affinity Tags for the Study of RNAs and Ribonucleoproteins," RNA (2001) 7:632-641.

Stallings and DeTitta, "Crystallographic investigations of biotin and carboxybiotin derivatives" Ann N Y Acad Sci. (1985) 447:152-68.

Tahiri-Alaoui, et al., "High Affinity Nucleic Acid Aptamers for Streptavidin Incorporated into Bi-Specific Capture Ligands," Nucleic Acids Res. (2002) 30(10):e45.

Takakura, et al., "Tamavidins—Novel Avidin-Like Biotin-Binding Proteins from the Tamogitake Mushroom," FEBS Journal: (2009) 276: 1383-1397.

Taskinen et al., "A Novel Chimeric Avidin with Increased Thermal Stability Using DNA Shuffling," PLoS One (2014) 9(3):e92058.

Travers et al., "A Flexible and Efficient Template Format for Circular Consensus Sequencing and SNP Detection," Nucl. Acids Research (2010) 38(15):e159.

Veggiani et al., "Programmable polyproteams built using twin peptide superglues" Proc Natl Acad Sci USA (2016) 113(5):1202-7.

Voss, et al., "Mutagenesis of a Flexible Loop in Streptavidin Leads to Higher Affinity for the Strep-Tag II Peptide and Improved Performance in Recombinant Protein Purification," Protein Engineering (1997) 10(8):975-982.

Weber et al., "Structural Origins of High-Affinity Biotin Binding to Streptavidin," Science (1989) 243:85-88.

Wilbur, et al., "Streptavidin in Antibody Pretargeting. 4. Site-Directed Mutation Provides Evidence That Both Arginine and Lysine Residues are Involved in Kidney Localization," Bioconjugate Chem. (2004) 15:1454-1463.

Wormser et al., "Synthesis and Growth-Promoting Activity of dl-cis-Hexahydro-4-( 4-carboxybutyl)-2-cyclopentimidazolone: Carbobiotin" Journal of Pharmaceutical Sciences (1972) 61(7):1168-1170.

Yamakura, F. and Ikeda, K., "Modification of tryptophan and tryptophan residues in proteins by reactive nitrogen species," Nitric Oxide. Mar. 2006; 14(2):152-61.

Zakeri et al., "Peptide tag forming a rapid covalent bond to a protein, through engineering a bacterial adhesin" Proc Natl Acad Sci USA (2012) 109(12):E690-7.

\* cited by examiner

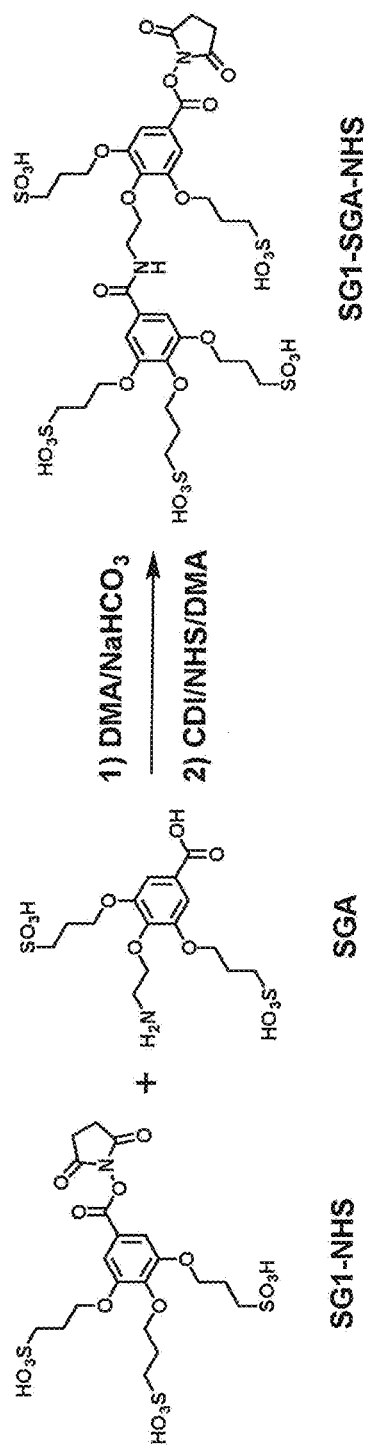
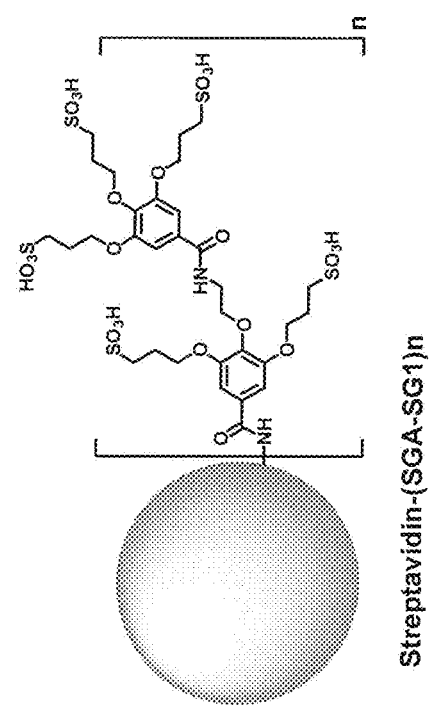
Fig. 10A
Fig. 10B

SEQUENCE LISTING

```
<160> NUMBER OF SEQ ID NOS: 29

<210> SEQ ID NO 1
<211> LENGTH: 126
<212> TYPE: PRT
<213> ORGANISM: Streptomyces avidinii

<400> SEQUENCE: 1

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
            20                  25                  30

Ala Val Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125

<210> SEQ ID NO 2
<211> LENGTH: 159
<212> TYPE: PRT
<213> ORGANISM: Streptomyces avidinii

<400> SEQUENCE: 2

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125
```

Thr Phe Thr Lys Val Lys Pro Ser Ala Ala Ser Ile Asp Ala Ala Lys
            130                 135                 140

Lys Ala Gly Val Asn Asn Gly Asn Pro Leu Asp Ala Val Gln Gln
145                 150                 155

<210> SEQ ID NO 3
<211> LENGTH: 150
<212> TYPE: PRT
<213> ORGANISM: Artificial Sequence
<220> FEATURE:
<223> OTHER INFORMATION: tagged streptavidin

<400> SEQUENCE: 3

Met Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser Glu
        115                 120                 125

Glu Glu Glu Glu Glu Glu Glu Glu Glu Asn Leu Tyr Phe Gln Gly
    130                 135                 140

His His His His His His
145                 150

<210> SEQ ID NO 4
<211> LENGTH: 150
<212> TYPE: PRT
<213> ORGANISM: Artificial Sequence
<220> FEATURE:
<223> OTHER INFORMATION: tagged streptavidin

<400> SEQUENCE: 4

Met Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser Lys
        115                 120                 125

Lys Lys Lys Lys Lys Lys Lys Glu Asn Leu Tyr Phe Gln Gly
            130                 135                 140

His His His His His His
145                 150

<210> SEQ ID NO 5
<211> LENGTH: 138
<212> TYPE: PRT
<213> ORGANISM: Artificial Sequence
<220> FEATURE:
<223> OTHER INFORMATION: tagged streptavidin

<400> SEQUENCE: 5

Met Gly Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Lys Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Lys Ser Thr
            100                 105                 110

Leu Val Gly His Asp Thr Phe Thr Lys Val Lys Pro Ser Ala Ala Ser
        115                 120                 125

Glu Glu Glu Glu Glu Glu Glu Glu Glu Glu
    130                 135

<210> SEQ ID NO 6
<211> LENGTH: 128
<212> TYPE: PRT
<213> ORGANISM: Artificial Sequence
<220> FEATURE:
<223> OTHER INFORMATION: mutant streptavidin

<400> SEQUENCE: 6

Met Gly Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Arg Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Lys Ser Thr
            100                 105                 110

Leu Val Gly His Asp Thr Phe Thr Lys Val Lys Pro Ser Ala Ala Ser
        115                 120                 125

```
<210> SEQ ID NO 7
<211> LENGTH: 128
<212> TYPE: PRT
<213> ORGANISM: Artificial Sequence
<220> FEATURE:
<223> OTHER INFORMATION: mutant streptavidin

<400> SEQUENCE: 7
```

Met Gly Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Lys Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Arg Ser Thr
            100                 105                 110

Leu Val Gly His Asp Thr Phe Thr Lys Val Lys Pro Ser Ala Ala Ser
        115                 120                 125

```
<210> SEQ ID NO 8
<211> LENGTH: 128
<212> TYPE: PRT
<213> ORGANISM: Artificial Sequence
<220> FEATURE:
<223> OTHER INFORMATION: mutant streptavidin

<400> SEQUENCE: 8
```

Met Gly Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Lys Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Lys Ser Thr
            100                 105                 110

Leu Val Gly His Asp Thr Phe Thr Arg Val Arg Pro Ser Ala Ala Ser
        115                 120                 125

```
<210> SEQ ID NO 9
<211> LENGTH: 128
<212> TYPE: PRT
<213> ORGANISM: Artificial Sequence
<220> FEATURE:
<223> OTHER INFORMATION: mutant streptavidin
```

<400> SEQUENCE: 9

Met Gly Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Arg Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Arg Ser Thr
            100                 105                 110

Leu Val Gly His Asp Thr Phe Thr Arg Val Arg Pro Ser Ala Ala Ser
        115                 120                 125

<210> SEQ ID NO 10
<211> LENGTH: 128
<212> TYPE: PRT
<213> ORGANISM: Artificial Sequence
<220> FEATURE:
<223> OTHER INFORMATION: mutant streptavidin

<400> SEQUENCE: 10

Met Gly Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Arg Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Arg Ser Thr
            100                 105                 110

Leu Val Gly His Asp Thr Phe Thr Lys Val Lys Pro Ser Ala Ala Ser
        115                 120                 125

<210> SEQ ID NO 11
<211> LENGTH: 128
<212> TYPE: PRT
<213> ORGANISM: Artificial Sequence
<220> FEATURE:
<223> OTHER INFORMATION: mutant streptavidin

<400> SEQUENCE: 11

Met Gly Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
            50                  55                  60

Thr Val Ala Trp Lys Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Arg Ser Thr
                100                 105                 110

Leu Val Gly His Asp Thr Phe Thr Arg Val Arg Pro Ser Ala Ala Ser
                115                 120                 125

<210> SEQ ID NO 12
<211> LENGTH: 128
<212> TYPE: PRT
<213> ORGANISM: Artificial Sequence
<220> FEATURE:
<223> OTHER INFORMATION: mutant streptavidin

<400> SEQUENCE: 12

Met Gly Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
                20                  25                  30

Glu Ser Ala Val Gly Asn Ala Glu Ser Arg Tyr Val Leu Thr Gly Arg
            35                  40                  45

Tyr Asp Ser Ala Pro Ala Thr Asp Gly Ser Gly Thr Ala Leu Gly Trp
            50                  55                  60

Thr Val Ala Trp Arg Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Lys Ser Thr
                100                 105                 110

Leu Val Gly His Asp Thr Phe Thr Arg Val Arg Pro Ser Ala Ala Ser
                115                 120                 125

<210> SEQ ID NO 13
<211> LENGTH: 138
<212> TYPE: PRT
<213> ORGANISM: Artificial Sequence
<220> FEATURE:
<223> OTHER INFORMATION: tagged streptavidin

<400> SEQUENCE: 13

Met Gly Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
                20                  25                  30

Glu Ser Ala Val Gly Asn Ala Glu Ser Arg Tyr Val Leu Thr Gly Arg
            35                  40                  45

Tyr Asp Ser Ala Pro Ala Thr Asp Gly Ser Gly Thr Ala Leu Gly Trp
            50                  55                  60

Thr Val Ala Trp Lys Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Lys Ser Thr
                100                 105                 110

```
Leu Val Gly His Asp Thr Phe Thr Lys Val Lys Pro Ser Ala Ala Ser
            115                 120                 125
Lys Lys Lys Lys Lys Lys Lys Lys Lys
    130                 135
```

<210> SEQ ID NO 14
<211> LENGTH: 128
<212> TYPE: PRT
<213> ORGANISM: Artificial Sequence
<220> FEATURE:
<223> OTHER INFORMATION: mutant streptavidin

<400> SEQUENCE: 14

```
Met Gly Arg Ala Gly Ile Thr Gly Thr Trp Tyr Asn Gln Leu Gly Ser
1               5                   10                  15
Thr Phe Ile Val Thr Ala Gly Ala Asp Gly Ala Leu Thr Gly Thr Tyr
                20                  25                  30
Glu Ser Ala Val Gly Asn Ala Glu Ser Arg Tyr Val Leu Thr Gly Arg
            35                  40                  45
Tyr Asp Ser Ala Pro Ala Thr Asp Gly Ser Gly Thr Ala Leu Gly Trp
    50                  55                  60
Thr Val Ala Trp Lys Asn Asn Tyr Arg Asn Ala His Ser Ala Thr Thr
65                  70                  75                  80
Trp Ser Gly Gln Tyr Val Gly Gly Ala Arg Ala Arg Ile Asn Thr Gln
                85                  90                  95
Trp Leu Leu Thr Ser Gly Thr Thr Arg Ala Asn Ala Trp Lys Ser Thr
            100                 105                 110
Leu Val Gly His Asp Thr Phe Thr Lys Val Lys Arg Ala Ala Ser
        115                 120                 125
```

<210> SEQ ID NO 15
<211> LENGTH: 153
<212> TYPE: PRT
<213> ORGANISM: Artificial Sequence
<220> FEATURE:
<223> OTHER INFORMATION: tagged streptavidin

<400> SEQUENCE: 15

```
Met Gly Glu Ala Gly Ile Thr Gly Thr Trp Tyr Asn Gln Leu Gly Ser
1               5                   10                  15
Thr Phe Ile Val Thr Ala Gly Ala Asp Gly Ala Leu Thr Gly Thr Tyr
                20                  25                  30
Glu Ser Ala Val Gly Asn Ala Glu Ser Arg Tyr Val Leu Thr Gly Arg
            35                  40                  45
Tyr Asp Ser Ala Pro Ala Thr Asp Gly Ser Gly Thr Ala Leu Gly Trp
    50                  55                  60
Thr Val Ala Trp Lys Asn Asn Tyr Arg Asn Ala His Ser Ala Thr Thr
65                  70                  75                  80
Trp Ser Gly Gln Tyr Val Gly Gly Ala Glu Ala Arg Ile Asn Thr Gln
                85                  90                  95
Trp Leu Leu Thr Ser Gly Thr Thr Glu Ala Asn Ala Trp Lys Ser Thr
            100                 105                 110
Leu Val Gly His Asp Thr Phe Thr Lys Val Lys Pro Ser Ala Ala Ser
        115                 120                 125
Gly Gly Gly Ser Leu Val Pro Arg Gly Ser Gly Gly Ser Tyr Gly
    130                 135                 140
Arg Lys Lys Arg Arg Gln Arg Arg Arg
145                 150
```

<210> SEQ ID NO 16
<211> LENGTH: 128
<212> TYPE: PRT
<213> ORGANISM: Artificial Sequence
<220> FEATURE:
<223> OTHER INFORMATION: mutant streptavidin

<400> SEQUENCE: 16

```
Met Gly Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
            20                  25                  30

Glu Ser Ala Val Gly Asn Ala Glu Gly Asp Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Lys Asn Asn Tyr Asp Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Lys Ser Thr
            100                 105                 110

Leu Val Gly His Asp Thr Phe Thr Lys Val Lys Pro Ser Ala Ala Ser
        115                 120                 125
```

<210> SEQ ID NO 17
<211> LENGTH: 128
<212> TYPE: PRT
<213> ORGANISM: Artificial Sequence
<220> FEATURE:
<223> OTHER INFORMATION: mutant streptavidin

<400> SEQUENCE: 17

```
Met Gly Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
            20                  25                  30

Glu Ser Ala Val Gly Asn Ala Glu Gly Asp Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Lys Asn Asn Tyr Arg Asn Ala His Ser Ala Thr Thr
65                  70                  75                  80

Trp Ser Gly Gln Tyr Val Gly Gly Ala Glu Ala Asp Ile Asn Thr Gln
                85                  90                  95

Trp Leu Leu Thr Ser Gly Thr Thr Glu Ala Asn Ala Trp Lys Ser Thr
            100                 105                 110

Leu Val Gly His Asp Thr Phe Thr Lys Val Lys Pro Ser Ala Ala Ser
        115                 120                 125
```

<210> SEQ ID NO 18
<211> LENGTH: 140
<212> TYPE: PRT
<213> ORGANISM: Artificial Sequence
<220> FEATURE:
<223> OTHER INFORMATION: mutant streptavidin -continued

```
<400> SEQUENCE: 18

Met His His His His His Leu Val Pro Arg Gly Ser Gly Glu Asp
1               5                   10                  15

Gly Ile Thr Gly Thr Trp Tyr Asn Gln Leu Gly Ser Thr Phe Ile Val
            20                  25                  30

Thr Ala Gly Ala Asp Gly Ala Leu Thr Gly Thr Tyr Glu Ser Ala Val
        35                  40                  45

Gly Asn Ala Glu Ser Arg Tyr Val Leu Thr Gly Arg Tyr Asp Ser Ala
    50                  55                  60

Pro Ala Asp Asp Gly Ser Gly Thr Ala Leu Gly Trp Thr Val Ala Trp
65                  70                  75                  80

Lys Asn Asp Tyr Arg Asn Ala His Ser Ala Thr Thr Trp Ser Gly Gln
                85                  90                  95

Tyr Val Gly Gly Ala Glu Ala Arg Ile Asn Thr Gln Trp Leu Leu Thr
            100                 105                 110

Ser Gly Thr Thr Glu Ala Asn Ala Trp Lys Ser Thr Leu Val Gly His
        115                 120                 125

Asp Thr Phe Thr Lys Val Lys Pro Ser Ala Ala Ser
    130                 135                 140

<210> SEQ ID NO 19
<211> LENGTH: 140
<212> TYPE: PRT
<213> ORGANISM: Artificial Sequence
<220> FEATURE:
<223> OTHER INFORMATION: mutant streptavidin

<400> SEQUENCE: 19

Met His His His His His Leu Val Pro Arg Gly Ser Gly Glu Ala
1               5                   10                  15

Gly Ile Thr Gly Thr Trp Tyr Asn Gln Leu Gly Ser Thr Phe Ile Val
            20                  25                  30

Thr Ala Gly Glu Asp Gly Ala Leu Thr Gly Thr Tyr Glu Ser Ala Val
        35                  40                  45

Gly Asn Ala Glu Ser Arg Tyr Val Leu Thr Gly Arg Tyr Asp Ser Ala
    50                  55                  60

Pro Ala Thr Asp Gly Ser Gly Thr Ala Leu Gly Trp Thr Val Ala Trp
65                  70                  75                  80

Lys Asn Asn Tyr Arg Asn Ala His Ser Ala Thr Thr Trp Ser Gly Gln
                85                  90                  95

Tyr Val Gly Gly Ala Glu Ala Arg Ile Asn Thr Gln Trp Leu Leu Thr
            100                 105                 110

Ser Gly Thr Thr Glu Glu Asn Ala Trp Lys Ser Thr Leu Val Gly His
        115                 120                 125

Asp Thr Phe Thr Lys Val Glu Pro Ser Ala Ala Ser
    130                 135                 140

<210> SEQ ID NO 20
<211> LENGTH: 140
<212> TYPE: PRT
<213> ORGANISM: Artificial Sequence
<220> FEATURE:
<223> OTHER INFORMATION: mutant streptavidin
```

<400> SEQUENCE: 20

Met His His His His His Leu Val Pro Arg Gly Ser Gly Glu Asp
1               5                   10                  15

Gly Ile Thr Gly Thr Trp Tyr Asn Gln Leu Gly Ser Thr Phe Ile Val
            20                  25                  30

Thr Ala Gly Glu Asp Gly Ala Leu Thr Gly Thr Tyr Glu Ser Ala Val
        35                  40                  45

Gly Asn Ala Glu Ser Arg Tyr Val Leu Thr Gly Arg Tyr Asp Ser Ala
    50                  55                  60

Pro Ala Asp Asp Gly Ser Gly Thr Ala Leu Gly Trp Thr Val Ala Trp
65                  70                  75                  80

Lys Asn Asp Tyr Arg Asn Ala His Ser Ala Thr Thr Trp Ser Gly Gln
                85                  90                  95

Tyr Val Gly Gly Ala Glu Ala Arg Ile Asn Thr Gln Trp Leu Leu Thr
            100                 105                 110

Ser Gly Thr Thr Glu Glu Asn Ala Trp Lys Ser Thr Leu Val Gly His
        115                 120                 125

Asp Thr Phe Thr Lys Val Glu Pro Ser Ala Ala Ser
    130                 135                 140

<210> SEQ ID NO 21
<211> LENGTH: 140
<212> TYPE: PRT
<213> ORGANISM: Artificial Sequence
<220> FEATURE:
<223> OTHER INFORMATION: mutant streptavidin

<400> SEQUENCE: 21

Met His His His His His Leu Val Pro Arg Gly Ser Gly Glu Asp
1               5                   10                  15

Gly Ile Thr Gly Thr Trp Tyr Asn Gln Leu Gly Ser Thr Phe Ile Val
            20                  25                  30

Thr Ala Gly Glu Asp Gly Ala Leu Thr Gly Thr Tyr Glu Ser Ala Val
        35                  40                  45

Gly Asn Ala Glu Ser Arg Tyr Val Leu Thr Gly Arg Tyr Asp Ser Ala
    50                  55                  60

Pro Ala Asp Asp Gly Ser Gly Thr Ala Leu Gly Trp Thr Val Ala Trp
65                  70                  75                  80

Lys Asn Asp Tyr Arg Asn Ala His Ser Ala Thr Thr Trp Ser Gly Gln
                85                  90                  95

Tyr Val Gly Gly Glu Glu Ala Arg Ile Glu Thr Gln Trp Leu Leu Thr
            100                 105                 110

Ser Gly Thr Thr Glu Glu Asn Ala Trp Lys Ser Thr Leu Val Gly His
        115                 120                 125

Asp Thr Phe Asp Lys Val Glu Pro Ser Ala Ala Ser
    130                 135                 140

<210> SEQ ID NO 22
<211> LENGTH: 140
<212> TYPE: PRT
<213> ORGANISM: Artificial Sequence
<220> FEATURE:
<223> OTHER INFORMATION: mutant streptavidin

<400> SEQUENCE: 22

Met His His His His His Leu Val Pro Arg Gly Ser Gly Glu Asp
1               5                   10                  15

Gly Ile Thr Gly Thr Trp Tyr Asn Gln Leu Gly Ser Asp Phe Ile Val
            20                  25                  30

Thr Ala Gly Glu Asp Gly Ala Leu Thr Gly Thr Tyr Glu Ser Ala Val
        35                  40                  45

Gly Asn Ala Glu Ser Arg Tyr Val Leu Thr Gly Arg Tyr Asp Ser Ala
    50                  55                  60

Pro Ala Asp Asp Gly Ser Gly Thr Ala Leu Gly Trp Thr Val Ala Trp
65                  70                  75                  80

Lys Asn Asp Tyr Arg Asn Ala His Ser Ala Thr Thr Trp Ser Gly Gln
                85                  90                  95

Tyr Val Gly Gly Glu Glu Asp Arg Ile Glu Thr Gln Trp Leu Leu Thr
            100                 105                 110

Ser Gly Thr Thr Glu Glu Asn Ala Trp Lys Ser Thr Leu Val Gly His
        115                 120                 125

Asp Asp Phe Asp Lys Val Glu Pro Ser Ala Ala Ser
    130                 135                 140

<210> SEQ ID NO 23
<211> LENGTH: 140
<212> TYPE: PRT
<213> ORGANISM: Artificial Sequence
<220> FEATURE:
<223> OTHER INFORMATION: mutant streptavidin

<400> SEQUENCE: 23

Met His His His His His Leu Val Pro Arg Gly Ser Gly Glu Ala
1               5                   10                  15

Gly Ile Thr Gly Thr Trp Tyr Ala Gln Leu Gly Asp Thr Phe Ile Val
            20                  25                  30

Thr Ala Gly Ala Asp Gly Ala Leu Thr Gly Thr Tyr Glu Ala Ala Val
        35                  40                  45

Gly Asn Ala Glu Ser Arg Tyr Val Leu Thr Gly Arg Tyr Asp Ser Ala
    50                  55                  60

Pro Ala Thr Asp Gly Ser Gly Thr Ala Leu Gly Trp Thr Val Ala Trp
65                  70                  75                  80

Lys Asn Asn Tyr Arg Asn Ala His Ser Ala Thr Thr Trp Ser Gly Gln
                85                  90                  95

Tyr Val Gly Gly Ala Glu Ala Arg Ile Asn Thr Gln Trp Leu Leu Thr
            100                 105                 110

Ser Gly Thr Thr Glu Ala Asn Ala Trp Lys Ser Thr Leu Val Gly His
        115                 120                 125

Asp Thr Phe Thr Lys Val Lys Pro Ser Ala Ala Ser
    130                 135                 140

<210> SEQ ID NO 24
<211> LENGTH: 138
<212> TYPE: PRT
<213> ORGANISM: Artificial Sequence
<220> FEATURE:
<223> OTHER INFORMATION: mutant streptavidin

<400> SEQUENCE: 24

Met Gly Glu Ala Gly Ile Thr Gly Thr Trp Tyr Asn Gln Leu Gly Ser
1               5                   10                  15

Thr Phe Ile Val Thr Ala Gly Glu Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Lys Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Glu Asn Ala Trp Lys Ser Thr
            100                 105                 110

Leu Val Gly His Asp Thr Phe Thr Lys Val Glu Pro Ser Ala Ala Ser
        115                 120                 125

Glu Glu Glu Glu Glu Glu Glu Glu
    130                 135

<210> SEQ ID NO 25
<211> LENGTH: 138
<212> TYPE: PRT
<213> ORGANISM: Artificial Sequence
<220> FEATURE:
<223> OTHER INFORMATION: mutant streptavidin

<400> SEQUENCE: 25

Met Gly Glu Ala Gly Ile Thr Gly Thr Trp Tyr Asn Gln Leu Gly Ser
1               5                   10                  15

Thr Phe Ile Val Thr Ala Gly Glu Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Lys Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Glu Asn Ala Trp Lys Ser Thr
            100                 105                 110

Leu Val Gly His Asp Thr Phe Thr Lys Val Glu Pro Ser Ala Ala Ser
        115                 120                 125

Lys Lys Lys Lys Lys Lys Lys Lys Lys Lys
    130                 135

<210> SEQ ID NO 26
<211> LENGTH: 148
<212> TYPE: PRT
<213> ORGANISM: Artificial Sequence
<220> FEATURE:
<223> OTHER INFORMATION: mutant streptavidin

```
<400> SEQUENCE: 26

Met Glu Glu Glu Glu Glu Glu Glu Glu Gly Glu Ala Gly Ile
1               5                   10                  15

Thr Gly Thr Trp Tyr Asn Gln Leu Gly Ser Thr Phe Ile Val Thr Ala
            20                  25                  30

Gly Glu Asp Gly Ala Leu Thr Gly Thr Tyr Glu Ser Ala Val Gly Asn
            35                  40                  45

Ala Glu Ser Arg Tyr Val Leu Thr Gly Arg Tyr Asp Ser Ala Pro Ala
        50                  55                  60

Thr Asp Gly Ser Gly Thr Ala Leu Gly Trp Thr Val Ala Trp Lys Asn
65                  70                  75                  80

Asn Tyr Arg Asn Ala His Ser Ala Thr Thr Trp Ser Gly Gln Tyr Val
                85                  90                  95

Gly Gly Ala Glu Ala Arg Ile Asn Thr Gln Trp Leu Leu Thr Ser Gly
            100                 105                 110

Thr Thr Glu Glu Asn Ala Trp Lys Ser Thr Leu Val Gly His Asp Thr
            115                 120                 125

Phe Thr Lys Val Glu Pro Ser Ala Ala Ser Glu Glu Glu Glu Glu
            130                 135                 140

Glu Glu Glu Glu
145

<210> SEQ ID NO 27
<211> LENGTH: 11
<212> TYPE: PRT
<213> ORGANISM: Artificial Sequence
<220> FEATURE:
<223> OTHER INFORMATION: synthetic Tat fusion peptide

<400> SEQUENCE: 27

Tyr Gly Arg Lys Lys Arg Arg Gln Arg Arg Arg
1               5                   10

<210> SEQ ID NO 28
<211> LENGTH: 7
<212> TYPE: PRT
<213> ORGANISM: Artificial Sequence
<220> FEATURE:
<223> OTHER INFORMATION: synthetic TEV protease site

<400> SEQUENCE: 28

Glu Asn Leu Tyr Phe Gln Gly
1               5

<210> SEQ ID NO 29
<211> LENGTH: 6
<212> TYPE: PRT
<213> ORGANISM: Artificial Sequence
<220> FEATURE:
<223> OTHER INFORMATION: synthetic thrombin site

<400> SEQUENCE: 29

Leu Val Pro Arg Gly Ser
1               5
```

MODIFIED BIOTIN-BINDING PROTEINS FOR IMMOBILIZATION

CROSS-REFERENCE TO RELATED APPLICATIONS

This application is a non-provisional utility patent application claiming priority to and benefit of provisional patent application U.S. Ser. No. 62/609,680, filed Dec. 22, 2017, entitled "MODIFIED BIOTIN-BINDING PROTEINS FOR IMMOBILIZATION" by Satwik Kamtekar et al., which is incorporated herein by reference in its entirety for all purposes.

INCORPORATION-BY-REFERENCE OF MATERIAL SUBMITTED BY U.S.P.T.O. eFS-WEB

The instant application contains a Sequence Listing which is being submitted in computer readable form via the United States Patent and Trademark Office eFS-WEB system and which is hereby incorporated by reference in its entirety for all purposes. The txt file submitted herewith contains a 34 KB file (01021801_2019-04-26_SequenceListing.txt).

STATEMENT AS TO RIGHTS TO INVENTIONS MADE UNDER FEDERALLY SPONSORED RESEARCH AND DEVELOPMENT

Not applicable.

BACKGROUND OF THE INVENTION

Techniques in molecular biology and molecular medicine often rely on analysis of single biological molecules. Such techniques include DNA and RNA sequencing, polymorphism detection, detection of proteins of interest, detection of protein-nucleic acid complexes, and many others. The high sensitivity, high throughput and low reagent costs involved in single molecule analysis make this type of analysis an increasingly attractive approach for a variety of detection and analysis problems in molecular medicine, from low cost genomics to high sensitivity marker analysis.

Many techniques for single molecule analysis rely on immobilization of the molecule or complex of interest on a solid support, typically within an optical confinement reaction/observation region such as a zero mode waveguide Immobilization of a given molecule must be robust, since dissociation means that molecule is lost to further analysis.

Immobilization of biological molecules is frequently accomplished by capture through moieties such as biotin. Biotin is a cofactor that is covalently attached to several enzymes involved in the transfer of activated carboxyl groups. Biotin labeling of molecules not normally biotinylated can be used to label, detect, purify, and/or immobilize such molecules. These methods also rely upon proteins such as avidin or streptavidin, which bind very tightly and specifically to biotin. However, single molecule analysis imposes challenges not seen in analysis of bulk samples, since it relies on robust immobilization of individual molecules rather than of a population of such molecules.

Improved methods for immobilizing single molecules and complexes are therefore desirable. The invention described herein fulfills these and other needs, as will be apparent upon review of the following.

SUMMARY OF THE INVENTION

One general class of embodiments provides a composition comprising a modified biotin-binding protein that comprises one or more covalently attached sulfonate moieties, e.g., three or more, 12 or more, 24 or more, 30 or more, 45 or more, or 60 or more covalently attached sulfonate moieties. For example, the biotin-binding protein can comprise one or more covalently attached 3,4,5-tris(3-sulfopropoxy)benzoyl, 3,5-disulfobenzoyl, 2-sulfobenzoyl, and/or polyethylene glycol (PEG) moieties, e.g., four or more, 10 or more, 15 or more, 20 or more, or 45 or more. In some embodiments, the biotin-binding protein is a tetravalent biotin-binding protein, e.g., streptavidin. In one exemplary class of embodiments, the biotin-binding protein is a tetravalent biotin-binding protein (e.g., streptavidin) comprising 15 or more covalently attached 3,4,5-tris(3-sulfopropoxy)benzoyl moieties. In some embodiments, the biotin-binding protein comprises one or more amino acid substitutions that decrease its calculated net charge relative to a parental biotin-binding protein. In some embodiments, the biotin-binding protein has a calculated net charge of −20 or less at pH 7.4.

Optionally, the biotin-binding protein is bound to a nucleic acid polymerase, e.g., a nucleic acid polymerase that is complexed with a nucleic acid. In some embodiments, the biotin-binding protein is immobilized on a solid support. In some embodiments, the biotin-binding protein is immobilized on the base of a nanoscale well. The composition is optionally present in a nucleic acid sequencing system.

One general class of embodiments provides methods of producing a modified biotin-binding protein that include providing a parental biotin-binding protein and covalently modifying one or more amino acid residues in the parental biotin-binding protein to produce a modified biotin-binding protein that comprises one or more covalent modifications that decrease its calculated net charge relative to the parental biotin-binding protein. In some embodiments, the modified biotin-binding protein has a calculated net charge of −20 or less at pH 7.4.

Covalently modifying one or more amino acid residues in the parental biotin-binding protein can comprise covalently modifying one or more positively charged residues in the parental biotin-binding protein. For example, covalently modifying one or more amino acid residues in the parental biotin-binding protein can comprise covalently modifying one or more lysine residues in the parental biotin-binding protein, e.g., by reaction with an N-hydroxysuccinimide ester of 3,4,5-tris(3-sulfopropoxy)benzoic acid, an N-hydroxysuccinimide ester of 4-(6-azidohexyloxy)-3,5-bis(3-sulfopropoxy)benzoic acid, an N-hydroxysuccinimide ester of 3,5-disulfobenzoic acid, or 2-sulfobenzoic acid cyclic anhydride.

In some embodiments, the one or more covalent modifications comprise one or more negatively charged groups. For example, the one or more covalent modifications can comprise one or more covalently attached sulfonate moieties (e.g., 3,4,5-tris(3-sulfopropoxy)benzoyl moieties, 3,5-disulfobenzoyl moieties, or 2-sulfobenzoyl moieties), carboxylic acid groups, sulfinic acid groups, phosphate groups, phosphinic acid groups, or phosphonic acid groups. In some embodiments, the parental and modified biotin-binding proteins are tetravalent biotin-binding proteins, e.g, streptavidin.

One general class of embodiments provides a substrate comprising at least one nanoscale well in which is immobilized a biotin-binding protein, which biotin-binding protein has a calculated net charge of −20 or less at pH 7.4, e.g., −44 or less, −60 or less, or −80 or less. Optionally, a polymerase-nucleic acid complex is bound to the biotin-binding protein.

In one class of embodiments, the biotin-binding protein is a tetravalent biotin-binding protein, e.g., streptavidin. In some embodiments, the biotin-binding protein comprises one or more covalent modifications that decrease its calculated net charge relative to a parental biotin-binding protein lacking the covalent modifications. For example, the biotin-binding protein can comprise one or more covalently attached sulfonate moieties, e.g., one or more covalently attached 3,4,5-tris(3-sulfopropoxy)benzoyl moieties. In some embodiments, the biotin-binding protein comprises one or more amino acid substitutions that decrease its calculated net charge relative to a parental biotin-binding protein, e.g., one or more amino acid substitutions that replace a positively charged or uncharged residue in the parental biotin-binding protein with a negatively charged residue. In some embodiments, the biotin-binding protein comprises a polyglutamate tag.

In some embodiments, the substrate comprises at least 500,000 nanoscale wells, a plurality of which comprise an immobilized biotin-binding protein. The substrate is optionally present in a nucleic acid sequencing system.

Another general class of embodiments provides a complex comprising a biotin-binding protein and a nucleic acid. The biotin-binding protein has a calculated net charge of −20 or less at pH 7.4, e.g., −44 or less, −60 or less, or −80 or less. In some embodiments, the nucleic acid is at least about 100 nucleotides in length. In some embodiments, the nucleic acid is a DNA that comprises a double-stranded region at least 1 kb in length. The complex optionally includes a nucleic acid polymerase that is bound to the nucleic acid. The polymerase can comprise a bis-biotin tag through which the polymerase is bound to the biotin-binding protein.

In one class of embodiments, the biotin-binding protein is a tetravalent biotin-binding protein, e.g., streptavidin. In some embodiments, the biotin-binding protein comprises one or more covalent modifications that decrease its calculated net charge relative to a parental biotin-binding protein lacking the covalent modification. In some embodiments, the biotin-binding protein comprises one or more covalently attached sulfonate moieties, e.g., one or more covalently attached 3,4,5-tris(3-sulfopropoxy)benzoyl moieties. In some embodiments, the biotin-binding protein comprises one or more amino acid substitutions that decrease its calculated net charge relative to a parental biotin-binding protein, e.g., one or more amino acid substitutions that replace a positively charged or uncharged residue in the parental biotin-binding protein with a negatively charged residue. In some embodiments, the biotin-binding protein comprises a polyglutamate tag.

In some embodiments, the biotin-binding protein is immobilized on a solid support. In some embodiments, the biotin-binding protein is immobilized on the base of a nanoscale well. The complex is optionally present in a nucleic acid sequencing system.

Another general class of embodiments provides a complex comprising a biotin-binding protein and a nucleic acid polymerase. The biotin-binding protein has a calculated net charge of −20 or less at pH 7.4, e.g., −44 or less, −60 or less, or −80 or less. The polymerase optionally comprises a bis-biotin tag through which the polymerase is bound to the biotin-binding protein.

In one class of embodiments, the biotin-binding protein is a tetravalent biotin-binding protein, e.g., streptavidin. In some embodiments, the biotin-binding protein comprises one or more covalent modifications that decrease its calculated net charge relative to a parental biotin-binding protein lacking the covalent modification. In some embodiments, the biotin-binding protein comprises one or more covalently attached sulfonate moieties, e.g., one or more covalently attached 3,4,5-tris(3-sulfopropoxy)benzoyl moieties. In some embodiments, the biotin-binding protein comprises one or more amino acid substitutions that decrease its calculated net charge relative to a parental biotin-binding protein, e.g., one or more amino acid substitutions that replace a positively charged or uncharged residue in the parental biotin-binding protein with a negatively charged residue. In some embodiments, the biotin-binding protein comprises a polyglutamate tag.

In some embodiments, the biotin-binding protein is immobilized on a solid support. In some embodiments, the biotin-binding protein is immobilized on the base of a nanoscale well. The complex is optionally present in a nucleic acid sequencing system.

One general class of embodiments provides methods of immobilizing a nucleic acid that include providing a surface comprising a plurality of array regions, which array regions comprise biotin or a biotin analog, and exposing the surface to a complex comprising a nucleic acid and a biotin-binding protein, whereby the biotin-binding protein binds to the biotin or biotin analog and thereby immobilizes the complex in the array regions. The biotin-binding protein has a calculated net charge of −20 or less at pH 7.4, e.g., −44 or less, −60 or less, or −80 or less. The array regions optionally comprise nanoscale wells or nanopores.

In some embodiments, the nucleic acid is at least about 100 nucleotides in length. In some embodiments, the nucleic acid is a DNA that comprises a double-stranded region at least 1 kb in length. The complex optionally includes a nucleic acid polymerase that is bound to the nucleic acid. The polymerase can comprise a bis-biotin tag through which the polymerase is bound to the biotin-binding protein.

In one class of embodiments, the biotin-binding protein is a tetravalent biotin-binding protein, e.g., streptavidin. In some embodiments, the biotin-binding protein comprises one or more covalent modifications that decrease its calculated net charge relative to a parental biotin-binding protein lacking the covalent modification. In some embodiments, the biotin-binding protein comprises one or more covalently attached sulfonate moieties, e.g., one or more covalently attached 3,4,5-tris(3-sulfopropoxy)benzoyl moieties. In some embodiments, the biotin-binding protein comprises one or more amino acid substitutions that decrease its calculated net charge relative to a parental biotin-binding protein, e.g., one or more amino acid substitutions that replace a positively charged or uncharged residue in the parental biotin-binding protein with a negatively charged residue. In some embodiments, the biotin-binding protein comprises a polyglutamate tag.

The methods can include, after the exposing step, contacting the surface with free biotin-binding protein, e.g., having a calculated net charge of −20 or less at pH 7.4. In some embodiments, the methods include, after the exposing step, determining a nucleotide sequence of the nucleic acid.

Another general class of embodiments provides methods of sequencing a nucleic acid template that include a) providing a reaction mixture comprising the template, a replication initiating moiety that complexes with or is integral to the template, a nucleic acid polymerase capable of replicating at least a portion of the template using the moiety in a template-dependent polymerization reaction, and one or more nucleotides and/or nucleotide analogs, wherein at least one of the template, the replication initiating moiety, and the polymerase is immobilized on a solid support through binding to a biotin-binding protein, which biotin-binding protein has a calculated net charge of −20 or less at pH 7.4; b) subjecting the reaction mixture to a polymerization reaction in which the polymerase replicates at least a portion of the template in a template-dependent manner, whereby the one or more nucleotides and/or nucleotide analogs are incorporated into the resulting nucleic acid; and c) identifying a time sequence of incorporation of the one or more nucleotides and/or nucleotide analogs into the resulting nucleic acid.

In some embodiments, the subjecting and identifying steps are performed in a nanoscale reaction region, e.g., a nanoscale well. The template is optionally a DNA template. The polymerase is optionally a DNA polymerase.

Another general class of embodiments provides methods of making a nucleic acid that include a) providing a reaction mixture comprising: a template, a replication initiating moiety that complexes with or is integral to the template, a nucleic acid polymerase capable of replicating at least a portion of the template using the moiety in a template-dependent polymerase reaction, and one or more nucleotides and/or nucleotide analogs, wherein at least one of the template, the replication initiating moiety, and the polymerase is immobilized on a solid support through binding to a biotin-binding protein, which biotin-binding protein has a calculated net charge of −20 or less at pH 7.4; and b) reacting the mixture such that the polymerase replicates at least a portion of the template in a template-dependent manner, whereby the one or more nucleotides and/or nucleotide analogs are incorporated into the resulting nucleic acid.

In some embodiments, the mixture is reacted in a nanoscale well. The methods can include detecting incorporation of at least one of the nucleotides and/or nucleotide analogs. The template is optionally a DNA template. The polymerase is optionally a DNA polymerase.

One general class of embodiments provides a composition comprising a recombinant streptavidin, which recombinant streptavidin comprises at least one monomer that comprises an amino acid sequence that is at least 70% identical to SEQ ID NO:1 and that comprises one or more mutation selected from the group consisting of an amino acid substitution at position A2, an amino acid substitution at position G3, an amino acid substitution at position T15, an amino acid substitution at position T19, an amino acid substitution at position G21, an amino acid substitution at position A22, an amino acid substitution at position T29, an amino acid substitution at position Y47, an amino acid substitution at position A50, an amino acid substitution at position T53, an amino acid substitution at position N92, an amino acid substitution at position A104, an amino acid substitution at position A106, an amino acid substitution at position T116, and an amino acid substitution at position T118, wherein identification of positions is relative to SEQ ID NO:1.

In one class of embodiments, the at least one monomer comprises one or more mutation selected from the group consisting of an A2D substitution, an A2E substitution, a G3D substitution, a G3E substitution, a T15E substitution, a T15D substitution, a T19E substitution, a T19D substitution, an A22E substitution, an A22D substitution, a Y47D substitution, a Y47E substitution, a T53D substitution, a T53E substitution, an N92E substitution, an N92D substitution, an A104E substitution, an A104D substitution, an A106E substitution, an A106D substitution, a T116D substitution, a T116E substitution, a T118D substitution, and a T118E substitution, wherein identification of positions is relative to SEQ ID NO:1. In some embodiments, the at least one monomer comprises a combination of mutations selected from the group consisting of a) A2D, A22E, T53D, N69D, A104E, and K121E; b) A2D, T15E, A22E, T53D, N69D, A87E, A89D, N92E, A104E, T116D, T118D, and K121E; c) A2D, T53D, and N69D; d) A22E, A104E, and K121E; e) A2D, A22E, T53D, N69D, A87E, N92E, A104E, T118D, and K121E; and f) A2D, T15E, A22E, T53D, N69D, A87E, A89D, N92E, A104E, T116D, T118D, and K121E.

In one class of embodiments, the at least one monomer comprises one or more mutation selected from the group consisting of an A2K substitution, a T15K substitution, a G21K substitution, a T29K substitution, an A50K substitution, an N92K, and a T116K substitution, wherein identification of positions is relative to SEQ ID NO:1. In some embodiments, the at least one monomer comprises a combination of mutations selected from the group consisting of: a) G21K and Y70K; b) A2K, R40K, and A50K; c) A2K, G21K, R40K, A50K, and Y70K; d) A2K, G21K, R40K, A50K, Y70K, R90K, N92K, and T116K; and e) A2K, T15K, G21K, T29K, R40K, A50K, Y70K, R90K, N92K, and T116K.

In one class of embodiments, the at least one monomer comprises one or more mutation selected from the group consisting of an amino acid substitution at position K67, an amino acid substitution at position K108, an amino acid substitution at position K119, and an amino acid substitution at position K121. In some embodiments, the at least one monomer comprises one or more mutation selected from the group consisting of a K67R substitution, a K108R substitution, a K119R substitution, and a K121R substitution.

In some embodiments, the at least one monomer comprises an amino acid sequence that is at least 80% identical to SEQ ID NO:1, e.g., at least 90% identical to SEQ ID NO:1. Optionally, the recombinant streptavidin comprises four monomers that are identical in their amino acid sequence. In some embodiments, the at least one monomer comprises one or more exogenous features at the C-terminal and/or N-terminal region of the monomer, e.g., a poly-glutamic acid tag, a poly-aspartic acid tag, or a poly-lysine tag.

In some embodiments, the recombinant streptavidin comprises one or more covalent modifications that decrease its calculated net charge relative to a parental streptavidin lacking the covalent modification. The recombinant streptavidin is optionally bound to a nucleic acid polymerase, e.g., to a nucleic acid polymerase that is complexed with a nucleic acid. In some embodiments, the recombinant streptavidin is immobilized on a solid support. The composition can be present in a nucleic acid sequencing system, for example, a sequencing system that comprises a nanoscale well. The recombinant streptavidin is optionally immobilized on a surface of the nanoscale well. In some embodiments, the recombinant streptavidin exhibits a $K_d$ for biotin that is no more than 10 times the $K_d$ for biotin exhibited by a parental streptavidin whose four monomers comprise SEQ ID NO:1.

One class of embodiments provides a system for sequencing nucleic acids that comprises a chip comprising a plurality of polymerase enzyme complexes bound thereto, each polymerase enzyme complex individually optically resolvable, each polymerase enzyme complex comprising a polymerase enzyme, a template nucleic acid, and optionally a primer hybridized to the template nucleic acid, wherein the polymerase enzyme complexes are bound to the chip through a recombinant streptavidin as described above; sequencing reagents in contact with the surface comprising reagents for carrying out nucleic acid synthesis including one or more labeled nucleotide analogs; an illumination system for illuminating the polymerase enzyme complexes;

an optical detection system for detecting fluorescence from the labeled nucleotide analogs while they are interacting with the polymerase enzyme complexes; and a computer for analyzing the signals detected by the detection system to determine the sequential addition of nucleotides to a nucleic acid strand complementary to a strand of the template nucleic acid.

One general class of embodiments provides a system for sequencing nucleic acids that includes a chip comprising a plurality of polymerase enzyme complexes bound thereto, each polymerase enzyme complex individually optically resolvable, each polymerase enzyme complex comprising a polymerase enzyme, a template nucleic acid, and optionally a primer hybridized to the template nucleic acid, wherein the polymerase enzyme complexes are bound to the chip through a biotin-binding protein having a calculated net charge of −20 or less at pH 7.4; sequencing reagents in contact with the surface comprising reagents for carrying out nucleic acid synthesis including one or more labeled nucleotide analogs; an illumination system for illuminating the polymerase enzyme complexes; an optical detection system for detecting fluorescence from the labeled nucleotide analogs while they are interacting with the polymerase enzyme complexes; and a computer for analyzing the signals detected by the detection system to determine the sequential addition of nucleotides to a nucleic acid strand complementary to a strand of the template nucleic acid. The chip optionally comprises a plurality of nanoscale reaction regions (e.g., nanoscale wells) that comprise the polymerase enzyme complexes.

Another general class of embodiments provides a system for sequencing nucleic acids that includes a chip comprising a plurality of polymerase enzyme complexes bound thereto, each polymerase enzyme complex individually optically resolvable, each polymerase enzyme complex comprising a polymerase enzyme, a template nucleic acid, and optionally a primer hybridized to the template nucleic acid, wherein the polymerase enzyme complexes are bound to the chip through a modified biotin-binding protein that comprises one or more covalently attached sulfonate moieties; sequencing reagents in contact with the surface comprising reagents for carrying out nucleic acid synthesis including one or more labeled nucleotide analogs; an illumination system for illuminating the polymerase enzyme complexes; an optical detection system for detecting fluorescence from the labeled nucleotide analogs while they are interacting with the polymerase enzyme complexes; and a computer for analyzing the signals detected by the detection system to determine the sequential addition of nucleotides to a nucleic acid strand complementary to a strand of the template nucleic acid. The chip optionally comprises a plurality of nanoscale reaction regions (e.g., nanoscale wells) that comprise the polymerase enzyme complexes.

BRIEF DESCRIPTION OF THE DRAWINGS

FIG. 10A schematically illustrates synthesis of an N-hydroxysuccinimide ester of SG1-SGA. FIG. 10B schematically illustrates reaction of a free primary amino group in streptavidin with an N-hydroxysuccinimide ester of SG1-SGA.

Figure 1A:
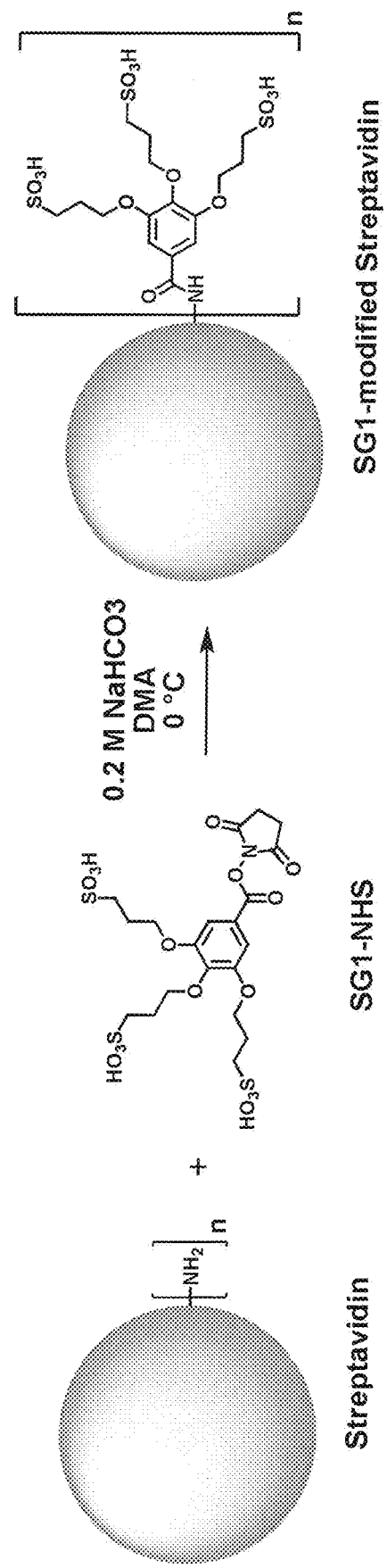
FIG. 1A schematically illustrates reaction of a free primary amino group in streptavidin with an N-hydroxysuccinimide ester of 3,4,5-tris(3-sulfopropoxy)benzoic acid (SG1-NHS).

Schematic figures are not necessarily to scale.

DEFINITIONS

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Note that as used herein and in the appended claims, the singular forms "a," "an," and "the" include plural referents unless the context clearly dictates otherwise. Thus, for example, reference to "a protein" includes a plurality of proteins; reference to "a cell" includes mixtures of cells, and the like.

The term "about" as used herein indicates the value of a given quantity varies by +/−10% of the value, or optionally +/−5% of the value, or in some embodiments, by +/−1% of the value so described.

Where a range of values is provided, it is understood that each intervening value between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. A stated range generally includes one or both limits unless the context clearly dictates otherwise.

The term "nucleic acid" encompasses any physical string of monomer units that can be corresponded to a string of nucleotides, including a polymer of nucleotides (e.g., a typical DNA or RNA polymer), PNAs (peptide nucleic acids), modified oligonucleotides (e.g., oligonucleotides comprising nucleotides that are not typical to biological RNA or DNA, such as 2'-O-methylated oligonucleotides), and the like. A nucleic acid can be e.g., single-stranded or double-stranded. A nucleic acid of the present invention will generally contain phosphodiester bonds, although in some cases, nucleic acid analogs are included that may have alternate backbones, comprising, for example, phosphoramide, phosphorothioate, phosphorodithioate, or other backbones and linkages. The nucleic acid can have other modifications, such as the inclusion of heteroatoms, the attachment of labels, such as dyes, or substitution with functional groups, which will still allow for base pairing and for recognition of the nucleic acid by a polymerase enzyme where the nucleic acid is to be employed as a template.

A "kilobase" or "kb" is a unit used in designating the length of a nucleic acid sequence. 1 kb equals a sequence of 1000 bases or nucleotides. It will be evident that 1 kb can thus also represent a sequence of 1000 base pairs for a double-stranded nucleic acid.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation, biotinylation, or the like. The amino acid residues of the polypeptide can be natural or non-natural and can be unsubstituted, unmodified, substituted or modified.

An "amino acid sequence" is a polymer of amino acid residues (a protein, polypeptide, etc.) or a character string representing an amino acid polymer, depending on context.

Numbering of a given amino acid or nucleotide polymer "corresponds to numbering of" or is "relative to" a selected amino acid polymer or nucleic acid when the position of any given polymer component (amino acid residue, incorporated nucleotide, etc.) is designated by reference to the same residue position in the selected amino acid or nucleotide polymer, rather than by the actual position of the component in the given polymer. Similarly, identification of a given position within a given amino acid or nucleotide polymer is "relative to" a selected amino acid or nucleotide polymer when the position of any given polymer component (amino acid residue, incorporated nucleotide, etc.) is designated by reference to the residue name and position in the selected amino acid or nucleotide polymer, rather than by the actual name and position of the component in the given polymer. Correspondence of positions is typically determined by aligning the relevant amino acid or polynucleotide sequences. For example, residue A15 of partially processed streptavidin (SEQ ID NO:2) is identified as position A2 relative to the core processed streptavidin sequence (SEQ ID NO:1). Amino acid positions herein are generally identified relative to SEQ ID NO:1 unless explicitly indicated otherwise.

A "polymerase" or "nucleic acid polymerase" is an enzyme that synthesizes a polymer of nucleotides. A polymerase can be, e.g., an RNA-directed polymerase that produces a polynucleotide complementary to an RNA template strand using base-pairing interactions, a DNA-directed polymerase that produces a polynucleotide complementary to a DNA template strand using base-pairing interactions, an RNA polymerase that produces an RNA product strand, and/or a DNA polymerase that produces an DNA product strand (e.g., a DNA-directed DNA polymerase, an RNA-directed DNA polymerase, etc.).

The term "recombinant" indicates that the material (e.g., a nucleic acid or a protein) has been artificially or synthetically (non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other procedures; a "recombinant polypeptide" or "recombinant protein" is a polypeptide or protein which is produced by expression of a recombinant nucleic acid.

The terms "bis-biotin," "bis-biotin tag," and "bis-biotin moiety" can be used interchangeably and generally refer to two covalently-linked biotins linked (typically, covalently linked) to a reactant of interest. In certain embodiments, a reactant of interest comprises a sequence that is recognized by a biotin ligase, which catalyzes a covalent linkage between the sequence and a biotin molecule. Such a sequence is generally referred to as a biotin ligase recognition sequence. Each biotin ligase recognition sequence in a reactant of interest can be covalently linked to a biotin moiety, so a reactant having multiple biotin ligase recognition sequences can be covalently linked to multiple biotins. A region of a reactant having one or more biotin ligase recognition sequences is generally referred to as a biotinylation region of the reactant. Thus, for example, a bis-biotin tag can refer to two biotins bound to two biotinylation peptides within a fusion protein reactant.

A variety of additional terms are defined or otherwise characterized herein.

DETAILED DESCRIPTION

Biotin-binding proteins such as streptavidin are commonly used to associate biotinylated molecules of interest with other biotinylated molecules, with the biotinylated surface of a solid support, or the like. Wild type streptavidin exhibits extremely high affinity for biotin, with a $K_d$ of approximately $10^{-14}$ M. However, altering other properties of streptavidin, particularly of surfaces of the streptavidin that can or do contact molecules of interest, the solid support, etc., can improve the performance of streptavidin when used for association or immobilization. Without limitation to any particular mechanism, changing the surface charge of the streptavidin can affect its interactions with the surface of a solid support and/or with a molecule to be immobilized.

For example, introducing additional charges to the surface of streptavidin, particularly additional negative charges, improves the performance of streptavidin used to immobilize nucleic acids, including polymerase/nucleic acid complexes—despite the electrostatic repulsion that would be predicted to occur between the negatively charged nucleic acid and a negatively charged streptavidin. The surface charge of streptavidin can be altered, e.g., by chemical modification and/or mutation, as described in greater detail hereinbelow. Other biotin-binding proteins can be similarly altered to improve their performance.

Biotin-Binding Proteins and Biotin Analogs

The biotin-streptavidin linkage is one of the strongest non-covalent interactions characterized to date. The four streptavidin monomers are arranged as a dimer of dimers. As such, up to four biotin-tagged entities (e.g., proteins, nucleic acids, small molecules, a solid support surface, etc.) can be linked together via interaction of their respective biotin tags with a single streptavidin tetraplex. In some particularly useful embodiments, two biotin-tagged entities are linked together via interaction of a bis-biotin tag on each entity with a single tetravalent streptavidin.

Streptavidin has been cloned and studied extensively. See, for example, Argaraña, et al. (1986) Nucleic Acids Res. 14(4): 1871-1882; Aslan, et al. (2007) Journal of Biotechnology 128:213-225; Aslan, et al. (2005) J. Proc. Natl. Acad. Sci. USA 102(24):8507-8512; Baugh, et al. (2010) Biochemistry 49:4568-4570; Gitlin, et al. (1988) Biochem. J. 256:279-282; Hendrickson, et al. (1989) Proc. Natl. Acad. Sci. USA 86:2190-2194; Hyster, et al. (2012) Science 338: 500-503; Klumb, et al. (1998) Biochemistry 37(21):7657-63; Kurzban, et al. (1991) J. Biol. Chem. 266(22):14470-14477; Matsumoto, et al. (2011) J. Biotechnology 152:37-42; Sano, et al. (1996) Annals of the New York Academy of Sciences 799 (Enzyme Engineering XIII) pp. 383-390; Schmidt, et al. (1994) Journal of Chromatography A 676: 337-345; Srisawat, et al. (2001) RNA 7:632-641; Tahiri-Alaoui, et al. (2002) Nucleic Acids Res. 30(10):e45; Voss, et al. (1997) Protein Engineering 10(8):975-982; and Wilbur, et al. (2004) Bioconjugate Chem. 15:1454-1463, all of which are incorporated herein by reference in their entireties for all purposes. Production of heteromeric biotin-binding proteins that include both active and inactive subunits has been described, e.g., in Fairhead et al. (2014) J. Am. Chem. Soc. 136: 12355-12363 and Howarth et al. (2006) Nat Methods 3: 267-273. The core sequence of a streptavidin monomer is presented as SEQ ID NO:1 in Table 1. In *Streptomyces avidii*, the streptavidin monomer is initially translated as a larger polypeptide from which N- and C-terminal segments that inhibit biotin binding are removed; the sequence of a less processed form of streptavidin is presented as SEQ ID NO:2.

Although described primarily in terms of a streptavidin tetramer bound to biotinylated (or bis-biotinylated) reagents herein, it will be clear to the ordinary practitioner that streptavidin can be replaced with any of various biotin-binding proteins and/or that biotin can be replaced with a biotin analog. As such, recitation of streptavidin and biotin in various embodiments herein is merely exemplary and in no way excludes the use of other biotin- or streptavidin-binding reactants or of other biotin forms or analogs, either instead of or in combination with streptavidin and/or biotin, in the various aspects of the invention described herein, e.g., methods, compositions, systems, and kits.

In general, a biotin-binding protein for use in the invention is one that binds biotin, preferably with high affinity (e.g., affinity comparable to that demonstrated by other known biotin-binding proteins such as streptavidin and the other examples listed herein). Typically, a biotin-binding protein has a $K_d$ of $10^{-7}$ M or less for biotin, preferably $10^{-9}$ M or less or $10^{-10}$ M or less, more preferably $10^{-11}$ M or less, $10^{-12}$ M or less, $10^{-13}$ M or less, $10^{-14}$ M or less, or even $10^{-15}$ M or less. Suitable biotin-binding proteins are well known in the art. Exemplary suitable tetrameric biotin-binding proteins include, but are not limited to, streptavidin, avidin, deglycoslylated avidin (NeutrAvidin), traptavidin, tamavidin, xenavidin, bradavidin, AVR2 (Avidin Related Protein 2), AVR4 (Avidin Related Protein 4), and variants, mutants, derivatives, or homologs thereof; see, e.g., Livnah et al. (1993) "Three-dimensional structures of Avidin and the Avidin-biotin complex" Proceedings of the National Academy of Sciences of the United States of America 90(11): 5076-80, Bayer et al. (1995) "Preparation of deglycosylated egg white avidin" Appl Biochem Biotechnol 53(1):1-9, Marttila et al. (2000) "Recombinant NeutraLite avidin: a non-glycosylated, acidic mutant of chicken avidin that exhibits high affinity for biotin and low non-specific binding properties" FEBS Lett 467(1):31-6, Chivers et al. (2010) "A streptavidin variant with slower biotin dissociation and increased mechanostability" Nat Methods 7(5): 391-393, Chivers et al. (2011) "How the biotin-streptavidin interaction was made even stronger: investigation via crystallography and a chimaeric tetramer" Biochem J. 435(1):55-63, Takakura et al. (2009) "Tamavidins—Novel avidin-like biotin-binding proteins from the Tamogitake mushroom" FEBS Journal 276:1383-1397, Määttä et al. (2009) "Structural and functional characteristics of xenavidin, the first frog avidin from *Xenopus tropicalis*" BMC Structural Biology 9:63, Agrawal et al. (2017) "Structural characterization of core-bradavidin in complex with biotin" PLoS ONE 12(4): e0176086, Helppolainen et al. (2008) "Bradavidin II from *Bradyrhizobium japonicum*: a new avidin-like biotin-binding protein" Biochim Biophys Acta 1784(7-8):1002-10, Hytonen et al. (2005) "Avidin related protein 2 shows unique structural and functional features among the avidin protein family" BMC Biotechnology 5:28, Taskinen et al. (2014) "A novel chimeric avidin with increased thermal stability using DNA shuffling" PLoS One. 2014; 9(3): e92058, and Hytonen et al. (2004) "Chicken Avidin-related Protein 4/5 Shows Superior Thermal Stability when Compared with Avidin while Retaining High Affinity to Biotin" The Journal of Biological Chemistry 279:9337-9343. Exemplary suitable dimeric biotin-binding proteins include, but are not limited to, rhizavidin and variants, mutants, derivatives, or homologs thereof; see, e.g., Helpploainen et al. (2007) Biochem. J. 405: 397-405. U.S. Pat. No. 7,981,632 describes the "strep-tag" peptide, which binds to a modified version of streptavidin, streptactin. A tetrameric biotin-binding protein is optionally tetravalent, having four active biotin binding sites. In other embodiments, a tetrameric biotin-binding protein has three, two, or one active biotin binding site(s) (and one, two, or three inactive sites, respectively). Similarly, a dimeric biotin-binding protein is typically divalent, having two active biotin binding sites, but in other embodiments, a dimeric biotin-binding protein has one active biotin binding site (and one inactive site). Multimeric biotin-binding proteins can be homomeric or heteromeric (e.g., a streptavidin tetramer, or a tetramer comprising three streptavidin subunits and one traptavidin subunit).

Similarly, analogs or modified forms of biotin capable of binding streptavidin, avidin, or another biotin-binding agent can be employed, e.g., singly or in a multi- or bis-tag. A "biotin analog" is a compound that, in a particular application (e.g., in binding to streptavidin, avidin, or the like), functions in a manner similar or analogous to naturally occurring biotin, and does not otherwise denote any particular structure. Suitable biotin analogs include, but are not limited to, a biotin sulfoxide (see, e.g., Garlick and Giese (1990) "Dissociative binding of alpha- and beta-sulphoxides of biotinylamidoethyl-3-(4-hydroxy-3-[125I]iodophenyl) propionamide to avidin" Biochemical Journal 268(3):611-

613), iminobiotin, desthiobiotin (also known as dethiobiotin), oxybiotin, carbobiotin (see, e.g., Wormser et al. (1972) "Synthesis and Growth-Promoting Activity of dl-cis-Hexahydro-4-(4-carboxybutyl)-2-cyclopentimidazolone: Carbobiotin" Journal of Pharmaceutical Sciences 61(7):1168-1170), selenobiotin, carboxybiotin, homobiotin, norbiotin, diaminobiotin, biotin sulfone, epibiotin, 5-hydroxybiotin, 2-thiobiotin, azabiotin, methylated derivatives of biotin (e.g., biotin methyl ester), and/or ketone biotin. For crystal structures of various biotin analogs and modified forms, see, e.g., DeTitta et al. (1980) "Carboxybiotin translocation mechanisms suggested by diffraction studies of biotin and its vitamers" Proc Natl Acad Sci USA. 77(1):333-7 and Stallings and DeTitta (1985) "Crystallographic investigations of biotin and carboxybiotin derivatives" Ann N Y Acad Sci. 447:152-68.

As noted above, singly biotinylated molecules of interest can be linked (to each other, to a biotinylated support, etc.) through binding to streptavidin or another multivalent biotin-binding protein. Even more stable binding can be achieved by including a bis-biotin tag on the molecule of interest and/or on the other molecule or surface. For exemplary suitable bis-biotin moieties, see U.S. patent application publication 2017-0184580, herein incorporated by reference in its entirety for all purposes. Typically, the bis-biotin moiety binds to two biotin binding sites on a single biotin-binding protein. In one class of embodiments, each of two entities (e.g., a solid support surface and a polymerase or a nucleic acid) comprises a bis-biotin moiety that is bound to two biotin binding sites on a single tetravalent biotin-binding protein. In other embodiments, one entity is bound to the biotin-binding protein via a bis-biotin moiety while one or more other entities are each bound via a biotin moiety. In other embodiments, each entity comprises a single biotin moiety. In other embodiments, a biotinylated or bis-biotinylated entity is bound to a biotin-binding protein (monovalent or multivalent) that is linked to another molecule or surface, e.g., through covalent modification (e.g., through a covalent crosslinker or the like).

Chemical Modification of Biotin-Binding Proteins

As described above, altering the charge, particularly the surface charge, of a biotin-binding protein can improve its performance in applications such as association or immobilization. Accordingly, one general class of embodiments provides methods of producing a modified biotin-binding protein by covalently modifying one or more amino acid residues in a parental biotin-binding protein. The resulting modified biotin-binding protein comprises one or more covalent modifications. Typically, these covalent modification(s) change the charge (e.g., the calculated net charge) of the modified biotin-binding protein relative to the parental biotin-binding protein. Preferably, the one or more covalent modifications decrease the calculated net charge of the modified biotin-binding protein relative to the parental biotin-binding protein.

Exemplary biotin-binding proteins suitable for use as parental biotin-binding proteins have been described above, and include, e.g., tetravalent and divalent biotin-binding proteins such as streptavidin, avidin, deglycoslylated avidin (NeutrAvidin), traptavidin, tamavidin, xenavidin, bradavidin, AVR2, AVR4, rhizavidin, and variants, mutants, derivatives, or homologs thereof. In one class of embodiments, the modified biotin-binding protein comprises at least one monomer that comprises an amino acid sequence that is at least 70% identical to SEQ ID NO:1, e.g., at least 80%, at least 85%, at least 90%, at least 95%, at least 97%, or at least 98% identical. In one embodiment, the parental biotin-binding protein comprises four monomers that each comprise an amino acid sequence that is at least 70% identical to SEQ ID NO:1, e.g., at least 80%, at least 85%, at least 90%, at least 95%, at least 97%, or at least 98% identical. The modification strategies described herein can be combined with the mutation strategies detailed below. Thus, in one class of embodiments, the biotin-binding protein comprises one or more amino acid substitutions relative to a parental biotin-binding protein, e.g., one or more amino acid substitutions that decrease its calculated net charge relative to the parental biotin-binding protein, improve biotin binding by the modified protein, introduce additional modification sites, and/or the like. Similarly, the biotin-binding protein can include one or more exogenous feature, e.g., a polyglutamate, polyaspartate, polylysine, or other tag as described below.

The modifications can increase or, preferably, decrease the calculated net charge. For example, the modifications can decrease the net charge of the modified biotin-binding protein relative to the parental biotin-binding protein, e.g., altering the calculated net charge by −4 or less, e.g., −8 or less, −10 or less, −12 or less, −16 or less, −20 or less, −30 or less, −40 or less, −50 or less, −60 or less, −70 or less, or even −80 or less, e.g., at pH 7.4. In some embodiments, the modified biotin-binding protein has a calculated net charge of −20 or less at pH 7.4, e.g., −30 or less, −40 or less, −50 or less, −60 or less, −70 or less, or even −80 or less. In some embodiments, modifications do not alter the calculated net charge but do alter local surface charge, e.g., where a decrease in one region of the protein is balanced by an equivalent increase in another region so the surface charge is altered although the net charge is unchanged.

Essentially any charged group can be added to the parental biotin-binding protein. For example, to decrease the net charge, one or more negatively charged groups (such as, e.g., carboxylic acid groups, sulfonic acid groups, sulfinic acid groups, phosphate groups, phosphinic acid groups, or phosphonic acid groups) can be covalently attached. In one class of embodiments, the one or more covalent modifications comprise one or more covalently attached sulfonate moieties (e.g., three or more, 12 or more, 24 or more, 30 or more, 45 or more, or even 60 or more covalently attached sulfonate moieties). For example, the one or more covalent modifications can comprise one or more covalently attached 3,4,5-tris(3-sulfopropoxy)benzoyl moieties (see, e.g., FIG. 1A), 3,5-disulfobenzoyl moieties (see, e.g., FIG. 9B), or 2-sulfobenzoyl moieties (see, e.g., FIG. 11), e.g., four or more, 10 or more, 15 or more, or even 20 or more covalently attached 3,4,5-tris(3-sulfopropoxy)benzoyl, 3,5-disulfobenzoyl, or 2-sulfobenzoyl moieties. Essentially any uncharged group can similarly be added to the parental biotin-binding protein. Note that where the biotin-binding protein is multimeric, the total number of covalently attached moieties (e.g., 45 or more sulfonate moieties on a tetravalent biotin-binding protein) can be equally or unequally distributed between the monomers, as desired or convenient. The number of covalently attached moieties per protein can also be an average determined for a population of the protein.

The net charge of the resulting modified protein can be experimentally determined as known in the art. For example, relative net charge can be assessed, e.g., by measuring retention time on an ion exchange column. The net charge can also be calculated at a desired pH, e.g., given the known amino acid sequence of the protein, modifications employed, and average pKa's of various ionizable groups. Calculated net charge at pH 7.4 can be conveniently determined by assuming a charge of +1 for each arginine side chain, lysine side chain, and free N-terminal amino group and a charge of −1 for each aspartate side chain, glutamate side chain, and C-terminal carboxylate group. Histidine's side chain carries little positive charge on average at pH 7.4 and so is counted as having zero charge. A sulfonate group contributes a charge of −1. Charges of other ionizable groups can be readily determined by one of skill (e.g., −2 for phosphate, etc.). The calculated net charge of SEQ ID NO:1 would thus be −1 (four arginines, four lysines, the N-terminal amine, four aspartates, five glutamates, and the C-terminal carboxylate: +4+4+1−4−5−1=−1); the calculated net charge of a streptavidin tetramer including four copies of SEQ ID NO:1 would be −4.

Covalent linkage of moieties to proteins is well known in the art. The reactive groups on various amino acids can be used to provide specific sites of attachment, e.g., for a charged moiety. Reactive groups for the attachment of moieties to the protein include amine groups on lysine or arginine, the thiol group on cysteine, the carboxylic acid group on aspartic acid or glutamic acid, the hydroxyl group on serine, threonine, or tyrosine, and the indole group on tryptophan, as well as free N-terminal amine and C-terminal carboxylate groups. In some cases, an available protein will have appropriate residues for connection of the moieties. In other cases, the appropriate residues can be engineered into the protein. Using genetic engineering to produce a desired protein having various amino acids removed or added is a common and well understood practice.

The different reactivity of different groups on the protein can be used to direct specific moieties to different attachment points on the protein. For example, a negatively charged moiety can be attached to a lysine at one desired attachment point, and another moiety (e.g., a different negatively charged group, a fluorescent moiety, etc.) can be connected to a specific cysteine at a second attachment point. In some cases, the same type of residue will have different reactivity due to where it resides on the protein, allowing selective attachment. For example, a protein may have three lysine moieties where each has a different reactivity. Attachment can be carried out such that only the most reactive lysine is modified, or alternatively, attachment can be carried out by protecting the two most reactive lysines, then reacting the moiety of interest with the third, least reactive lysine. In some cases, all available residues of the same type can be modified.

There are many types of chemical reactions that can be used to react with specific amino acid residues on proteins. For example, coupling through the cysteine thiol can be accomplished using a reaction with maleimide. Cysteine groups can also be coupled with allylic halides, phenylmethyl halides, alkyl halides, or alpha-halo carbonyl groups. Amine groups can be coupled to activated carboxylates or activated sulfonic acids. Amine or carboxylate functionality on the protein can be used to produce amide linkages. Linkages containing nitrogen double bonds such as oxime or hydrazones can be used. Highly selective linkages can be formed using cycloaddition chemistry such as the Huisgen 1,3-dipolar azide-alkyne cycloaddition. See e.g. Kalia and Raines (2010) "Advances in Bioconjugation" Curr Org Chem. 14(2): 138-147, Besanceney-Webler et al. (2011) "Increasing the Efficacy of Bioorthogonal Click Reactions for Bioconjugation" Angew. Chem. Int. Ed. 50:8051-8056, and Di Marco et al. (2010) "Overview of the main methods used to combine proteins with nanosystems: absorption, bioconjugation, and encapsulation" International Journal of Nanomedicine 5:37-49.

The moieties can be attached to the protein through unnatural amino acids that are introduced into the protein, allowing for specific attachment chemistry. See, for example, the work of Peter Schultz, e.g. Noren et al., "A general method for site-specific incorporation of unnatural amino acids into proteins", Science, 244:182-188, 1989, and Ellman et al. "Biosynthetic method for introducing unnatural amino acids site-specifically into proteins", Methods in Enzymology, Volume 202, 1991, Pages 301-336.

Many other methods of chemically modifying proteins are known in the art. See e.g. "Chemical modification of proteins at cysteine: opportunities in chemistry and biology" Chalker J M, Bernardes G J, Lin Y A, Davis B G, Chem Asian J. 2009 May 4; 4(5):630-40, "Chemoselective ligation and modification strategies for peptides and proteins" Hackenberger C P, Schwarzer D. Angew Chem Int Ed Engl. 2008; 47(52):10030-74, "Chemoselective modification of proteins: hitting the target", Carrico I S, Chem Soc Rev. 2008 July; 37(7):1423-31, "Modification of tryptophan and tryptophan residues in proteins by reactive nitrogen species", Yamakura F, Ikeda K, Nitric Oxide. 2006 March; 14(2):152-61, Chemical modification of proteins, Came A F, Methods Mol Biol. 1994; 32:311-20, Selective chemical modification of proteins, Shaw E, Physiol Rev. 1970 April; 50(2):244-96, and "Chemical reagents for protein modification" By Roger L. Lundblad, CRC Press, 2004. Reactions for attachment of functional groups to proteins and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:
(a) carboxyl groups and derivatives thereof including, but not limited to activated esters, e.g., N-hydroxysuccinimide esters, N-hydroxyphthalimide, N-hydroxybenztriazole esters, acid halides, acyl imidazoles, thioesters, p-nitrophenyl esters, alkyl, alkenyl, alkynyl and aromatic esters, activating groups used in peptide synthesis and acid halides;
(b) hydroxyl groups, which can be converted to esters, sulfonates, phosphoramidates, ethers, aldehydes, etc.
(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups, which are capable of participating in Diels-Alder reactions such as, for example, maleimido groups;
(e) aldehyde or ketone groups, allowing derivatization via formation of carbonyl derivatives, e.g., imines, hydrazones, semicarbazones or oximes, or via such mechanisms as Grignard addition or alkyllithium addition;
(f) sulfonyl halide groups for reaction with amines, for example, to form sulfonamides;
(g) thiol groups, which can be converted to disulfides or reacted with acyl halides, for example;
(h) amine or sulfhydryl groups, which can be, for example, acylated, alkylated or oxidized;
(i) alkenes, which can undergo, for example, cycloadditions, acylation, Michael addition, etc.; and
(j) epoxides, which can react with, for example, amines and hydroxyl compounds.

Figure 1B:
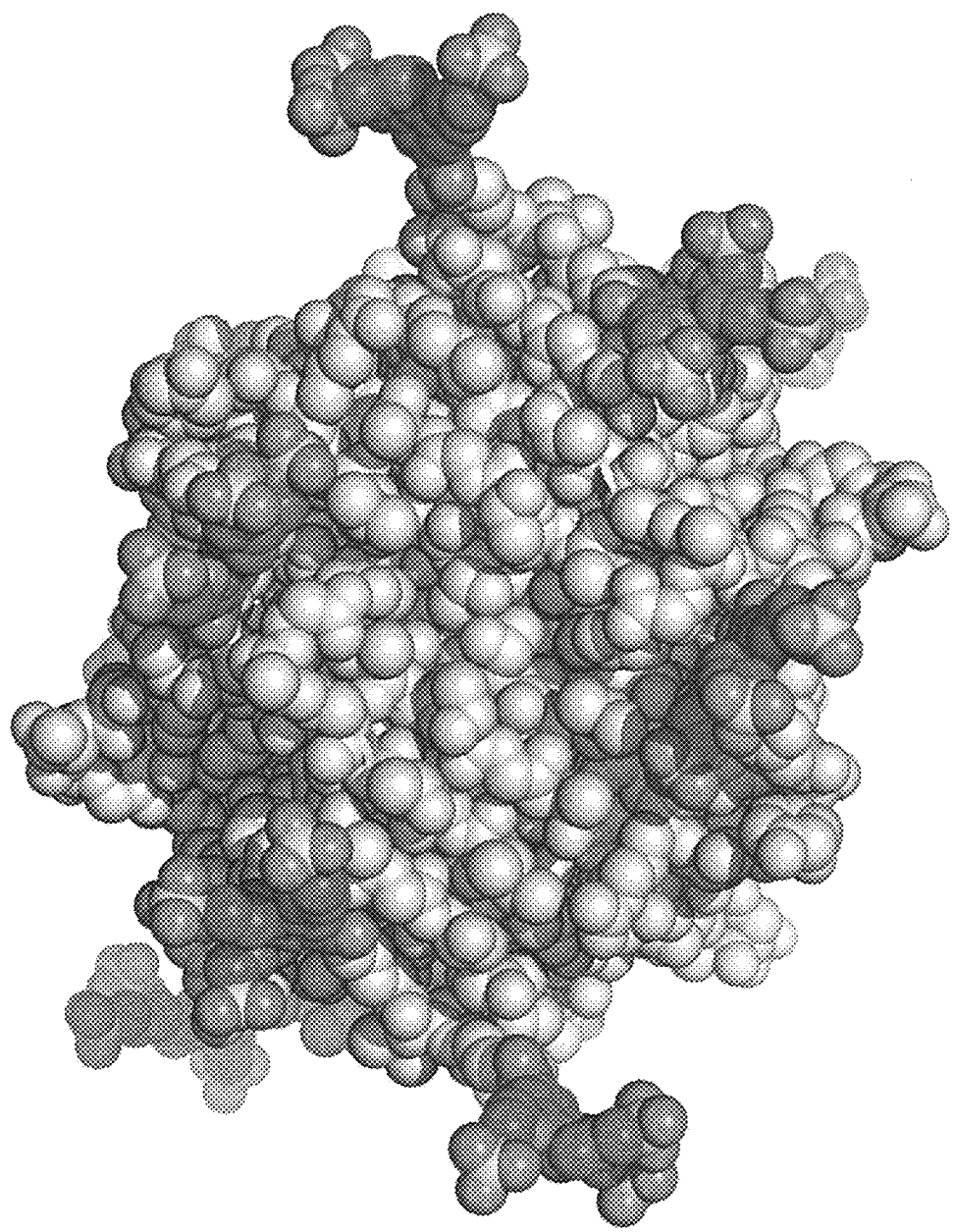
FIG. 1B shows a model of streptavidin (gray) in which lysine residues have been modified with SG1 (darker gray).
Figure 2:
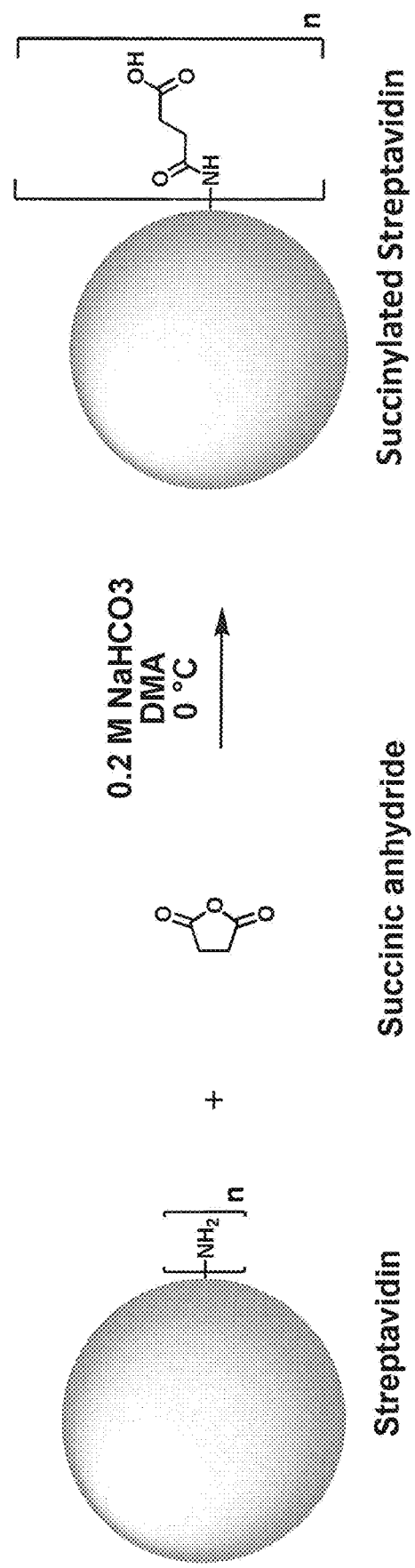
FIG. 2 schematically illustrates reaction of a free primary amino group in streptavidin with succinic anhydride.
Figure 11:
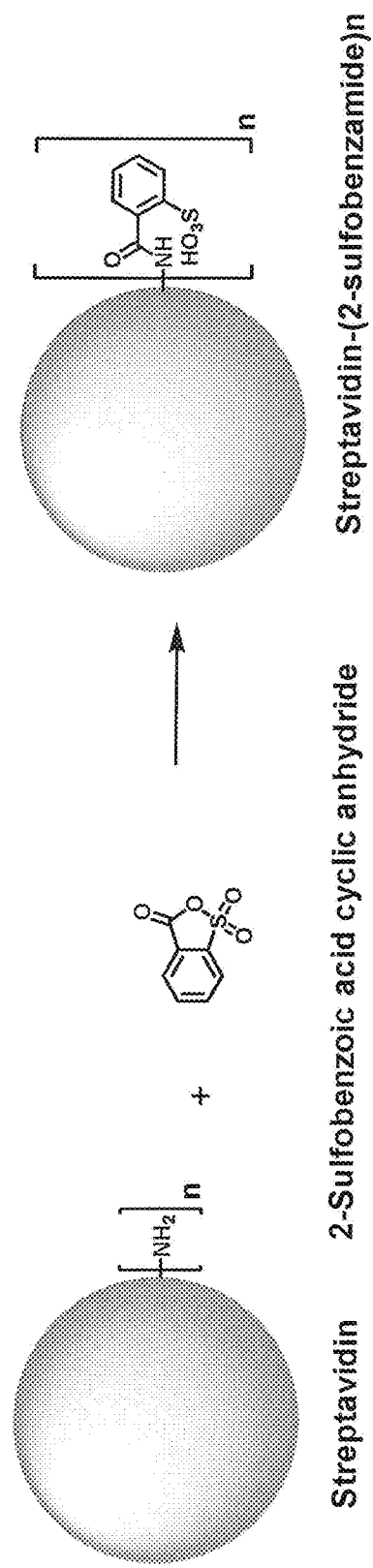
FIG. 11 schematically illustrates reaction of a free primary amino group in streptavidin with 2-sulfobenzoic acid cyclic anhydride.

Covalent modification can alter (e.g., increase or decrease) a protein's charge in various ways. For example, reaction of a positively charged group on the protein with an uncharged group will decrease the net charge. Reaction of a positively charged group on the protein to introduce a negatively charged covalent modification will decrease the net charge to a greater degree. Accordingly, in one class of embodiments, one or more positively charged residues in the parental biotin-binding protein are covalently modified, e.g., one or more lysine residues and/or free N-terminal amines. For example, lysine side chains and/or free N-terminal amines can be reacted with an N-hydroxysuccinimide ester of 3,4,5-tris(3-sulfopropoxy)benzoic acid (SG1-NHS). Reaction of a free primary amino group (e.g., on a lysine side chain or free N-terminus) with SG1-NHS is schematically illustrated in FIG. 1A. FIG. 1B shows a model of streptavidin in which lysine residues have been modified with SG1. While modification of only a single amino group is shown in FIG. 1A for clarity, it will be understood that multiple amino groups (per monomer and/or in different monomers) of the streptavidin can be modified in a single reaction. From one to all of the available primary amino groups can be modified. Each lysine or N-terminal amine (produced, e.g., by removal of an N-formyl methionine, protease removal of an N-terminal tag, etc.) that is modified with SG1 results in a −4 change in calculated net charge at pH 7.4. Modification of all available primary amines in a streptavidin tetramer including four copies of SEQ ID NO:1 with SG1 would thus change the calculated net charge at pH 7.4 by −80 (four lysines and one N-terminal amine per monomer×four monomers×−4 per SG1-modified amine). As another example, primary amino groups in lysine side chains and/or N-termini can be reacted with succinic anhydride, as shown in FIG. 2. (While tyrosine, histidine, cysteine, serine, and threonine side chains also react with succinic anhydride, these modifications are not stable at high pH.) Again, from one to all of the available primary amino groups can be modified. Each primary amine that is succinylated results in a −2 change in calculated net charge at pH 7.4. Modification of all available primary amines in a streptavidin tetramer including four copies of SEQ ID NO:1 with succinic anhydride would change the calculated net charge at pH 7.4 by −40. As another example, primary amino groups in lysine side chains and/or free N-terminal amines of streptavidin can be reacted with an N-hydroxysuccinimide ester of 3,5-disulfobenzoic acid, as schematically illustrated in FIG. 9B. As another example, primary amino groups in lysine side chains and/or free N-terminal amines of streptavidin can be reacted with an N-hydroxysuccinimide ester of SG1-SGA (where SGA is 4-(2-aminoethoxy)-3,5-bis(3-sulfopropoxy)benzoic acid), as schematically illustrated in FIG. 10B. As yet another example, primary amino groups in lysine side chains and/or free N-terminal amines of streptavidin can be reacted with 2-sulfobenzoic acid cyclic anhydride (CAS Number 81-08-3), as schematically illustrated in FIG. 11.

Figure 3:
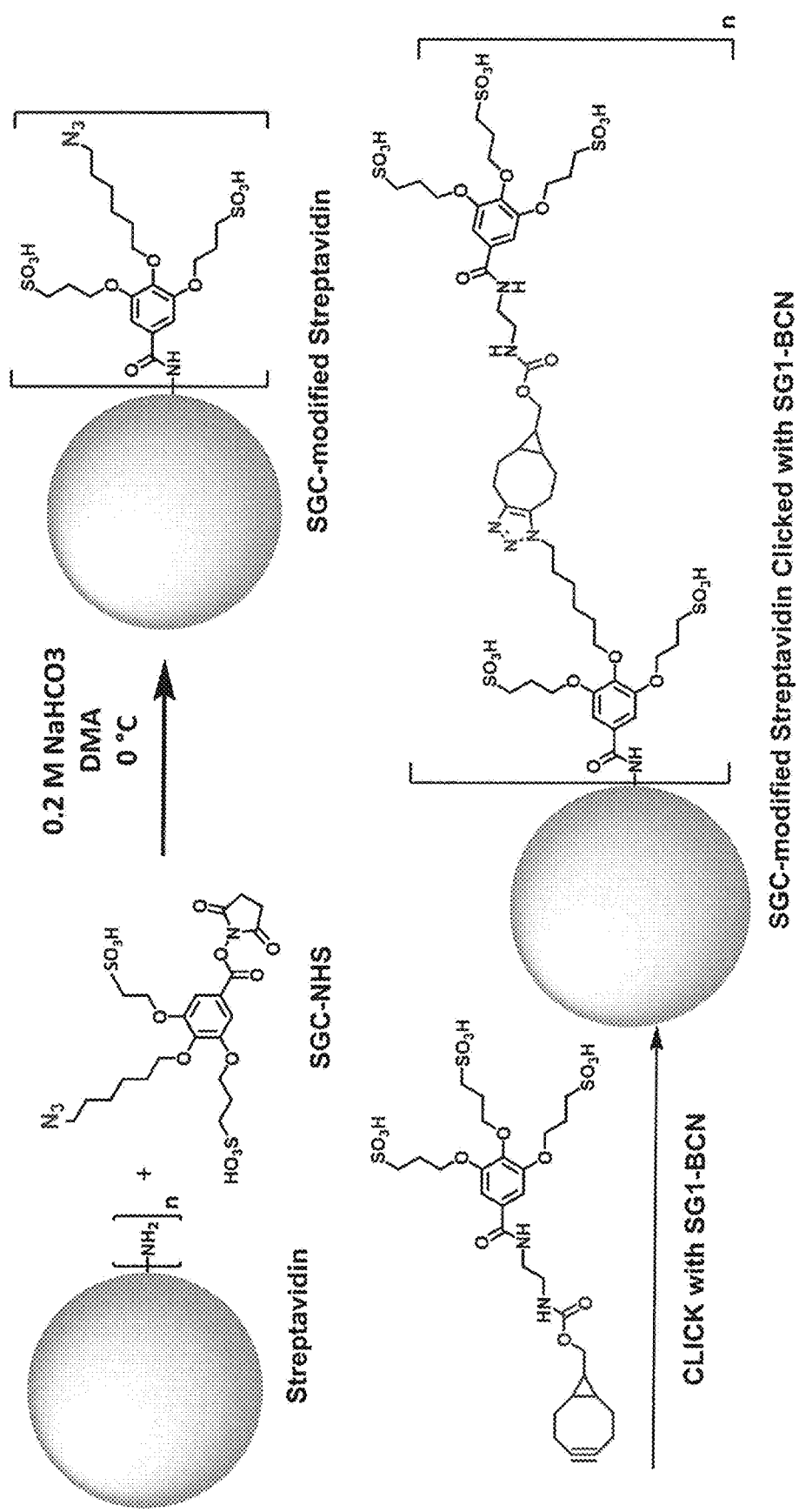
FIG. 3 schematically illustrates two step modification of a free primary amino group in streptavidin by reaction first with an N-hydroxysuccinimide ester of 4-(6-azidohexyloxy)-3,5-bis(3-sulfopropoxy)benzoic acid (SGC-NHS) and then with SG1-BCN.

Covalent modification can be accomplished in multiple steps if desired. For example, primary amino groups in lysine side chains and/or N-termini can be reacted with an N-hydroxysuccinimide ester of 4-(6-azidohexyloxy)-3,5-bis(3-sulfopropoxy)benzoic acid (SGC-NHS) to produce SGC-modified proteins, e.g., SGC-modified streptavidin as shown in FIG. 3. The SGC group includes a clickable azide group. The SGC-modified protein can thus be subjected to a very efficient click reaction modification (Cu-catalyzed or Cu-free) with an acetylene modifier in a second step, to attach any of a variety of desired groups. In the example shown in FIG. 3, the second step clicks an SG1-BCN group to the SGC group; the resulting product has five sulfonate groups at each modified position, resulting in a −6 change in calculated net charge at pH 7.4 per modification. Modification of all available primary amines in a streptavidin tetramer including four copies of SEQ ID NO:1 with SGC-BCN-SG1 would change the calculated net charge at pH 7.4 by −120. Again, from one to all of the available primary amino groups can be modified. Additional information on "click" chemistry is readily available in the art; see, e.g., Kalia and Raines (2010) "Advances in Bioconjugation" Curr Org Chem. 14(2): 138-147 and Besanceney-Webler et al. (2011) "Increasing the Efficacy of Bioorthogonal Click Reactions for Bioconjugation" Angew. Chem. Int. Ed. 50:8051-8056.

Figure 5:
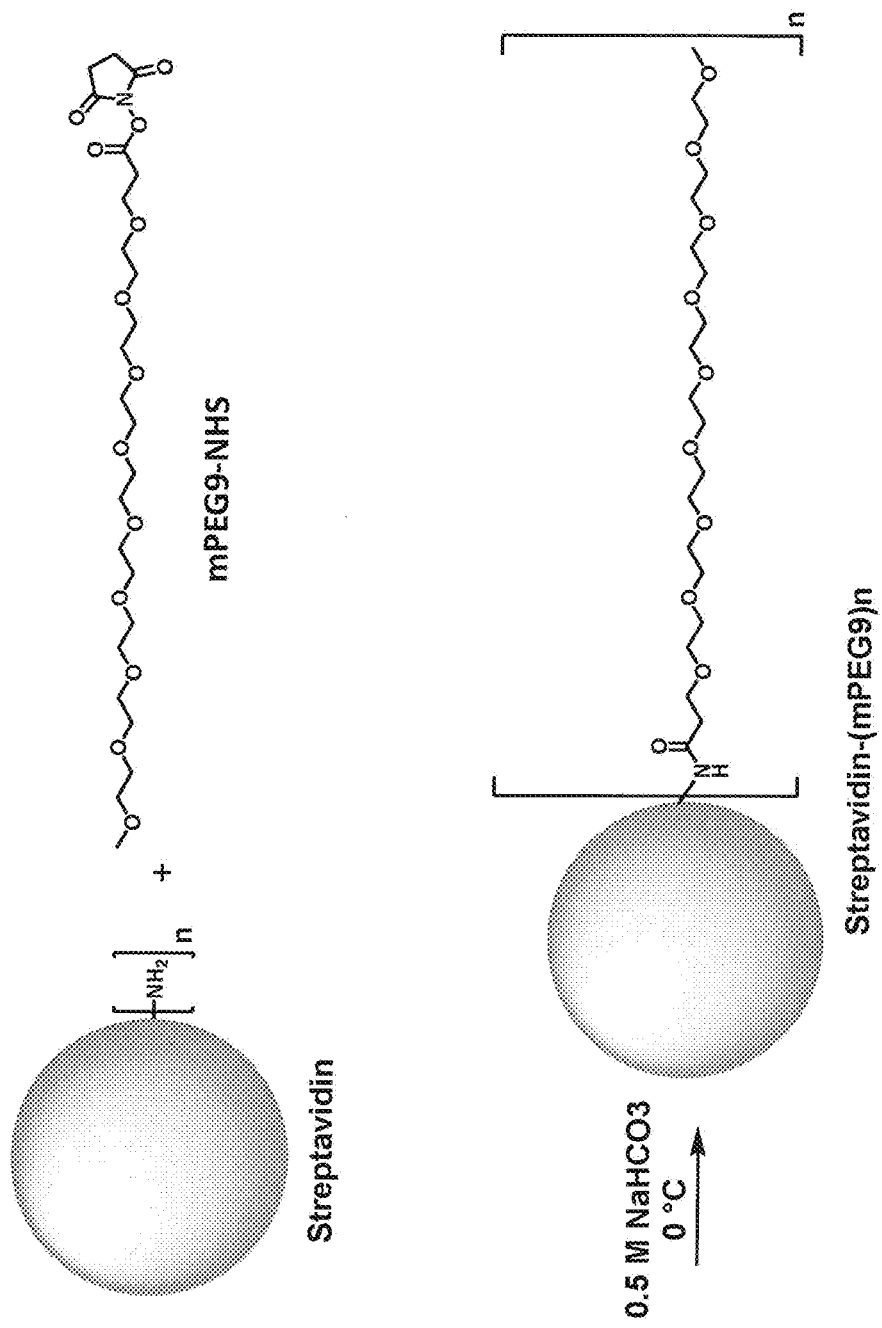
FIG. 5 schematically illustrates reaction of a free primary amino group in streptavidin with an N-hydroxysuccinimide ester of methoxyPEG9 (mPEG9).
Figure 6:
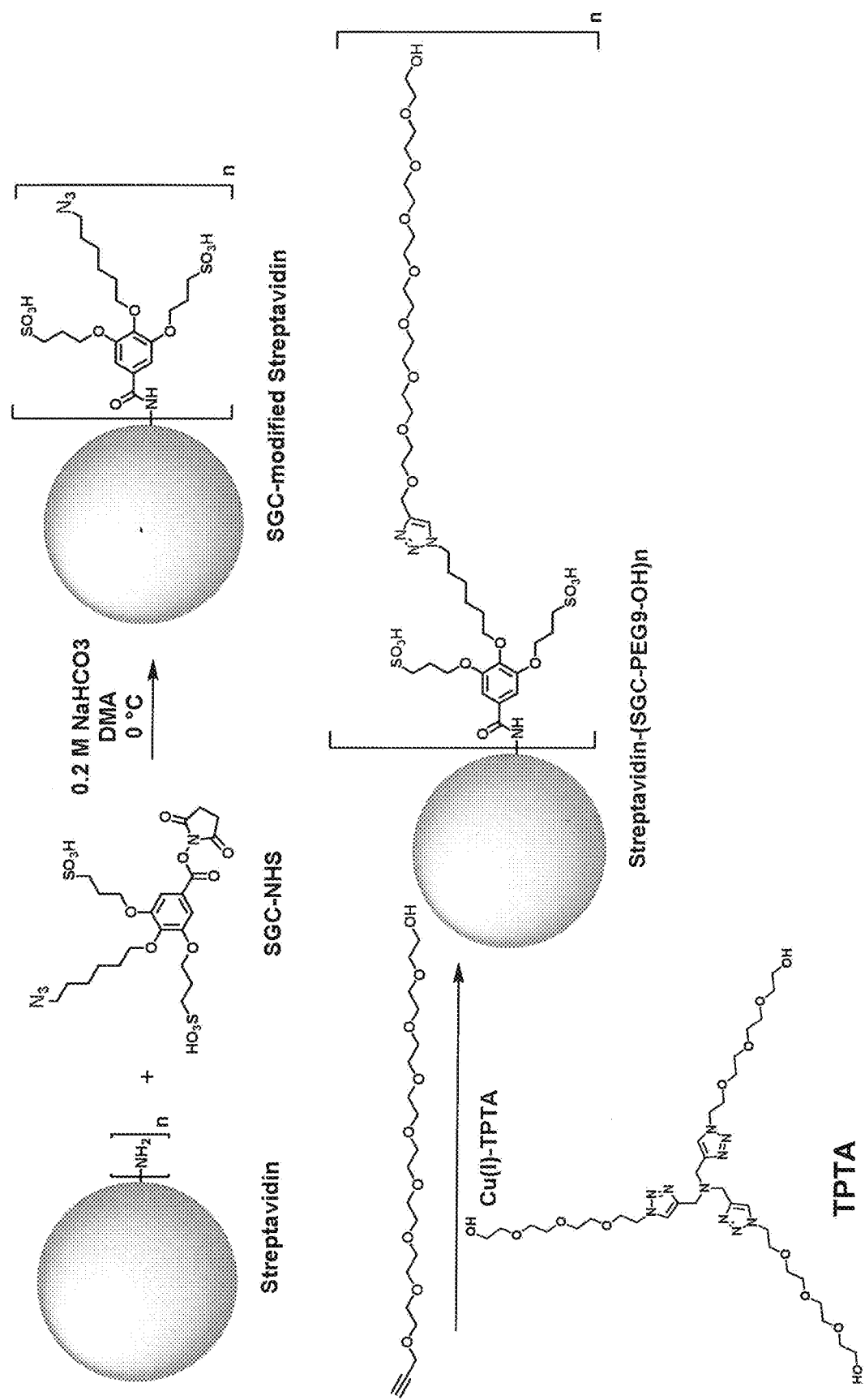
FIG. 6 schematically illustrates two step modification of a free primary amino group in streptavidin by reaction first with SGC-NHS and then with propargyl-PEG9-OH.
Figure 7:
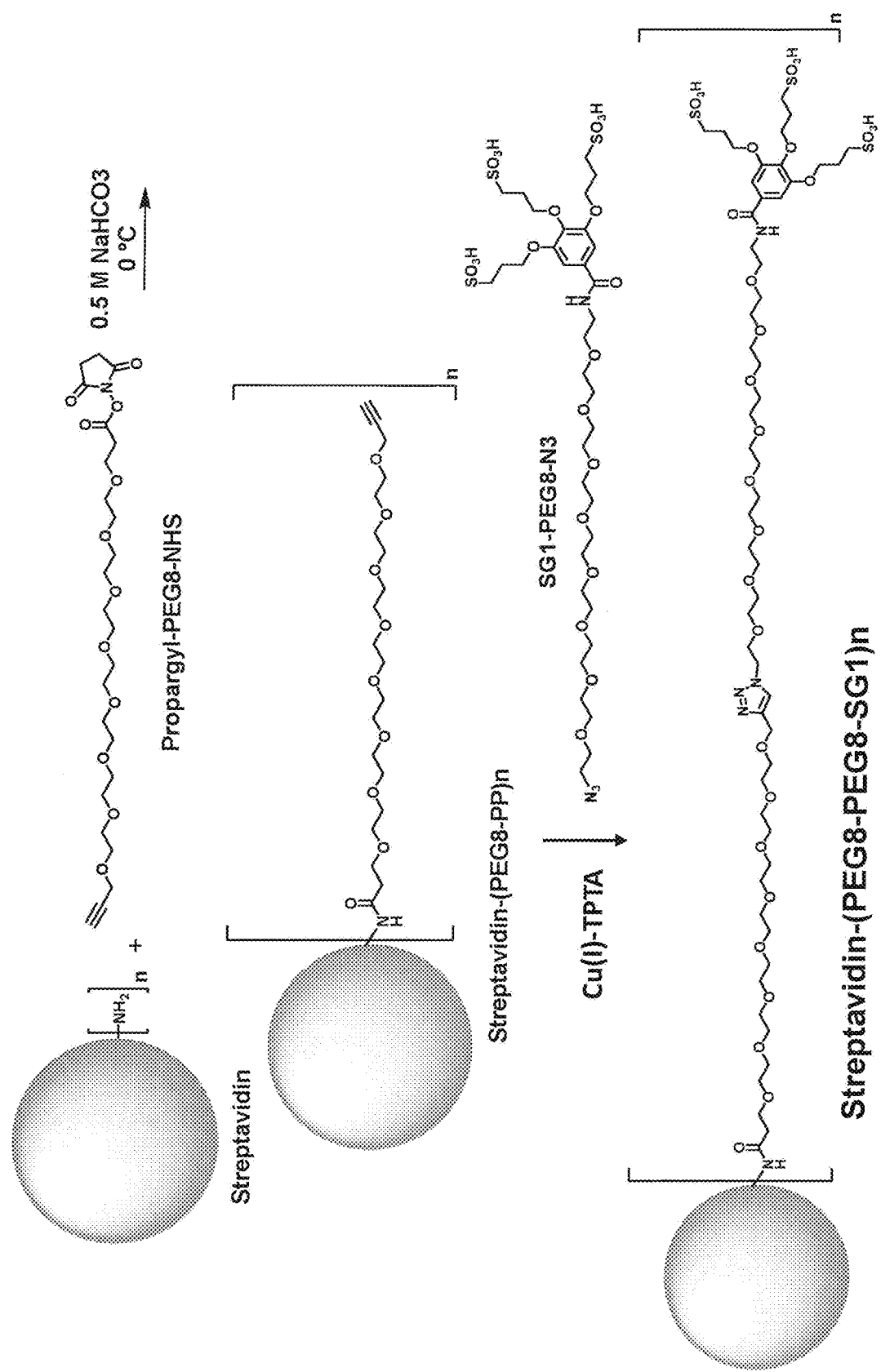
FIG. 7 schematically illustrates two step modification of a free primary amino group in streptavidin by reaction first with propargyl-PEG8-NHS and then with SG1-PEG8-N3.
Figure 8:
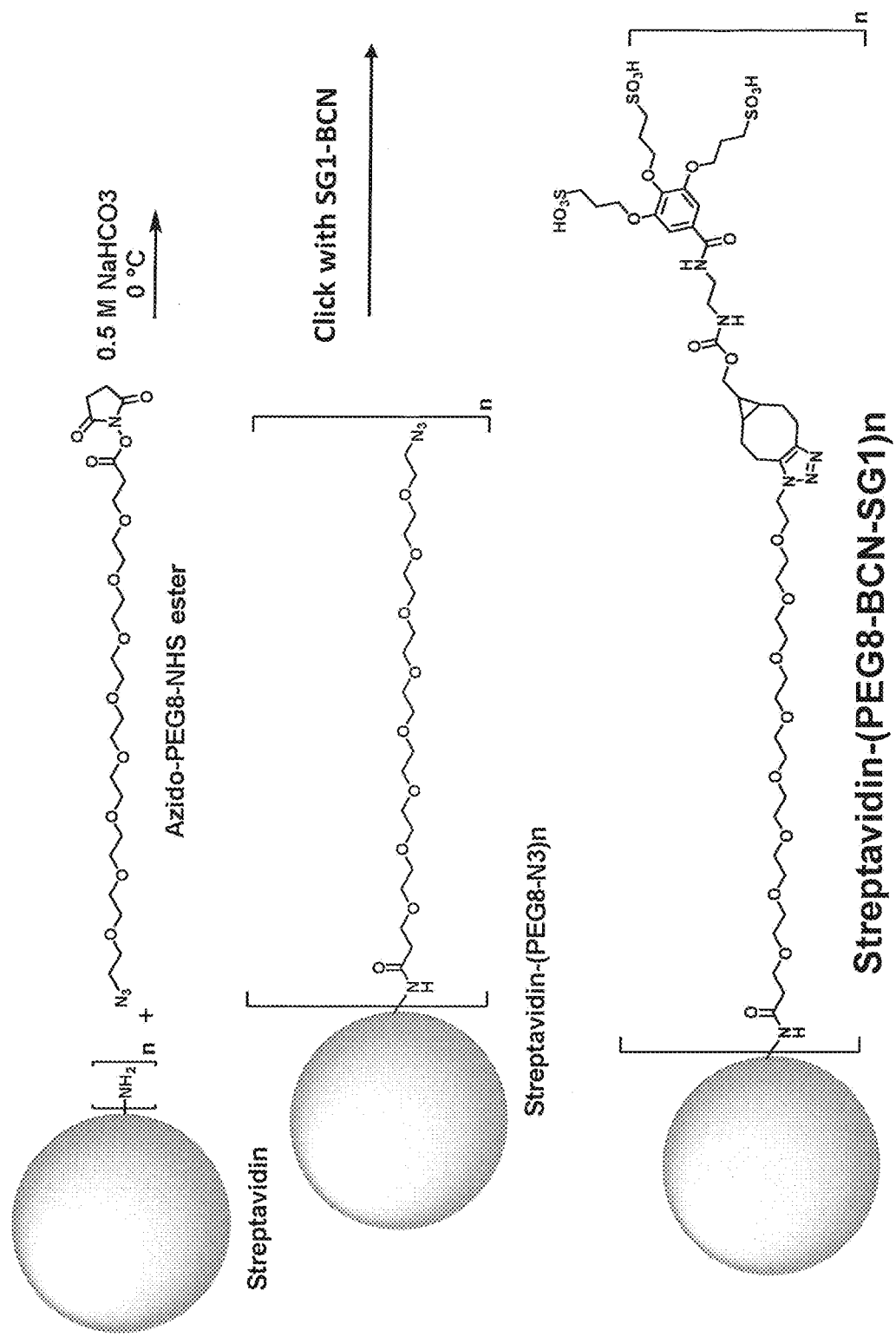
FIG. 8 schematically illustrates two step modification of a free primary amino group in streptavidin by reaction first with azido-PEG8-NHS and then with BCN-SG1.

In some embodiments, the biotin-binding protein is covalently modified with a moiety that includes polyethylene glycol (PEG) or another hydrophilic group, e.g., a flexible hydrophilic linker. Suitable hydrophilic linker groups include, but are not limited to, PEGs, oligopeptides, and oligomers of glycine, beta-alanine, 4-aminobutyric acid, (2-aminoethoxy)acetic acid, 5-aminopentanoic acid, and 6-aminohexanoic acid, optionally including 1-50 monomer units, e.g., 2-30 or 5-10. Such moieties can, but need not, include a charged group, e.g., one or more negatively charged groups. In one class of embodiments, the biotin-binding protein is covalently modified with a PEG moiety, e.g., a sulfonated PEG moiety. The PEG optionally includes 1-50 monomer units, e.g., 2-30 or 5-10. For example, primary amino groups in lysine side chains and/or free N-terminal amines of streptavidin can be reacted with an N-hydroxysuccinimide ester of a methoxyPEG, e.g., mPEG9-NHS as schematically illustrated in FIG. 5. Again, from one to all of the available primary amino groups can be modified. Each primary amine that is mPEGylated results in a −1 change in calculated net charge at pH 7.4. Modification of all available primary amines in a streptavidin tetramer including four copies of SEQ ID NO:1 with mPEG9 would change the calculated net charge at pH 7.4 by −20. As another example, free primary amino groups in streptavidin can be modified with SGC and then subjected to a click reaction modification with a propargyl-PEG-alcohol, e.g., propargyl-PEGS-OH as schematically illustrated in FIG. 6. As another example, free primary amino groups in streptavidin can be reacted with an N-hydroxysuccinimide ester of a propargyl-PEG (e.g., propargyl-PEG8-NHS as schematically illustrated in FIG. 7); the propargyl-PEG-modified streptavidin can then be subjected to a click reaction modification with an azido-PEG (e.g., SG1-PEG8-N3 as schematically illustrated in FIG. 7). As yet another example, free primary amino groups in streptavidin can be reacted with an N-hydroxysuccinimide ester of an azido-PEG (e.g., azido-PEG8-NHS as schematically illustrated in FIG. 8); the resulting azido-PEG-modified streptavidin can then be subjected to a click reaction modification with an acetylene modifier, e.g., BCN-SG1 as schematically illustrated in FIG. 8.

Modified proteins can be isolated from unmodified (or less completely modified) proteins using purification techniques known in the art. For example, a biotin-binding protein whose net charge has been decreased by covalent addition of negatively charged groups can readily be separated from the parental protein using anion exchange chromatography. Similarly, such proteins having a desired degree of modification (or range thereof) can be isolated using anion exchange chromatography.

Modification can be accomplished without interfering with biotin binding activity or with minimal interference. Accordingly, in some embodiments, the modified biotin-binding protein exhibits a $K_d$ for biotin (or an analog) that is no more than 100 times or no more than 10 times the $K_d$ exhibited by the parental protein that was modified, under equivalent reaction conditions. For example, a modified streptavidin produced by reaction of a parental streptavidin whose four monomers comprise SEQ ID NO:1 can exhibit a $K_d$ for biotin (or an analog) that is no more than 100 times or no more than 10 times the $K_d$ exhibited by the parental streptavidin.

Modified biotin-binding proteins produced by the methods are also a feature of the invention. Accordingly, one class of embodiments provides a composition comprising a modified biotin-binding protein that comprises one or more covalently attached sulfonic acid groups (e.g., methylsulfonic acid groups), carboxylic acid groups (e.g., other than the carboxylates present on glutamate residues, aspartate residues, and the C-terminus in the primary structure of the protein), sulfinic acid groups, phosphate groups, phosphinic acid groups, phosphonic acid groups, and/or other negatively charged groups. Optionally, the biotin-binding protein is a tetravalent or divalent biotin-binding protein, e.g., streptavidin, avidin, deglycoslylated avidin (NeutrAvidin), traptavidin, tamavidin, xenavidin, bradavidin, AVR2, AVR4, rhizavidin, and variants, mutants, derivatives, or homologs thereof. In one class of embodiments, the modified biotin-binding protein comprises at least one monomer that comprises an amino acid sequence that is at least 70% identical to SEQ ID NO:1, e.g., at least 80%, at least 85%, at least 90%, at least 95%, at least 97%, or at least 98% identical. In one embodiment, the parental biotin-binding protein comprises four monomers that each comprise an amino acid sequence that is at least 70% identical to SEQ ID NO:1, e.g., at least 80%, at least 85%, at least 90%, at least 95%, at least 97%, or at least 98% identical.

In one class of embodiments, the modified biotin-binding protein comprises one or more covalently attached sulfonate moieties, e.g., three or more, 12 or more, 24 or more, 30 or more, 45 or more, 50 or more, or even 60 or more covalently attached sulfonate moieties. For example, the biotin-binding protein can comprise one or more covalently attached 3,4,5-tris(3-sulfopropoxy)benzoyl (SG1) moieties, e.g., four or more, 10 or more, 15 or more, 16 or more, 17 or more, 18 or more, 19 or more, or even 20 or more covalently attached 3,4,5-tris(3-sulfopropoxy)benzoyl moieties. Note that where the biotin-binding protein is multimeric, the total number of covalently attached moieties (e.g., 45 or more sulfonate moieties on a tetravalent biotin-binding protein) can be equally or unequally distributed between the monomers, as desired or convenient. The number of covalently attached moieties per protein can also be an average determined for a population of the protein.

In some embodiments, the modified biotin-binding protein has a calculated net charge of −20 or less at pH 7.4, e.g., −30 or less, −40 or less, −50 or less, −60 or less, −70 or less, or even −80 or less.

The modification strategies described herein can be combined with the mutation strategies detailed below. Thus, in one class of embodiments, the biotin-binding protein comprises one or more amino acid substitutions relative to a parental biotin-binding protein, e.g., one or more amino acid substitutions that decrease its calculated net charge relative to the parental biotin-binding protein, improve biotin binding by the modified protein, introduce additional modification sites, and/or the like. Similarly, the biotin-binding protein can include one or more exogenous feature, e.g., a polyglutamate, polyaspartate, polylysine, or other tag as described below.

The modified biotin-binding protein can be employed for essentially any desired application. For example, the biotin-binding protein can be used to immobilize a nucleic acid, e.g., a biotinylated nucleic acid or a complex comprising the nucleic acid. In one exemplary class of embodiments, the biotin-binding protein is bound to a nucleic acid polymerase e.g., a biotinylated (e.g., bis-biotinylated) polymerase. Optionally, the nucleic acid polymerase is complexed with a nucleic acid. For example, the biotin-binding protein can be bound to a DNA polymerase that is complexed with a DNA template. The biotin-binding protein is optionally immobilized on a solid support, e.g., whose surface is coated in biotin (e.g., bis-biotin). In one class of embodiments particularly useful for single molecule applications, the biotin-binding protein is immobilized on the base of a nanoscale well, e.g., a zero mode waveguide (ZMW). Optionally, the composition is present in a nucleic acid sequencing system, e.g., a DNA sequencing system as described below.

Mutation of Biotin-Binding Proteins

As detailed above, protein net charge can be altered by covalent modification. Alternatively or additionally, the charge of a biotin-binding protein can be altered by mutagenesis of the protein. As a few examples, the net charge of a biotin-binding protein can be decreased by substituting a negatively charged residue for an uncharged residue or by substituting an uncharged or negatively charged residue for a positively charged residue. Mutagenesis can also be employed to introduce additional sites for covalent modification and/or to remove undesired sites. Residues selected for mutation are typically surface exposed residues. Residues required for activity, e.g., for high affinity biotin binding, can be avoided unless modification of the activity is desired.

Structural data for a biotin-binding protein can be used to conveniently identify amino acid residues as candidates for mutagenesis to create recombinant biotin-binding proteins, for example, surface residues not within the biotin binding site. The three-dimensional structures of a large number of biotin-binding proteins have been determined by x-ray crystallography and nuclear magnetic resonance (NMR) spectroscopy, including structures with bound biotin or biotin analogs. Many such structures are freely available for download from the Protein Data Bank, at www (dot) rcsb (dot) org/pdb. Structures, along with domain and homology information, are also freely available for search and download from the National Center for Biotechnology Information's Molecular Modeling DataBase, at www (dot) ncbi (dot) nlm (dot) nih (dot) gov/Structure/MMDB/mmdb (dot) shtml. For example, the structure of streptavidin complexed with biotin is available; see, e.g., Weber et al. (1989) "Structural origins of high-affinity biotin binding to streptavidin" Science 243: 85-88 and corresponding Protein Data Bank entry PDBID 1STP. The structures of additional biotin-binding proteins or complexes can be modeled, for example, based on homology of the proteins with biotin-binding proteins whose structures have already been determined. Alternatively, the structure of a given biotin-binding protein, optionally complexed with biotin or an analog, or the like, can be determined.

Techniques for crystal structure determination are well known. See, for example, McPherson (1999) *Crystallization of Biological Macromolecules* Cold Spring Harbor Laboratory; Bergfors (1999) *Protein Crystallization* International University Line; Mullin (1993) *Crystallization* Butterwoth-Heinemann; Stout and Jensen (1989) *X-ray structure determination: a practical guide, 2nd Edition* Wiley Publishers, New York; Ladd and Palmer (1993) *Structure determination by X-ray crystallography*, 3rd Edition Plenum Press, NewYork; Blundell and Johnson (1976) *Protein Crystallography* Academic Press, New York; Glusker and Trueblood (1985) *Crystal structure analysis: A primer*, 2nd Ed. Oxford University Press, NewYork; *International Tables for Crystallography, Vol. F. Crystallography of Biological Macromolecules*; McPherson (2002) *Introduction to Macromolecular Crystallography* Wiley-Liss; McRee and David (1999) *Practical Protein Crystallography, Second Edition* Academic Press; Drenth (1999) *Principles of Protein X-Ray Crystallography* (Springer Advanced Texts in Chemistry) Springer-Verlag; Fanchon and Hendrickson (1991) Chapter 15 of *Crystallographic Computing, Volume* 5 IUCr/Oxford University Press; Murthy (1996) Chapter 5 of *Crystallographic Methods and Protocols* Humana Press; Dauter et al. (2000) "Novel approach to phasing proteins: derivatization by short cryo-soaking with halides" Acta Cryst. D 56:232-237; Dauter (2002) "New approaches to high-throughput phasing" Curr. Opin. Structural Biol. 12:674-678; Chen et al. (1991) "Crystal structure of a bovine neurophysin-II dipeptide complex at 2.8 Å determined from the single-wavelength anomalous scattering signal of an incorporated iodine atom" Proc. Natl Acad. Sci. USA, 88:4240-4244; and Gavira et al. (2002) "Ab initio crystallographic structure determination of insulin from protein to electron density without crystal handling" Acta Cryst. D 58:1147-1154.

In addition, a variety of programs to facilitate data collection, phase determination, model building and refinement, and the like are publicly available. Examples include, but are not limited to, the HKL2000 package (Otwinowski and Minor (1997) "Processing of X-ray Diffraction Data Collected in Oscillation Mode" Methods in Enzymology 276:307-326), the CCP4 package (Collaborative Computational Project (1994) "The CCP4 suite: programs for protein crystallography" Acta Crystallogr D 50:760-763), SOLVE and RESOLVE (Terwilliger and Berendzen (1999) Acta Crystallogr D 55 (Pt 4):849-861), SHELXS and SHELXD (Schneider and Sheldrick (2002) "Substructure solution with SHELXD" Acta Crystallogr D Biol Crystallogr 58:1772-1779), Refmac5 (Murshudov et al. (1997) "Refinement of Macromolecular Structures by the Maximum-Likelihood Method" Acta Crystallogr D 53:240-255), PRODRG (van Aalten et al. (1996) "PRODRG, a program for generating molecular topologies and unique molecular descriptors from coordinates of small molecules" J Comput Aided Mol Des 10:255-262), and Coot (Elmsley et al. (2010) "Features and Development of Coot" Acta Cryst D 66:486-501.

Techniques for structure determination by NMR spectroscopy are similarly well described in the literature. See, e.g., Cavanagh et al. (1995) *Protein NMR Spectroscopy: Principles and Practice*, Academic Press; Levitt (2001) *Spin Dynamics: Basics of Nuclear Magnetic Resonance*, John Wiley & Sons; Evans (1995) *Biomolecular NMR Spectroscopy*, Oxford University Press; Wüthrich (1986) *NMR of Proteins and Nucleic Acids* (Baker Lecture Series), Kurt Wiley-Interscience; Neuhaus and Williamson (2000) *The Nuclear Overhauser Effect in Structural and Conformational Analysis*, 2nd Edition, Wiley-VCH; Macomber (1998) *A Complete Introduction to Modern NMR Spectroscopy*, Wiley-Interscience; Downing (2004) *Protein NMR Techniques* (Methods in Molecular Biology), 2nd edition, Humana Press; Clore and Gronenborn (1994) *NMR of Proteins* (Topics in Molecular and Structural Biology), CRC Press; Reid (1997) *Protein NMR Techniques*, Humana Press; Krishna and Berliner (2003) *Protein NMR for the Millenium* (Biological Magnetic Resonance), Kluwer Academic Publishers; Kiihne and De Groot (2001) *Perspectives on Solid State NMR in Biology* (Focus on Structural Biology, 1), Kluwer Academic Publishers; Jones et al. (1993) *Spectroscopic Methods and Analyses: NMR, Mass Spectrometry, and Related Techniques* (Methods in Molecular Biology, Vol. 17), Humana Press; Goto and Kay (2000) Curr. Opin. Struct. Biol. 10:585; Gardner (1998) Annu. Rev. Biophys. Biomol. Struct. 27:357; Wüthrich (2003) Angew. Chem. Int. Ed. 42:3340; Bax (1994) Curr. Opin. Struct. Biol. 4:738; Pervushin et al. (1997) Proc. Natl. Acad. Sci. U.S.A. 94:12366; Fiaux et al. (2002) Nature 418:207; Fernandez and Wider (2003) Curr. Opin. Struct. Biol. 13:570; Ellman et al. (1992) J. Am. Chem. Soc. 114:7959; Wider (2000) BioTechniques 29:1278-1294; Pellecchia et al. (2002) Nature Rev. Drug Discov. (2002) 1:211-219; Arora and Tamm (2001) Curr. Opin. Struct. Biol. 11:540-547; Flaux et al. (2002) Nature 418:207-211; Pellecchia et al. (2001) J. Am. Chem. Soc. 123:4633-4634; and Pervushin et al. (1997) Proc. Natl. Acad. Sci. USA 94:12366-12371.

The structure of a biotin-binding protein or of a biotin-binding protein bound to biotin or a biotin analog can, as noted, be directly determined, e.g., by x-ray crystallography or NMR spectroscopy, or the structure can be modeled based on a structure of the biotin-binding protein. The biotin binding site or other relevant domain of the protein can be identified, for example, by homology with other biotin-binding proteins, examination of protein-biotin co-complexes, biochemical analysis of mutant biotin-binding proteins, and/or the like.

Such modeling can involve simple visual inspection of a model of the polymerase, for example, using molecular graphics software such as Rosetta (available at www (dot) rosettacommons (dot) org), the PyMOL viewer (open source, freely available on the World Wide Web at www (dot) pymol (dot) org), Insight II, or Discovery Studio 2.1 (commercially available from Accelrys at www (dot) accelrys (dot) com/products/discovery-studio). Alternatively, modeling of the binding site complex of the biotin-binding protein or a putative mutant protein, for example, can involve computer-assisted docking, molecular dynamics, free energy minimization, and/or like calculations. Such modeling techniques have been well described in the literature; see, e.g., Babine and Abdel-Meguid (eds.) (2004) *Protein Crystallography in Drug Design*, Wiley-VCH, Weinheim; Lyne (2002) "Structure-based virtual screening: An overview" Drug Discov. Today 7:1047-1055; Molecular Modeling for Beginners, at www (dot) usm (dot) maine (dot) edu/~rhodes/SPVTut/index (dot) html; and Methods for Protein Simulations and Drug Design at www (dot) dddc (dot) ac (dot) cn/embo04; and references therein. Software to facilitate such modeling is widely available, for example, Rosetta, the CHARMm simulation package, available academically from Harvard University or commercially from Accelrys (at www (dot) accelrys (dot) com), the Discover simulation package (included in Insight II, supra), and Dynama (available at www (dot) cs (dot) gsu (dot) edu/~cscrwh/progs/progs (dot) html). See also an extensive list of modeling software at www (dot) netsci (dot) org/Resources/Software/Modeling/MMMD/top (dot) html.

Visual inspection and/or computational analysis of a protein model, including optional comparison of models of the protein in different states, can identify relevant features of the biotin-binding protein, including, for example, residues that can be mutated to alter surface charge.

As an example, analysis of a streptavidin model identified solvent-exposed residues that can be mutated to reduce the net charge, that do not interact with other streptavidin side chains, and that have not been implicated in the literature as affecting protein expression, stability, or biotin affinity. Residues identified as targets for decreasing net charge include, e.g., A2, A22, T53, N69, A104, and K121. Residues identified by similar criteria but that do exhibit minor side chain interactions include, e.g., T15, A87, A89, N92, T116, and T118. Additional residues that can be mutated to alter net charge include, e.g., G3, T19, R40, V42, Y47, R90, A106, and K119. Exemplary substitutions include, e.g., A2D, A2E, G3D, G3E, T15E, T15D, T19E, T19D, A22E, A22D, R40Y, R40E, R40D, V42D, V42E, Y47D, Y47E, T53D, T53E, N69D, N69E, A87E, A87D, A89D, A89E, R90T, N92E, N92D, A104E, A104D, A106E, A106D, T116D, T116E, T118D, T118E, K119T, K121E, and K121D. Site-saturated mutagenesis to all possible residues at these positions can also be performed.

It will be evident that calculated net charge can be decreased to essentially any desired level by combining such mutations (and optionally covalent modifications and/or exogenous sequences as detailed herein). As a few examples, combinations of mutations such as A2D, A22E, T53D, N69D, A104E, and K121E; A2D, T15E, A22E, T53D, N69D, A87E, A89D, N92E, A104E, T116D, T118D, and K121E; A2D, T53D, and N69D; A22E, A104E, and K121E; A2D, A22E, T53D, N69D, A87E, N92E, A104E, T118D, and K121E; or A2D, T15E, A22E, T53D, N69D, A87E, A89E, N92E, A104E, T116D, T118D, and K121E can be employed in streptavidin.

Mutagenesis can also be employed to introduce sites for covalent modification. Residues with reactive side chains (e.g., lysine, cysteine, etc. as described above) can be introduced at essentially any desired position, e.g., identified by structural analysis. For example, residues that can be mutated to lysine to introduce modification sites into streptavidin include, e.g., A2, T15, G21, T29, R40, A50, Y70, R90, N92, and T116. Combination of such mutations permits control over the maximum number of available modification sites. As a few examples, combinations of mutations such as G21K and Y70K; A2K, R40K, and A50K; A2K, G21K, R40K, A50K, and Y70K; A2K, G21K, R40K, A50K, Y70K, R90K, N92K, and T116K; and A2K, T15K, G21K, T29K, R40K, A50K, Y70K, R90K, N92K, and T116K can be introduced into streptavidin. Such mutant streptavidins are optionally modified with a reagent that reacts with primary amines as detailed above, e.g., to introduce one or more negatively charged groups.

Similarly, mutagenesis can be employed to remove undesired modification sites. For example, where streptavidin is to be modified with a reagent that reacts with primary amines, one or more lysine residues can be mutated to reduce the total number of sites available for modification. Accordingly, a recombinant streptavidin can include an amino acid substitution at position K67, K108, K119, and/or K121. Exemplary substitutions include, e.g., K67R, K108R, K119R, and K121R. Additional possible substitutions that alter charge as well as remove modification sites include, e.g., K67E, K67D, K108E, K108D, K119E, K119D, K121D, and K121E, as well as mutation of lysine to an uncharged residue. The lysine at position 108 is close to the biotin binding site. In some instances, without limitation to any particular mechanism, covalent modification of this residue can interfere with biotin binding by the modified streptavidin; replacement of this lysine (K108) by mutagenesis (e.g., to arginine) can therefore be desirable.

As noted, residues required for high affinity binding of biotin can be avoided during mutagenesis. In some applications, however, weaker biotin binding is desirable (for example, to facilitate subsequent removal of the biotin-binding protein from a surface or other entity, where simultaneous binding of a divalent or multivalent biotin-binding protein to two biotin moieties (e.g., to two adjacent biotins or to a bis-biotin moiety) can compensate for the decreased affinity of individual binding events, or the like). In embodiments in which weaker binding of biotin is desired, a recombinant streptavidin can include an amino acid substitution at positions such as, e.g., N10, S14, S32, R40, R71, R90, and/or D115. Exemplary substitutions include, e.g., N10A, N10D, N10E, S14D, S14A, S32A, R40D, R71D, R90D, D115A, and D115N. An exemplary streptavidin including a combination of N10A, S14D, and S32A mutations exhibits very weak biotin binding (with $K_d$ on the order of mM).

The recombinant biotin-binding protein optionally includes additional features exogenous or heterologous to the biotin-binding protein. For example, the recombinant biotin-binding protein optionally includes one or more tags, e.g., purification, substrate binding, or other tags, such as a polyglutamate tag, a Glu10 tag, a polyaspartate tag, an Asp10 tag, a polylysine tag, a Lys10 tag, a tag including a mixture of aspartate and glutamate residues, a polyhistidine tag, a His10 tag, a His6 tag, an alanine tag, an Ala10 tag, an Ala16 tag, a Tat fusion peptide (e.g., a YGRKKRRQRRR peptide; SEQ ID NO:27), a SpyTag, a SpyCatcher domain, a SnoopTag, a SnoopCatcher domain, a biotin tag, a biotin ligase recognition sequence or other biotin attachment site (e.g., a BiTag or a Btag or variant thereof, e.g., BtagV1-11; see, e.g., US patent application publication 2012-0034602), a GST tag, an S Tag, a SNAP-tag, an HA tag, a DSB (Sso7D) tag, a lysine tag, a NanoTag, a Cmyc tag, a tag or linker comprising the amino acids glycine and serine, a tag or linker comprising the amino acids glycine, serine, alanine and histidine, a tag or linker comprising the amino acids glycine, arginine, lysine, glutamine and proline, a plurality of polyhistidine tags, a plurality of His10 tags, a plurality of His6 tags, a plurality of alanine tags, a plurality of Ala10 tags, a plurality of Ala16 tags, a plurality of biotin tags, a plurality of GST tags, a plurality of BiTags, a plurality of S Tags, a plurality of SNAP-tags, a plurality of HA tags, a plurality of DSB (Sso7D) tags, a plurality of lysine tags, a plurality of NanoTags, a plurality of Cmyc tags, a plurality of tags or linkers comprising the amino acids glycine and serine, a plurality of tags or linkers comprising the amino acids glycine, serine, alanine and histidine, a plurality of tags or linkers comprising the amino acids glycine, arginine, lysine, glutamine and proline, biotin, avidin, an antibody or antibody domain, antibody fragment, antigen, receptor, receptor domain, receptor fragment, or ligand, one or more protease site (e.g., TEV protease (e.g., ENLYFQG; SEQ ID NO:28), Factor Xa, enterokinase, or thrombin (e.g., LVPRGS; SEQ ID NO:29) site), a dye, an acceptor, a quencher, a DNA binding domain (e.g., a helix-hairpin-helix domain from topoisomerase V), or combination thereof. An initial methionine residue can be added for convenient expression of recombinant protein. The one or more exogenous or heterologous features can find use not only for purification purposes and the like, but can also be useful for altering one or more properties of the biotin-binding protein. For example, introducing a polyglutamate or polyaspartate tag decreases the net charge. As another example, introduction of a polylysine tag provides additional sites for covalent modification.

The one or more exogenous or heterologous features can be included internal to the biotin-binding protein (e.g., to at least one monomer thereof, e.g., inserted into a loop region), at the N-terminal region of the biotin-binding protein (e.g., of at least one monomer thereof), and/or at the C-terminal region of the biotin-binding protein (e.g., of at least one monomer thereof). As just a few examples, exogenous features can be included at both the N-terminal and C-terminal regions of the biotin-binding protein (e.g., of at least one monomer thereof), at multiple internal sites, or at a terminal region and internal to the monomer. Where the biotin-binding protein includes an exogenous or heterologous feature at two or more regions (e.g., at both the N- and C-terminal regions), the exogenous or heterologous features can be the same or different. Optionally, an internal and/or terminal region (e.g., the N- or C-terminal region) of a biotin-binding protein of the invention can comprise two or more exogenous or heterologous features which can be the same or different.

The various mutations, exogenous features, and/or covalent modifications described herein or known in the art can be combined in recombinant streptavidins or other biotin-binding proteins of the invention. For example, a recombinant streptavidin can comprise one or more covalent modifications that decrease its calculated net charge relative to a parental streptavidin lacking the covalent modification, one or more mutations that decrease its net charge, and a C-terminal polyglutamate tail. As another example, a recombinant streptavidin can comprise one or more covalent modifications that decrease its calculated net charge relative to a parental streptavidin lacking the covalent modification, one or more mutations that decrease its net charge, one or more mutations that introduce additional sites for covalent modification, one or more mutations that remove undesired modification sites, one or more mutations that affect biotin affinity, and a C-terminal polyglutamate tail.

In one class of embodiments, a recombinant streptavidin of the invention comprises at least one monomer that comprises an amino acid sequence that is at least 70% identical to SEQ ID NO:1, e.g., at least 80%, at least 85%, at least 90%, at least 95%, at least 97%, or at least 98% identical. In one embodiment, the recombinant streptavidin comprises four monomers that each comprise an amino acid sequence that is at least 70% identical to SEQ ID NO:1, e.g., at least 80%, at least 85%, at least 90%, at least 95%, at least 97%, or at least 98% identical. Optionally, the recombinant streptavidin comprises four monomers that are identical in their amino acid sequence.

In most embodiments, the mutations that are introduced into a biotin-binding protein do not interfere with biotin binding activity or interfere minimally. Accordingly, in some embodiments, the recombinant biotin-binding protein exhibits a $K_d$ for biotin (or an analog) that is no more than 100 times or no more than 10 times the $K_d$ exhibited by a parental protein lacking the mutation(s), under equivalent reaction conditions. For example, a recombinant streptavidin derived from SEQ ID NO:1 can exhibit a $K_d$ for biotin (or an analog) that is no more than 100 times or no more than 10 times the $K_d$ exhibited by a parental streptavidin whose four monomers comprise SEQ ID NO:1.

The recombinant mutated biotin-binding protein can be employed for essentially any desired application. For example, the recombinant biotin-binding protein can be used to immobilize a nucleic acid, e.g., a biotinylated nucleic acid or a complex comprising the nucleic acid. In one exemplary class of embodiments, the recombinant biotin-binding protein is bound to a nucleic acid polymerase e.g., a biotinylated (e.g., bis-biotinylated) polymerase. Optionally, the nucleic acid polymerase is complexed with a nucleic acid. For example, the recombinant biotin-binding protein can be bound to a DNA polymerase that is complexed with a DNA template. The recombinant biotin-binding protein is optionally immobilized on a solid support, e.g., whose surface is coated in biotin (e.g., bis-biotin). In one class of embodiments particularly useful for single molecule applications, the recombinant biotin-binding protein is immobilized on the base of a nanoscale well, e.g., a zero mode waveguide (ZMW). Optionally, the composition is present in a nucleic acid sequencing system, e.g., a DNA sequencing system as described below.

The amino acid sequence of a wild type core streptavidin monomer is provided as SEQ ID NO:1 in Table 1. The sequence of a less processed streptavidin monomer is provided as SEQ ID NO:2. The amino acid sequences of exemplary recombinant streptavidins, and optional exogenous features at the N- and/or C-terminal region, are also provided in Table 1. Positions of amino acid substitutions are identified relative to wild type streptavidin (SEQ ID NO:1). Streptavidins of the invention (including those provided in Table 1) can include any exogenous or heterologous feature (or combination of such features) at the N- and/or C-terminal region or internal to the monomer. For example, it will be understood that streptavidin mutants in Table 1 that do not include, e.g., a C-terminal polyglutamate tag can be modified to include a polyglutamate tag at the C-terminal region, alone or in combination with any of the exogenous or heterologous features described herein. Similarly, some or all of the exogenous features listed in Table 1 can be omitted and still result in a streptavidin of the invention.

TABLE 1

Amino acid sequences of exemplary streptavidin monomers

| SEQ ID NO | Amino Acid Sequence |
|---|---|
| 1<br>core streptavidin monomer | EAGITGTWYNQLGSTFIVTAGADGALTGTYESAVGN<br>AESRYVLTGRYDSAPATDGSGTALGWTVAWKNNYR<br>NAHSATTWSGQYVGGAEARINTQWLLTSGTTEANA<br>WKSTLVGHDTFTKVKPSAAS |
| 2<br>streptavidin monomer with<br>N- and C-terminal<br>precursor sequences | DPSKDSKAQVSAAEAGITGTWYNQLGSTFIVTAGAD<br>GALTGTYESAVGNAESRYVLTGRYDSAPATDGSGTA<br>LGWTVAWKNNYRNAHSATTWSGQYVGGAEARINT<br>QWLLTSGTTEANAWKSTLVGHDTFTKVKPSAASIDA<br>AKKAGVNNGNPLDAVQQ |
| 3<br>Streptavidin EEEEEEEEE.<br>ENLYFQG.His6 | MEAGITGTWYNQLGSTFIVTAGADGALTGTYESAVG<br>NAESRYVLTGRYDSAPATDGSGTALGWTVAWKNN<br>YRNAHSATTWSGQYVGGAEARINTQWLLTSGTTEA<br>NAWKSTLVGHDTFTKVKPSAASEEEEEEEEEENLY<br>FQGHHHHHH |

TABLE 1-continued

Amino acid sequences of exemplary streptavidin monomers

| SEQ ID NO | Amino Acid Sequence |
|---|---|
| 4<br>Streptavidin.KKKKKKKKKK.<br>ENLYFQG.His6 | MEAGITGTWYNQLGSTFIVTAGADGALTGTYESAVG<br>NAESRYVLTGRYDSAPATDGSGTALGWTVAWKNN<br>YRNAHSATTWSGQYVGGAEARINTQWLLTSGTTEA<br>NAWKSTLVGHDTFTKVKPSAASKKKKKKKKKKENL<br>YFQGHHHHHH |
| 5<br>Streptavidin.EEEEEEEEEE | MGEAGITGTWYNQLGSTFIVTAGADGALTGTYESAV<br>GNAESRYVLTGRYDSAPATDGSGTALGWTVAWKN<br>NYRNAHSATTWSGQYVGGAEARINTQWLLTSGTTE<br>ANAWKSTLVGHDTFTKVKPSAASEEEEEEEEEE |
| 6<br>Streptavidin.K67R | MGEAGITGTWYNQLGSTFIVTAGADGALTGTYESAV<br>GNAESRYVLTGRYDSAPATDGSGTALGWTVAWRNN<br>YRNAHSATTWSGQYVGGAEARINTQWLLTSGTTEA<br>NAWKSTLVGHDTFTKVKPSAAS |
| 7<br>Streptavidin.K108R | MGEAGITGTWYNQLGSTFIVTAGADGALTGTYESAV<br>GNAESRYVLTGRYDSAPATDGSGTALGWTVAWKN<br>NYRNAHSATTWSGQYVGGAEARINTQWLLTSGTTE<br>ANAWRSTLVGHDTFTKVKPSAAS |
| 8<br>Streptavidin.K119R_K121R | MGEAGITGTWYNQLGSTFIVTAGADGALTGTYESAV<br>GNAESRYVLTGRYDSAPATDGSGTALGWTVAWKN<br>NYRNAHSATTWSGQYVGGAEARINTQWLLTSGTTE<br>ANAWKSTLVGHDTFTRVRPSAAS |
| 9<br>Streptavidin.K67R_K108R_<br>K119R_K121R | MGEAGITGTWYNQLGSTFIVTAGADGALTGTYESAV<br>GNAESRYVLTGRYDSAPATDGSGTALGWTVAWRNN<br>YRNAHSATTWSGQYVGGAEARINTQWLLTSGTTEA<br>NAWRSTLVGHDTFTRVRPSAAS |
| 10<br>Streptavidin.K67R_K108R | MGEAGITGTWYNQLGSTFIVTAGADGALTGTYESAV<br>GNAESRYVLTGRYDSAPATDGSGTALGWTVAWRNN<br>YRNAHSATTWSGQYVGGAEARINTQWLLTSGTTEA<br>NAWRSTLVGHDTFTKVKPSAAS |
| 11<br>Streptavidin.K108R_K119R_<br>K121R | MGEAGITGTWYNQLGSTFIVTAGADGALTGTYESAV<br>GNAESRYVLTGRYDSAPATDGSGTALGWTVAWKN<br>NYRNAHSATTWSGQYVGGAEARINTQWLLTSGTTE<br>ANAWRSTLVGHDTFTRVRPSAAS |
| 12<br>Streptavidin.K67R_K119R_<br>K121R | MGEAGITGTWYNQLGSTFIVTAGADGALTGTYESAV<br>GNAESRYVLTGRYDSAPATDGSGTALGWTVAWRNN<br>YRNAHSATTWSGQYVGGAEARINTQWLLTSGTTEA<br>NAWKSTLVGHDTFTRVRPSAAS |
| 13<br>Streptavidin.KKKKKKKKKK | MGEAGITGTWYNQLGSTFIVTAGADGALTGTYESAV<br>GNAESRYVLTGRYDSAPATDGSGTALGWTVAWKN<br>NYRNAHSATTWSGQYVGGAEARINTQWLLTSGTTE<br>ANAWKSTLVGHDTFTKVKPSAASKKKKKKKKKK |
| 14<br>Streptavidin. E1R_E88R_<br>E103R_P122R_S123R | MGRAGITGTWYNQLGSTFIVTAGADGALTGTYESAV<br>GNAESRYVLTGRYDSAPATDGSGTALGWTVAWKN<br>NYRNAHSATTWSGQYVGGARARINTQWLLTSGTTR<br>ANAWKSTLVGHDTFTKVKRRAAS |
| 15<br>Streptavidin.GGGS.LVPRGS.<br>GGGS.YGRKKRRQRRR | MGEAGITGTWYNQLGSTFIVTAGADGALTGTYESAV<br>GNAESRYVLTGRYDSAPATDGSGTALGWTVAWKN<br>NYRNAHSATTWSGQYVGGAEARINTQWLLTSGTTE<br>ANAWKSTLVGHDTFTKVKPSAASGGGSLVPRGSGG<br>GSYGRKKRRQRRR |
| 16<br>Streptavidin.S39G_R40D_<br>R71D | MGEAGITGTWYNQLGSTFIVTAGADGALTGTYESAV<br>GNAEGDYVLTGRYDSAPATDGSGTALGWTVAWKN<br>NYDNAHSATTWSGQYVGGAEARINTQWLLTSGTTE<br>ANAWKSTLVGHDTFTKVKPSAAS |
| 17<br>Streptavidin.S39G_R40D_<br>R90D | MGEAGITGTWYNQLGSTFIVTAGADGALTGTYESAV<br>GNAEGDYVLTGRYDSAPATDGSGTALGWTVAWKN<br>NYRNAHSATTWSGQYVGGAEADINTQWLLTSGTTE<br>ANAWKSTLVGHDTFTKVKPSAAS |
| 18<br>M.His6.LVPRGS.Streptavidin.<br>A2D_T53D_N69D | MHHHHHHLVPRGSGEDGITGTWYNQLGSTFIVTAGA<br>DGALTGTYESAVGNAESRYVLTGRYDSAPADDGSG<br>TALGWTVAWKNDYRNAHSATTWSGQYVGGAEARI<br>NTQWLLTSGTTEANAWKSTLVGHDTFTKVKPSAAS |

TABLE 1-continued

Amino acid sequences of exemplary streptavidin monomers

| SEQ ID NO | Amino Acid Sequence |
|---|---|
| 19<br>M.His6.LVPRGS.Streptavidin.<br>A22E_A104E_K121E | MHHHHHHLVPRGSGEAGITGTWYNQLGSTFIVTAGE<br>DGALTGTYESAVGNAESRYVLTGRYDSAPATDGSGT<br>ALGWTVAWKNNYRNAHSATTWSGQYVGGAEARIN<br>TQWLLTSGTTEENAWKSTLVGHDTFTKVEPSAAS |
| 20<br>M.His6.LVPRGS.Streptavidin.<br>A2D_A22E_T53D_N69D_<br>A104E_K121E | MHHHHHHLVPRGSGEDGITGTWYNQLGSTFIVTAGE<br>DGALTGTYESAVGNAESRYVLTGRYDSAPADDGSG<br>TALGWTVAWKNDYRNAHSATTWSGQYVGGAEARI<br>NTQWLLTSGTTEENAWKSTLVGHDTFTKVEPSAAS |
| 21<br>M.His6.LVPRGS.Streptavidin.<br>A2D_A22E_T53D_N69D_<br>A87E_N92E_A104E_<br>T118D_121E | MHHHHHHLVPRGSGEDGITGTWYNQLGSTFIVTAGE<br>DGALTGTYESAVGNAESRYVLTGRYDSAPADDGSG<br>TALGWTVAWKNDYRNAHSATTWSGQYVGGEEARI<br>ETQWLLTSGTTEENAWKSTLVGHDTFDKVEPSAAS |
| 22<br>M.His6.LVPRGS.Streptavidin.<br>A2D_T15E_A22E_T53D_<br>N69D_A87E_A89D_<br>N92E_A104E_T116D_<br>T118D_K121E | MHHHHHHLVPRGSGEDGITGTWYNQLGSDFIVTAGE<br>DGALTGTYESAVGNAESRYVLTGRYDSAPADDGSG<br>TALGWTVAWKNDYRNAHSATTWSGQYVGGEEDRI<br>ETQWLLTSGTTEENAWKSTLVGHDDFDKVEPSAAS |
| 23<br>M.His6.LVPRGS.Streptavidin.<br>N10A_S14D_S32A | MHHHHHHLVPRGSGEAGITGTWYAQLGDTFIVTAG<br>ADGALTGTYEAAVGNAESRYVLTGRYDSAPATDGS<br>GTALGWTVAWKNNYRNAHSATTWSGQYVGGAEAR<br>INTQWLLTSGTTEANAWKSTLVGHDTFTKVKPSAAS |
| 24<br>Streptavidin.A22E_A104E_<br>K121EEEEEEEEEEE | MGEAGITGTWYNQLGSTFIVTAGEDGALTGTYESAV<br>GNAESRYVLTGRYDSAPATDGSGTALGWTVAWKN<br>NYRNAHSATTWSGQYVGGAEARINTQWLLTSGTTE<br>ENAWKSTLVGHDTFTKVEPSAASEEEEEEEEEE |
| 25<br>Streptavidin.A22E_A104E_<br>K121E.KKKKKKKKKK | MGEAGITGTWYNQLGSTFIVTAGEDGALTGTYESAV<br>GNAESRYVLTGRYDSAPATDGSGTALGWTVAWKN<br>NYRNAHSATTWSGQYVGGAEARINTQWLLTSGTTE<br>ENAWKSTLVGHDTFTKVEPSAASKKKKKKKKKK |
| 26<br>M EEEEEEEEE Streptavidin.<br>A22E_A104E_K121EEEEEEEEEE | MEEEEEEEEEGEAGITGTWYNQLGSTFIVTAGEDGA<br>LTGTYESAVGNAESRYVLTGRYDSAPATDGSGTALG<br>WTVAWKNNYRNAHSATTWSGQYVGGAEARINTQW<br>LLTSGTTEENAWKSTLVGHDTFTKVEPSAASEEEEEE<br>EEEE |

Applications of Modified and Mutant Biotin-Binding Proteins

The modified and/or mutated biotin-binding proteins described herein are particularly well suited for applications such as connecting or immobilizing biotinylated components.

One aspect of the invention provides a solid support on which is immobilized a biotin-binding protein described herein, e.g., a mutated and/or covalently modified biotin-binding protein. Any of the variety of solid supports known in the art can be employed, e.g., a substrate comprising reaction regions, optionally nanoscale reaction regions. The surface is typically coated in biotin (e.g., bis-biotin) or a biotin analog, to which the protein is bound.

Accordingly, one class of embodiments provides a substrate comprising at least one nanoscale well in which is immobilized a biotin-binding protein. Any of the mutated and/or modified biotin-binding proteins described herein can be employed. In one class of embodiments, the biotin-binding protein has a calculated net charge of −10 or less at pH 7.4, e.g., −15 or less, −20 or less, −30 or less, −40 or less, −44 or less, −50 or less, −60 or less, −70 or less, or even −80 or less.

Optionally, the biotin-binding protein is a tetravalent or divalent biotin-binding protein, e.g., streptavidin, avidin, deglycoslylated avidin (NeutrAvidin), traptavidin, tamavidin, xenavidin, bradavidin, AVR2, AVR4, rhizavidin, and variants, mutants, derivatives, or homologs thereof. In one class of embodiments, the modified biotin-binding protein comprises at least one monomer that comprises an amino acid sequence that is at least 70% identical to SEQ ID NO:1, e.g., at least 80%, at least 85%, at least 90%, at least 95%, at least 97%, or at least 98% identical. In one embodiment, the parental biotin-binding protein comprises four monomers that each comprise an amino acid sequence that is at least 70% identical to SEQ ID NO:1, e.g., at least 80%, at least 85%, at least 90%, at least 95%, at least 97%, or at least 98% identical.

In some embodiments, the biotin-binding protein comprises one or more covalent modifications that decrease its calculated net charge relative to a parental biotin-binding protein lacking the covalent modifications. For example, the biotin-binding protein can comprise one or more covalently attached sulfonate moieties, e.g., three or more, 12 or more, 24 or more, 30 or more, 45 or more, 50 or more, or even 60 or more covalently attached sulfonate moieties. For example, the biotin-binding protein can comprise one or more covalently attached 3,4,5-tris(3-sulfopropoxy)benzoyl moieties, e.g., four or more, 10 or more, 15 or more, 16 or more, 17 or more, 18 or more, 19 or more, or even 20 or more covalently attached 3,4,5-tris(3-sulfopropoxy)benzoyl moieties. Additional exemplary modifications have been described above.

In some embodiments, the biotin-binding protein comprises one or more amino acid substitutions that decrease its calculated net charge relative to a parental biotin-binding protein, e.g., one or more amino acid substitutions that replace a positively charged or uncharged residue in the parental biotin-binding protein with a negatively charged residue. Exemplary mutations have been described above.

The biotin-binding protein optionally comprises one or more exogenous feature, alone or in addition to one or more covalent modifications and/or mutations. For example, in one class of embodiments, the biotin-binding protein comprises a polyglutamate, polyaspartate, or polylysine tag, e.g., at the N- or C-terminus of at least one monomer.

The biotin-binding protein can be used to immobilize essentially any desired molecule of interest. For example, the biotin-binding protein can be used to immobilize a nucleic acid, e.g., a biotinylated nucleic acid or a complex comprising the nucleic acid. In one exemplary class of embodiments, the biotin-binding protein is bound to a nucleic acid polymerase, e.g., a biotinylated (e.g., bis-biotinylated) polymerase. Optionally, a polymerase-nucleic acid complex is bound to the biotin-binding protein. For example, the biotin-binding protein can be bound to a biotinylated (e.g., bis-biotinylated) DNA polymerase that is complexed with a DNA template.

Suitable substrates are described hereinbelow and are known in the art. Exemplary nanoscale wells include, e.g., zero mode waveguides. For single molecule analysis, the biotin-binding protein is typically immobilized on the bottom of the well. Optionally, only the bottom surface of the well is biotinylated. In one class of embodiments, the substrate comprises at least 500,000 nanoscale wells, a plurality of which comprise an immobilized biotin-binding protein, e.g., at least 1,000,000, 2,000,000, 3,000,000, 4,000,000, 5,000,000, 6,000,000, 7,000,000, 8,000,000, 9,000,000, or 10,000,000 wells. The substrate is optionally present in a nucleic acid sequencing system.

A related aspect of the invention provides complexes that include a biotin-binding protein described herein, e.g., a mutated and/or covalently modified biotin-binding protein, bound to at least one molecule of interest, e.g., a biotinylated (e.g. a bis-biotinylated) protein, polypeptide, nucleic acid, nucleotide, label, or other moiety. For exemplary nucleotide analogs including biotin-binding proteins, into which any biotin-binding protein of the invention can be incorporated, see, e.g., U.S. Pat. No. 9,062,091 and U.S. patent application publications 2017/0145495, 2017/0145496, and 2017/0145502 (each of which is hereby incorporated by reference in its entirety).

One general class of embodiments provides a complex comprising a biotin-binding protein and a nucleic acid. In one class of embodiments, the biotin-binding protein has a calculated net charge of −10 or less at pH 7.4, e.g., −15 or less, −20 or less, −30 or less, −40 or less, −44 or less, −50 or less, −60 or less, −70 or less, or even −80 or less. As noted above, such negatively charged biotin-binding proteins can be favorably employed to bind to and optionally immobilize nucleic acids (and complexes thereof), despite the significant electrostatic repulsion expected to occur between the highly negatively charged nucleic acid and the negatively charged biotin-binding protein.

The nucleic acid can be, e.g., a DNA or RNA and can be, e.g., single-stranded or double-stranded or a combination thereof. The nucleic acid can be of essentially any desired length. For example, the nucleic acid can be at least about 100 nucleotides in length, e.g., at least 500, at least 1,000, at least 5,000, at least 10,000, at least 50,000, or at least 100,000 nucleotides. In some embodiments, the nucleic acid is a DNA that comprises a double-stranded region at least 1 kb in length, e.g., at least 5 kb, at least 10 kb, at least 50 kb, or at least 100 kb. The complex optionally also includes a protein such as a nucleic acid polymerase, a helicase, or an exonuclease that is bound to the nucleic acid. Optionally, the protein comprises a biotin or bis-biotin tag through which the protein (and thus the nucleic acid) is bound to the biotin-binding protein. In other embodiments, the nucleic acid is biotinylated and bound directly to the biotin-binding protein.

Optionally, the biotin-binding protein is a tetravalent or divalent biotin-binding protein, e.g., streptavidin, avidin, deglycoslylated avidin (NeutrAvidin), traptavidin, tamavidin, xenavidin, bradavidin, AVR2, AVR4, rhizavidin, and variants, mutants, derivatives, or homologs thereof. In one class of embodiments, the modified biotin-binding protein comprises at least one monomer that comprises an amino acid sequence that is at least 70% identical to SEQ ID NO:1, e.g., at least 80%, at least 85%, at least 90%, at least 95%, at least 97%, or at least 98% identical. In one embodiment, the parental biotin-binding protein comprises four monomers that each comprise an amino acid sequence that is at least 70% identical to SEQ ID NO:1, e.g., at least 80%, at least 85%, at least 90%, at least 95%, at least 97%, or at least 98% identical.

In some embodiments, the biotin-binding protein comprises one or more covalent modifications that decrease its calculated net charge relative to a parental biotin-binding protein lacking the covalent modifications. For example, the biotin-binding protein can comprise one or more covalently attached sulfonate moieties, e.g., three or more, 12 or more, 24 or more, 30 or more, 45 or more, 50 or more, or even 60 or more covalently attached sulfonate moieties. For example, the biotin-binding protein can comprise one or more covalently attached 3,4,5-tris(3-sulfopropoxy)benzoyl moieties, e.g., four or more, 10 or more, 15 or more, 16 or more, 17 or more, 18 or more, 19 or more, or even 20 or more covalently attached 3,4,5-tris(3-sulfopropoxy)benzoyl moieties. Additional exemplary modifications have been described above.

In some embodiments, the biotin-binding protein comprises one or more amino acid substitutions that decrease its calculated net charge relative to a parental biotin-binding protein, e.g., one or more amino acid substitutions that replace a positively charged or uncharged residue in the parental biotin-binding protein with a negatively charged residue. Exemplary mutations have been described above.

The biotin-binding protein optionally comprises one or more exogenous feature, alone or in addition to one or more covalent modifications and/or mutations, as described above. For example, in one class of embodiments, the biotin-binding protein comprises a polyglutamate, polyaspartate, or polylysine tag, e.g., at the N- or C-terminus of at least one monomer.

The biotin-binding protein can be immobilized on a solid support, e.g., on the base of a nanoscale well, proximal to a nanopore, on or proximal to a nanoFET, within an array, on a microsphere, bead or other particle, or the like. Typically, the surface of the solid support is biotinylated (or coated with a biotin analog) for convenient capture of the biotin-binding protein. The complex is optionally present in a nucleic acid sequencing system.

One general class of embodiments provides a complex comprising a biotin-binding protein and a nucleic acid polymerase. In one class of embodiments, the biotin-binding protein has a calculated net charge of −10 or less at pH 7.4, e.g., −15 or less, −20 or less, −30 or less, −40 or less, −44 or less, −50 or less, −60 or less, −70 or less, or even −80 or less. In some embodiments, the polymerase comprises a bis-biotin tag through which the polymerase is bound to the biotin-binding protein. In other embodiments, the polymerase comprises a single biotin moiety through which the polymerase is bound to the biotin-binding protein.

Essentially all of the features noted above apply to these embodiments as well, as relevant, e.g., with respect to type of biotin-binding protein, covalent modification of the biotin-binding protein, amino acid substitutions in the biotin-binding protein, exogenous features on the biotin-binding protein, immobilization on a solid support, use in a nucleic acid sequencing system, and the like.

Another related aspect of the invention provides methods employing the biotin-binding proteins described herein, e.g., mutated and/or covalently modified biotin-binding proteins, to immobilize molecules of interest (e.g., proteins, nucleic acids, complexes, etc.). One general class of embodiments provides methods of immobilizing a nucleic acid. In the methods, a surface comprising a plurality of array regions, which array regions comprise biotin or a biotin analog; is provided. The surface is exposed to a complex comprising a nucleic acid and a biotin-binding protein, whereby the biotin-binding protein binds to the biotin or biotin analog and thereby immobilizes the complex in the array regions. In one class of embodiments, the biotin-binding protein has a calculated net charge of −10 or less at pH 7.4, e.g., −15 or less, −20 or less, −30 or less, −40 or less, −44 or less, −50 or less, −60 or less, −70 or less, or even −80 or less.

Suitable array regions include, e.g., nanoscale wells (e.g., ZMWs), nanopores, and nanoFETs, for example, as described herein with regard to nucleic acid sequence determination. In one class of embodiments, the complex is immobilized on the bottom of nanoscale wells. It will be evident that the various techniques described herein can be employed separately or in combination, with each other and/or with techniques for loading molecules into array regions known in the art, such as those described, e.g., in U.S. Pat. No. 8,715,930 and U.S. patent application publication 2017/0136433.

The nucleic acid can be, e.g., a DNA or RNA and can be, e.g., single-stranded or double-stranded or a combination thereof. The nucleic acid can be of essentially any desired length. For example, the nucleic acid can be at least about 100 nucleotides in length, e.g., at least 500, at least 1,000, at least 5,000, at least 10,000, at least 50,000, or at least 100,000 nucleotides. In some embodiments, the nucleic acid is a DNA that comprises a double-stranded region at least 1 kb in length, e.g., at least 5 kb, at least 10 kb, at least 50 kb, or at least 100 kb. The complex optionally also includes a protein such as a nucleic acid polymerase, a helicase, or an exonuclease that is bound to the nucleic acid. Optionally, the protein comprises a biotin or bis-biotin tag through which the protein (and thus the nucleic acid) is bound to the biotin-binding protein. In other embodiments, the nucleic acid is biotinylated and bound directly to the biotin-binding protein.

Optionally, the biotin-binding protein is a tetravalent or divalent biotin-binding protein, e.g., streptavidin, avidin, deglycoslylated avidin (NeutrAvidin), traptavidin, tamavidin, xenavidin, bradavidin, AVR2, AVR4, rhizavidin, and variants, mutants, derivatives, or homologs thereof. In one class of embodiments, the modified biotin-binding protein comprises at least one monomer that comprises an amino acid sequence that is at least 70% identical to SEQ ID NO:1, e.g., at least 80%, at least 85%, at least 90%, at least 95%, at least 97%, or at least 98% identical. In one embodiment, the parental biotin-binding protein comprises four monomers that each comprise an amino acid sequence that is at least 70% identical to SEQ ID NO:1, e.g., at least 80%, at least 85%, at least 90%, at least 95%, at least 97%, or at least 98% identical.

In some embodiments, the biotin-binding protein comprises one or more covalent modifications that decrease its calculated net charge relative to a parental biotin-binding protein lacking the covalent modifications. For example, the biotin-binding protein can comprise one or more covalently attached sulfonate moieties, e.g., three or more, 12 or more, 24 or more, 30 or more, 45 or more, 50 or more, or even 60 or more covalently attached sulfonate moieties. For example, the biotin-binding protein can comprise one or more covalently attached 3,4,5-tris(3-sulfopropoxy)benzoyl moieties, e.g., four or more, 10 or more, 15 or more, 16 or more, 17 or more, 18 or more, 19 or more, or even 20 or more covalently attached 3,4,5-tris(3-sulfopropoxy)benzoyl moieties. Additional exemplary modifications have been described above.

In some embodiments, the biotin-binding protein comprises one or more amino acid substitutions that decrease its calculated net charge relative to a parental biotin-binding protein, e.g., one or more amino acid substitutions that replace a positively charged or uncharged residue in the parental biotin-binding protein with a negatively charged residue. Exemplary mutations have been described above.

The biotin-binding protein optionally comprises one or more exogenous feature, alone or in addition to one or more covalent modifications and/or mutations, as described above. For example, in one class of embodiments, the biotin-binding protein comprises a polyglutamate, polyaspartate, or polylysine tag, e.g., at the N- or C-terminus of at least one monomer.

In one particularly useful class of embodiments, the nucleic acid is immobilized in preparation for (or as a step in) determining its nucleotide sequence, for example, in a single molecule sequencing method as described herein.

A biotinylated surface can comprise more biotin groups than are desirably occupied by the nucleic acid/biotin-binding protein complex. (For example, in some embodiments, a single complex occupies the base of an individual nanoscale well, e.g., of a plurality of the wells in an array. In such embodiments, only one or two biotin groups on the surface of the well's base may be bound to the nucleic acid/biotin-binding protein complex.) Any remaining biotins on the surface are optionally blocked, for example, by contacting the surface with free biotin-binding protein, e.g., after exposing the surface to the complex and optionally washing or otherwise removing any excess, unbound complex. In this context, "free biotin-binding protein" refers to biotin-binding protein that is not complexed with the nucleic acid; this biotin-binding protein optionally has a different moiety bound to it (e.g., a biotin analog, a quencher, a label, etc.). The free biotin-binding protein can be the same as or different than that employed in the complex. In some embodiments, the free biotin-binding protein binds biotin more tightly than does the biotin-binding protein employed in the complex. In other embodiments, the free biotin-binding protein binds biotin less tightly than does the biotin-binding protein employed in the complex. For example, streptavidin including N10A, S14D, and S32A mutations binds biotin very weakly and can be employed as the free biotin-binding protein. Other biotin-binding proteins (e.g., mutant streptavidins) having decreased affinity for biotin are described herein; additional examples can be found in the art. In one class of embodiments, a biotin-binding protein of the invention (e.g., a mutated and/or covalently modified biotin-binding protein) is employed to immobilize a biotinylated nucleic acid (or other molecule of interest) on a biotinylated surface; any unoccupied biotin groups on the surface are then blocked by binding of free biotin-binding protein (e.g., the same biotin-binding protein of the invention, a different biotin-binding protein of the invention, or a wild type or other biotin binding protein known in the art). In a related aspect, essentially any biotin binding protein (e.g., any of the variety of biotin-binding proteins known in the art) can be employed to immobilize a biotinylated nucleic acid (or other molecule of interest) on a biotinylated surface; any unoccupied biotins on the surface are then blocked by binding of a biotin-binding protein of the invention.

Figure 4:
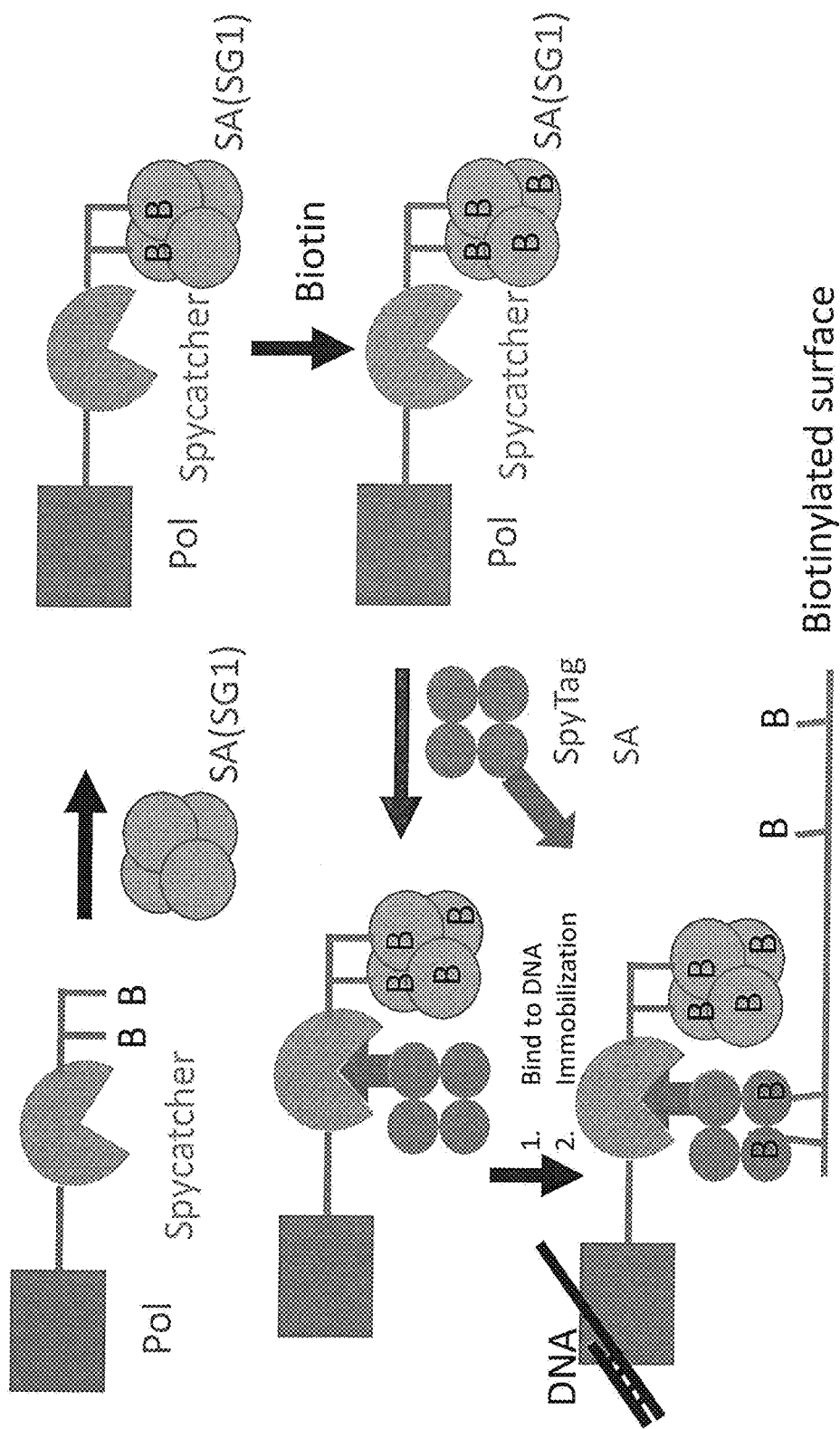
FIG. 4 schematically illustrates covalent attachment of an SG1-modified streptavidin to a polymerase that is immobilized on a solid support.

In another aspect, biotin-binding proteins of the invention can be used as accessories to immobilization of a molecule of interest. One general class of embodiments provides methods of immobilizing a molecule of interest, e.g., a polymerase or nucleic acid (including a polymerase-nucleic acid complex). In the methods, the molecule of interest is immobilized on a surface (e.g., a surface comprising a plurality of array regions, where the molecule is immobilized in the array regions). The molecule can be immobilized through essentially any technique known in the art. For example, it can be biotinylated and immobilized through binding to a biotin-binding protein (e.g., other than one of those of the invention) that is in turn immobilized on the surface, or it can be covalently attached to the surface. A biotin-binding protein of the invention (e.g., a mutated and/or covalently modified biotin-binding protein) is also immobilized on the surface. Optionally, the biotin-binding protein of the invention is covalently attached to the molecule of interest or another molecule bound thereto (directly or indirectly). In one exemplary class of embodiments, as illustrated in FIG. 4, a polymerase fused to a SpyCatcher domain and bearing a bis-biotin tag is bound to a biotin-binding protein of the invention (e.g., an SG1-modified streptavidin) through the bis-biotin tag. Any additional biotin binding sites on the biotin-binding protein are blocked by addition of biotin. The SpyCatcher domain is reacted with a SpyTag fused to another biotin-binding protein (e.g., otherwise wild type streptavidin), which binds to biotin on the surface, e.g., in the array regions. A nucleic acid can be complexed with the polymerase at essentially any convenient step, e.g., before addition of the biotin-binding protein, before immobilization, or after immobilization. (For additional information on SpyTag/SpyCatcher and similar useful systems such as SnoopTag/SnoopCatcher, see, e.g., Zakeri et al. (2012) "Peptide tag forming a rapid covalent bond to a protein, through engineering a bacterial adhesin" Proc Natl Acad Sci USA 109(12):E690-7, Veggiani et al. (2016) "Programmable polyproteams built using twin peptide superglues" Proc Natl Acad Sci USA 113(5):1202-7, Brune et al. (2017) "Dual Plug-and-Display Synthetic Assembly Using Orthogonal Reactive Proteins for Twin Antigen Immunization" Bioconjugate Chem. 28:1544-1551, and U.S. Pat. No. 9,547,003.) In other embodiments, the biotin-binding protein of the invention is immobilized on the surface independently of the molecule of interest. For example, a biotinylated polymerase can be immobilized to a biotinylated surface through an unmodified streptavidin, while a biotin-binding protein of the invention (e.g., an SG1-modified streptavidin) also binds to the biotinylated surface (e.g., in the array regions). In one class of embodiments, the biotin-binding protein has a calculated net charge of −10 or less at pH 7.4, e.g., 15 or less, −20 or less, −30 or less, −40 or less, −44 or less, −50 or less, −60 or less, −70 or less, or even 80 or less. Essentially all of the features noted above apply to these embodiments as well, as relevant, e.g., with respect to type of surface and array regions, type of biotin-binding protein, covalent modification of the biotin-binding protein, amino acid substitutions in the biotin-binding protein, exogenous features on the biotin-binding protein, and the like.

In one aspect, the invention provides methods of sequencing a nucleic acid template. In the methods, a reaction mixture is provided that includes the template, a replication initiating moiety that complexes with or is integral to the template, a nucleic acid polymerase capable of replicating at least a portion of the template using the moiety in a template-dependent polymerization reaction, and one or more nucleotides and/or nucleotide analogs. At least one of the template, the replication initiating moiety, and the polymerase is immobilized on a solid support through binding to a biotin-binding protein as described herein, e.g., a mutated and/or covalently modified biotin-binding protein. In one class of embodiments, the biotin-binding protein has a calculated net charge of −10 or less at pH 7.4, e.g., −15 or less, −20 or less, −30 or less, −40 or less, −44 or less, −50 or less, −60 or less, −70 or less, or even −80 or less.

The reaction mixture is subjected to a polymerization reaction in which the polymerase replicates at least a portion of the template in a template-dependent manner, whereby the one or more nucleotides and/or nucleotide analogs are incorporated into the resulting nucleic acid. A time sequence of incorporation of the one or more nucleotides and/or nucleotide analogs into the resulting nucleic acid is identified.

The nucleotide analogs used in the methods can comprise a first analog and a second analog (and optionally third, fourth, etc. analogs), each of which comprise different fluorescent labels. The different fluorescent labels can optionally be distinguished from one another during the step in which a time sequence of incorporation is identified. Optionally, subjecting the reaction mixture to a polymerization reaction and identifying a time sequence of incorporation are performed in a nanoscale reaction region, e.g., a nanoscale well (e.g., a ZMW) or other optically resolvable area (e.g., patches in an array or the like) or a nanoFET. Optionally, the template is a DNA template and/or the polymerase is a DNA polymerase.

Essentially all of the features noted above apply to these embodiments as well, as relevant, e.g., with respect to type of biotin-binding protein, covalent modification of the biotin-binding protein, amino acid substitutions in the biotin-binding protein, exogenous features on the biotin-binding protein, and the like.

In a related aspect, the invention provides methods of making a nucleic acid. In the methods, a reaction mixture is provided that includes a template, a replication initiating moiety that complexes with or is integral to the template, a nucleic acid polymerase capable of replicating at least a portion of the template using the moiety in a template-dependent polymerase reaction, and one or more nucleotides and/or nucleotide analogs. At least one of the template, the replication initiating moiety, and the polymerase is immobilized on a solid support through binding to a biotin-binding protein as described herein, e.g., a mutated and/or covalently modified biotin-binding protein. In one class of embodiments, the biotin-binding protein has a calculated net charge of −10 or less at pH 7.4, e.g., −15 or less, −20 or less, −30 or less, −40 or less, −44 or less, −50 or less, −60 or less, −70 or less, or even −80 or less. The mixture is reacted such that the polymerase replicates at least a portion of the template in a template-dependent manner, whereby the one or more nucleotides and/or nucleotide analogs are incorporated into the resulting nucleic acid.

The reaction mixture is optionally reacted in a nanoscale well (e.g., ZMW). The methods optionally include detecting incorporation of at least one of the nucleotides and/or nucleotide analogs. Optionally, the template is a DNA template, the polymerase is a DNA polymerase, and/or the resulting nucleic acid is a DNA.

Essentially all of the features noted above apply to these embodiments as well, as relevant, e.g., with respect to type of biotin-binding protein, covalent modification of the biotin-binding protein, amino acid substitutions in the biotin-binding protein, exogenous features on the biotin-binding protein, and the like.

Another aspect of the invention provides systems for sequencing nucleic acids that employ the biotin-binding proteins described herein. One class of embodiments provides a system for sequencing nucleic acids that includes a chip comprising a plurality of polymerase enzyme complexes bound thereto, where each polymerase enzyme complex is individually optically resolvable and where each polymerase enzyme complex comprises a polymerase enzyme, a template nucleic acid, and optionally a primer hybridized to the template nucleic acid; sequencing reagents in contact with the surface comprising reagents for carrying out nucleic acid synthesis including one or more labeled nucleotide analogs; an illumination system for illuminating the polymerase enzyme complexes; an optical detection system for detecting fluorescence from the labeled nucleotide analogs while they are interacting with the polymerase enzyme complexes; and a computer for analyzing the signals detected by the detection system to determine the sequential addition of nucleotides to a nucleic acid strand complementary to a strand of the template nucleic acid. The polymerase enzyme complexes are bound to the chip through a biotin-binding protein as described herein, e.g., a mutated and/or covalently modified biotin-binding protein. In one class of embodiments, the biotin-binding protein has a calculated net charge of −10 or less at pH 7.4, e.g., −15 or less, −20 or less, −30 or less, −40 or less, −44 or less, −50 or less, −60 or less, −70 or less, or even −80 or less. In one class of embodiments, the biotin-binding protein is a recombinant streptavidin comprising one or more amino acid substitutions as described herein. In one class of embodiments, the biotin-binding protein is a modified biotin-binding protein that comprises one or more covalently attached sulfonate moieties.

In one class of embodiments, the chip comprises a plurality of nanoscale reaction regions that comprise the polymerase enzyme complexes. For example, the chip can comprise a plurality of nanoscale wells (e.g., ZMWs) that comprise the polymerase enzyme complexes. Optionally, a plurality of the nanoscale wells include a single active polymerase enzyme complex immobilized at the base of the well. Optionally, the base of the well is selectively biotinylated for convenient immobilization.

Essentially all of the features noted above apply to these embodiments as well, as relevant, e.g., with respect to type of biotin-binding protein, covalent modification of the biotin-binding protein, amino acid substitutions in the biotin-binding protein, exogenous features on the biotin-binding protein, and the like.

Making, Isolating, and Characterizing Biotin-Binding Proteins

Generally, nucleic acids encoding a biotin-binding protein of the invention can be made by cloning, recombination, in vitro synthesis, in vitro amplification and/or other available methods. A variety of recombinant methods can be used for expressing an expression vector that encodes a biotin-binding protein of the invention. Methods for making recombinant nucleic acids and for expression and isolation of expressed products are well known and described in the art. A number of exemplary mutations and combinations of mutations, as well as strategies for design of desirable mutations, are described herein.

Additional useful references for mutation, recombinant and in vitro nucleic acid manipulation methods (including cloning, expression, PCR, and the like) include Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2017) ("Ausubel")); *PCR Protocols A Guide to Methods and Applications* (Innis et al. eds) Academic Press Inc. San Diego, Calif. (1990) ("Innis"); Berger and Kimmel, *Guide to Molecular Cloning Techniques, Methods in Enzymology volume* 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); and *The Nucleic Acid Protocols Handbook* Ralph Rapley (ed) (2000) Cold Spring Harbor, Humana Press Inc (Rapley); Chen et al. (ed) *PCR Cloning Protocols, Second Edition* (Methods in Molecular Biology, volume 192) Humana Press; and in Viljoen et al. (2005) *Molecular Diagnostic PCR Handbook* Springer, ISBN 1402034032.

In addition, a plethora of kits are commercially available for the purification of plasmids or other relevant nucleic acids from cells (see, e.g., EasyPrep™, FlexiPrep™ both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors), and selection markers for both prokaryotic and eukaryotic systems. Vectors are suitable for replication and integration in prokaryotes, eukaryotes, or both.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York)

and Atlas and Parks (eds) *The Handbook of Microbiological Media* (1993) CRC Press, Boca Raton, Fla.

Nucleic acids encoding the recombinant biotin-binding proteins of the invention are also a feature of the invention. A particular amino acid can be encoded by multiple codons, and certain translation systems (e.g., prokaryotic or eukaryotic cells) often exhibit codon bias, e.g., different organisms often prefer one of the several synonymous codons that encode the same amino acid. As such, nucleic acids of the invention are optionally "codon optimized," meaning that the nucleic acids are synthesized to include codons that are preferred by the particular translation system being employed to express the biotin-binding protein. For example, when it is desirable to express the biotin-binding protein in a bacterial cell (or even a particular strain of bacteria), the nucleic acid can be synthesized to include codons most frequently found in the genome of that bacterial cell, for efficient expression of the protein. A similar strategy can be employed when it is desirable to express the biotin-binding protein in a eukaryotic cell, e.g., the nucleic acid can include codons preferred by that eukaryotic cell.

A variety of protein isolation and detection methods are known and can be used to isolate biotin-binding proteins, e.g., from recombinant cultures of cells expressing the recombinant biotin-binding proteins of the invention. A variety of protein isolation and detection methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods, 2nd Edition* Wiley-Liss, NY; Walker (1996) *The Protein Protocols Handbook* Humana Press, NJ; Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3rd Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Additional details regarding protein purification and detection methods can be found in Satinder Ahuja ed., *Handbook of Bioseparations*, Academic Press (2000). Expression, isolation, and multimer formation for various biotin-binding proteins has been described in the literature. For example, for expression of streptavidin and for formation of mixed multimers, see, e.g., "Expression of a cloned streptavidin gene in *Escherichia coli*" Proc Natl Acad Sci USA 87:142-6 and Fairhead et al. (2014) "SpyAvidin hubs enable precise and ultrastable orthogonal nanoassembly" J. Am. Chem. Soc. 136: 12355-12363.

Mutating Biotin-Binding Proteins

Various types of mutagenesis are optionally used in the present invention, e.g., to modify biotin-binding proteins to produce variants, e.g., in accordance with structural models and model predictions as discussed above, or using random or semi-random mutational approaches. In general, any available mutagenesis procedure can be used for making biotin-binding protein mutants. Such mutagenesis procedures optionally include selection of mutant nucleic acids and polypeptides for one or more activity of interest (e.g., ability to immobilize nucleic acids, biotin binding, etc.). Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting biotin-binding protein for mutation can be any of those noted herein or known in the art, including available streptavidin mutations such as those identified, e.g., in Lawrence et al. (2007) "Supercharged proteins can impart unusual resilience" J Am Chem Soc 129:10110-10112 and U.S. patent application publication 2017/0088592.

Optionally, mutagenesis can be guided by known information from a naturally occurring biotin-binding protein molecule, or of a known altered or mutated biotin-binding protein (e.g., using an existing mutant biotin-binding protein as noted in the preceding references), e.g., sequence, sequence comparisons, physical properties, crystal structure and/or the like as discussed above. However, in another class of embodiments, modification can be essentially random (e.g., as in classical or "family" DNA shuffling, see, e.g., Crameri et al. (1998) "DNA shuffling of a family of genes from diverse species accelerates directed evolution" Nature 391:288-291).

Additional information on mutation formats is found in: Sambrook, Ausubel, and Innis, all supra. The following publications and references cited within provide additional detail on mutation formats: Arnold, Protein engineering for unusual environments, Current Opinion in Biotechnology 4:450-455 (1993); Bass et al., Mutant Trp repressors with new DNA-binding specificities, Science 242:240-245 (1988); Bordo and Argos (1991) Suggestions for "Safe" Residue Substitutions in Site-directed Mutagenesis 217:721-729; Botstein & Shortle, Strategies and applications of in vitro mutagenesis, Science 229:1193-1201 (1985); Carter et al., Improved oligonucleotide site-directed mutagenesis using M13 vectors, Nucl. Acids Res. 13: 4431-4443 (1985); Carter, Site-directed mutagenesis, Biochem. J. 237:1-7 (1986); Carter, Improved oligonucleotide-directed mutagenesis using M13 vectors, Methods in Enzymol. 154: 382-403 (1987); Dale et al., Oligonucleotide-directed random mutagenesis using the phosphorothioate method, Methods Mol. Biol. 57:369-374 (1996); Eghtedarzadeh & Henikoff, Use of oligonucleotides to generate large deletions, Nucl. Acids Res. 14:5115 (1986); Fritz et al., Oligonucleotide-directed construction of mutations: a gapped duplex DNA procedure without enzymatic reactions in vitro, Nucl. Acids Res. 16: 6987-6999 (1988); Grundström et al., Oligonucleotide-directed mutagenesis by microscale 'shot-gun' gene synthesis, Nucl. Acids Res. 13: 3305-3316 (1985); Hayes (2002) Combining Computational and Experimental Screening for rapid Optimization of Protein Properties PNAS 99(25) 15926-15931; Kunkel, The efficiency of oligonucleotide directed mutagenesis, in Nucleic Acids & Molecular Biology (Eckstein, F. and Lilley, D. M. J. eds., Springer Verlag, Berlin)) (1987); Kunkel, Rapid and efficient site-specific mutagenesis without phenotypic selection, Proc. Natl. Acad. Sci. USA 82:488-492 (1985); Kunkel et al., Rapid and efficient site-specific mutagenesis without phenotypic selection, Methods in Enzymol. 154, 367-382 (1987); Kramer et al., The gapped duplex DNA approach to oligonucleotide-directed mutation construction, Nucl. Acids Res. 12: 9441-9456 (1984); Kramer & Fritz Oligonucleotide-directed construction of mutations via gapped duplex DNA, Methods in Enzymol. 154:350-367 (1987); Kramer et al., Point Mismatch Repair, Cell 38:879-887 (1984); Kramer et al., Improved enzymatic in vitro reactions in the gapped duplex DNA approach to oligonucleotide-directed construction of mutations, Nucl. Acids Res. 16: 7207 (1988); Ling et al., Approaches to DNA mutagenesis: an overview, Anal Biochem. 254(2): 157-178 (1997); Lorimer and Pastan Nucleic Acids Res. 23, 3067-8 (1995); Mandecki, Oligonucleotide-directed double-strand break repair in plasmids of *Escherichia coli*: a method for site-specific mutagenesis, Proc. Natl. Acad. Sci. USA, 83:7177-7181 (1986); Nakamaye & Eckstein, Inhibition of restriction endonuclease Nci I cleavage by phosphorothioate groups and its application to oligonucleotide-directed mutagenesis, Nucl. Acids Res. 14: 9679-9698 (1986); Nambiar et al., Total synthesis and cloning of a gene coding for the ribonuclease S protein, Science 223: 1299-1301 (1984); Sakamar and Khorana, Total synthesis and expression of a gene for the a-subunit of bovine rod outer segment guanine nucleotide-binding protein (transducin), Nucl. Acids Res. 14: 6361-6372 (1988); Sayers et al., Y-T Exonucleases in phosphorothioate-based oligonucleotide-directed mutagenesis, Nucl. Acids Res. 16:791-802 (1988); Sayers et al., Strand specific cleavage of phosphorothioate-containing DNA by reaction with restriction endonucleases in the presence of ethidium bromide, (1988) Nucl. Acids Res. 16: 803-814; Sieber, et al., Nature Biotechnology, 19:456-460 (2001); Smith, In vitro mutagenesis, Ann. Rev. Genet. 19:423-462 (1985); Methods in Enzymol. 100: 468-500 (1983); Methods in Enzymol. 154: 329-350 (1987); Stemmer, Nature 370, 389-91 (1994); Taylor et al., The use of phosphorothioate-modified DNA in restriction enzyme reactions to prepare nicked DNA, Nucl. Acids Res. 13: 8749-8764 (1985); Taylor et al., The rapid generation of oligonucleotide-directed mutations at high frequency using phosphorothioate-modified DNA, Nucl. Acids Res. 13: 8765-8787 (1985); Wells et al., Importance of hydrogen-bond formation in stabilizing the transition state of subtilisin, Phil. Trans. R. Soc. Lond. A 317: 415-423 (1986); Wells et al., Cassette mutagenesis: an efficient method for generation of multiple mutations at defined sites, Gene 34:315-323 (1985); Zoller & Smith, Oligonucleotide-directed mutagenesis using M13-derived vectors: an efficient and general procedure for the production of point mutations in any DNA fragment, Nucleic Acids Res. 10:6487-6500 (1982); Zoller & Smith, Oligonucleotide-directed mutagenesis of DNA fragments cloned into M13 vectors, Methods in Enzymol. 100:468-500 (1983); Zoller & Smith, Oligonucleotide-directed mutagenesis: a simple method using two oligonucleotide primers and a single-stranded DNA template, Methods in Enzymol. 154:329-350 (1987); Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296. Additional details on many of the above methods can be found in Methods in Enzymology Volume 154, which also describes useful controls for trouble-shooting problems with various mutagenesis methods.

Determining Kinetic Parameters

The biotin-binding proteins of the invention can be screened or otherwise tested to determine whether the biotin-binding protein displays activity for or with a biotin or biotin analog as compared to a parental biotin-binding protein (e.g., a corresponding wild type or available mutant biotin-binding protein from which the recombinant or modified biotin-binding protein of the invention was derived). For example, $k_{off}$, $k_{on}$, and/or $K_d$ of the recombinant or modified biotin-binding protein for biotin (or an analog) can be determined. In many embodiments, high biotin affinity is desired for the modified or recombinant biotin-binding protein. In such embodiments, the modified or recombinant biotin-binding protein can exhibit a $K_d$ that is no more than 100 times (e.g., no more than 10 times) the $K_d$ exhibited by the parental protein, under equivalent reaction conditions. In other embodiments, however, weaker biotin binding affinity can be desirable (e.g., where more readily reversible biotin binding is desired). Similarly, the modified or recombinant biotin-binding protein optionally exhibits a $k_{off}$ that is no more than 100 times (e.g., no more than 10 times) the $k_{off}$ exhibited by the parental protein, or a $k_{on}$ that is no less than 0.01 times (e.g., no less than 0.1 times) the $k_{on}$ exhibited by the parental protein, under equivalent reaction conditions. $K_d$, $k_{off}$, and $k_{on}$ can be determined using techniques known in the art, for example, binding or competitive binding assays.

For a more thorough discussion of binding kinetics, see, e.g., Berg, Tymoczko, and Stryer (2002) *Biochemistry, Fifth Edition*, W. H. Freeman; Creighton (1984) *Proteins: Structures and Molecular Principles*, W. H. Freeman; and Fersht (1985) *Enzyme Structure and Mechanism, Second Edition*, W. H. Freeman.

In one aspect, the activity of the proteins of the invention is compared with a given parental biotin-binding protein. For example, in the case of a recombinant streptavidin derived from a parental wild type streptavidin, the biotin binding affinity (e.g., $K_d$, $k_{off}$, or $k_{on}$) of the recombinant streptavidin would be compared to that of the wild type streptavidin. Such comparisons are made under equivalent reaction conditions, e.g., equal concentrations of the parental and recombinant (or modified) biotin-binding protein, equal biotin concentrations, equivalent solution conditions (pH, salt concentration, presence of divalent cations, etc.), temperature, and the like. While the foregoing may be used as a characterization tool, it in no way is intended as a specifically limiting reaction of the invention.

Screening Biotin-Binding Proteins

Screening or other protocols can be used to determine whether a biotin-binding protein displays a desired activity, e.g., nucleic acid immobilization, biotin binding, etc., optionally as compared to a parental DNA biotin-binding protein. Performance of a recombinant or modified biotin-binding protein in a sequencing reaction, e.g., a single molecule sequencing reaction, can be examined to assay properties such as speed, pulse width, interpulse distance, accuracy, readlength, etc.

In one desirable aspect, a library of recombinant or modified biotin-binding proteins can be made and screened for these properties. For example, a plurality of members of the library can be made to include one or more mutation that alters (e.g., decreases) net charge (e.g., where different members include different mutations or different combinations of mutations), and the library can then be screened for the properties of interest (e.g., biotin binding, performance in immobilization of a molecule of interest, sequencing performance, etc.). In general, the library can be screened to identify at least one member comprising an activity of interest.

Libraries of biotin-binding proteins can be either physical or logical in nature. Moreover, any of a wide variety of library formats can be used. For example, biotin-binding proteins can be fixed to solid surfaces in arrays of proteins. Similarly, liquid phase arrays of biotin-binding proteins (e.g., in microwell plates) can be constructed for convenient high-throughput fluid manipulations of solutions comprising biotin-binding proteins. Liquid, emulsion, or gel-phase libraries of cells that express recombinant biotin-binding proteins can also be constructed, e.g., in microwell plates, or on agar plates. Phage display libraries of biotin-binding proteins or biotin-binding protein domains (e.g., including the active site region or interdomain stability regions) can be produced. Likewise, yeast display libraries can be used. Instructions in making and using libraries can be found, e.g., in Sambrook, Ausubel, and Berger, referenced herein.

For the generation of libraries involving fluid transfer to or from microtiter plates, a fluid handling station is optionally used. Several "off the shelf" fluid handling stations for performing such transfers are commercially available, including e.g., the Zymate systems from Caliper Life Sciences (Hopkinton, Mass.) and other stations which utilize automatic pipettors, e.g., in conjunction with the robotics for plate movement (e.g., the ORCA® robot, which is used in a variety of laboratory systems available, e.g., from Beckman Coulter, Inc. (Fullerton, Calif.).

In an alternate embodiment, fluid handling is performed in microchips, e.g., involving transfer of materials from microwell plates or other wells through microchannels on the chips to destination sites (microchannel regions, wells, chambers or the like). Commercially available microfluidic systems include those from Hewlett-Packard/Agilent Technologies (e.g., the HP2100 bioanalyzer) and the Caliper High Throughput Screening System. The Caliper High Throughput Screening System provides one example interface between standard microwell library formats and Labchip technologies. RainDance Technologies' nanodroplet platform provides another method for handling large numbers of spatially separated reactions. Furthermore, the patent and technical literature includes many examples of microfluidic systems which can interface directly with microwell plates for fluid handling.

Nucleic Acid and Polypeptide Sequences and Variants

One of skill will appreciate that many variants of the disclosed sequences are included in the invention. For example, conservative variations of the disclosed sequences that yield a functionally similar sequence are included in the invention. Polynucleotide sequences that encode a disclosed polypeptide sequence are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence (other than residues noted, e.g., in Table 1 or elsewhere herein, as being relevant to a feature or property of interest for that sequence) are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid, while retaining the relevant mutational feature (for example, the conservative substitution can be of a residue distal to the active site region, or distal to an interdomain stability region). Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional or tagging sequence (introns in the nucleic acid, poly His or similar sequences in the encoded polypeptide, etc.), is a conservative variation of the basic nucleic acid or polypeptide.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

TABLE 2

Conservative amino acid substitutions

| Nonpolar and/or Aliphatic Side Chains | Polar, Uncharged Side Chains | Aromatic Side Chains | Positively Charged Side Chains | Negatively Charged Side Chains |
|---|---|---|---|---|
| Glycine Alanine Valine Leucine Isoleucine Proline | Serine Threonine Cysteine Methionine Asparagine Glutamine | Phenylalanine Tyrosine Tryptophan | Lysine Arginine Histidine | Aspartate Glutamate |

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a biotin-binding protein, or the amino acid sequence of a biotin-binding protein) refers to two or more sequences or subsequences that have at least about 60%, about 80%, about 85%, about 90%, about 95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 75%, 80%, 85%, 90%, 95%, 97%, 98%, or 99% or more identity, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2012).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Templates and Other Nucleic Acids

The practice of the inventions described in the present disclosure may employ, unless otherwise indicated, conventional techniques and descriptions of organic chemistry, polymer technology, molecular biology (including recombinant techniques), cell biology, biochemistry, and immunology, which are within the skill of the art. Such conventional techniques include nucleic acid synthesis, isolation and/or manipulation, polymer array synthesis, hybridization, ligation, phage display, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Sambrook et al., Molecular Cloning—A Laboratory Manual (3rd Ed.), Vol. 1-3, Cold Spring Harbor Laboratory, Cold Spring Harbor, N.Y., 2000, Current Protocols in Molecular Biology, F. M. Ausubel et al., eds., Current Protocols, a joint venture between Greene Publishing Associates, Inc. and John Wiley & Sons, Inc., (supplemented through 2017), Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3rd Ed., W. H. Freeman Pub., New York, N.Y. and Berg et al. (2002)

Biochemistry, 5th Ed., W. H. Freeman Pub., New York, N.Y., all of which are herein incorporated in their entirety by reference for all purposes.

The nucleic acids employed in the practice of the invention can be fully or partially double-stranded or can be single-stranded. Suitable nucleic acids include, but are not limited to, SMRTbells™ (circular nucleic acids having a double-stranded central region and single-stranded hairpin ends), double-stranded circular DNA molecules (e.g., nicked or gapped double-stranded circular DNA molecules, e.g., nicked or gapped plasmids), long hairpins, and linear molecules (e.g., genomic DNA fragments).

Nucleic acids, including template nucleic acids, can be prepared using techniques well known in the art, from essentially any desired sample. For further discussion of circular templates, including, e.g., simple circles and SMRTbells' (circular nucleic acids having a double-stranded central region and single-stranded hairpin ends), see, e.g., U.S. Pat. No. 8,236,499 "Methods and Compositions for Nucleic Acid Sample Preparation," U.S. Pat. No. 8,153,375 "Compositions and Methods for Nucleic Acid Sequencing," and Travers et al. (2010) Nucl. Acids Res. 38(15):e159, each of which is incorporated herein by reference in its entirety for all purposes.

Any of the methods, compositions, systems, and complexes described herein can include template nucleic acid molecules, often as part of the polymerase enzyme complexes described herein. In general, a template nucleic acid is a molecule for which the complementary sequence is (or can be) synthesized in a polymerase reaction. As will be appreciated, template sequences can be of any length or structure. In some cases, the template nucleic acid is linear; in some cases, the template nucleic acid is circular. The template nucleic acid can be DNA, RNA, and/or a non-natural RNA or DNA analog. Any nucleic acid that is suitable for replication by a polymerase enzyme can be used as a template in the methods and systems described herein.

In some embodiments, the nucleic acids used in methods and compositions of the present invention comprise nucleic acids obtained from a sample. The sample may comprise any number of things, including, but not limited to, bodily fluids (including, but not limited to, blood, urine, serum, lymph, saliva, anal and vaginal secretions, perspiration and semen) and cells of virtually any organism, with mammalian samples being preferred and human samples being particularly preferred; environmental samples (including, but not limited to, air, agricultural, water and soil samples); biological warfare agent samples; research samples (e.g., in the case of nucleic acids, the sample may be the products of an amplification reaction, including both target and signal amplification, such as PCR amplification reactions; purified samples, such as purified genomic DNA, RNA preparations, raw samples (bacteria, virus, genomic DNA, etc.); as will be appreciated by those in the art, virtually any experimental manipulation may have been done on the samples.

In further embodiments, nucleic acid molecules are obtained from a sample and fragmented for use in (or prior to use in) methods of the invention, e.g., as template nucleic acids. The fragments may be single or double stranded and may further be modified in accordance with any methods known in the art and described herein. Nucleic acids may be generated by fragmenting source nucleic acids, such as genomic DNA, using any method known in the art. In one embodiment, shear forces during lysis and extraction of genomic DNA generate fragments in a desired range. Also encompassed by the present disclosure are methods of fragmentation utilizing restriction endonucleases.

As will be appreciated, the nucleic acids may be generated from a source nucleic acid, such as genomic DNA, by fragmentation to produce fragments of a specific size. The nucleic acids can be, for example, from about 10 to about 50,000 nucleotides in length, e.g., 10-20,000, 50-1000, 10-100, 50-100, 50-300, 100-200, 200-300, 50-400, 50-600, 100-400, 200-400, 400-500, 300-600, 400-600, 500-600, 50-1000, 100-1000, 200-1000, 300-1000, 400-1000, 500-1000, 600-1000, 700-1000, 700-900, 700-800, 800-1000, 900-1000, 200-2000, 1500-2000, 1750-2000, 50-2000, 100-25000, 200-24000, 300-23000, 400-22000, 500-21000, 600-20000, 700-19000, 800-18000, 900-17000, 1000-16000, 1100-15000, 1200-14000, 1300-13000, 1400-12000, 1500-11000, 1600-10000, 1700-9000, 1800-8000, 1900-7000, 2000-6000, 2100-5000, 2200-4000, 2300-3000, 5000-20000, 10000-30000, 12000-28000, 14000-26000, 16000-24000, 18000-22000, or 19000-20000 nucleotides in length. In some embodiments, the nucleic acids are at least 5000, 10000, 15000, 20000, 25000, 30000, 40000, 50000, 60000, 70000, 80000, 90000, 100,000, 120,000, 130,000, 140,000, 150,000, 200,000, 500,000, or 1,000,000 nucleotides in length. In some embodiments, the nucleic acids are part of polymerase-template complexes. In some embodiments, the nucleic acid templates are themselves further hybridized to primers.

In some cases, the template sequence may be a linear single or double stranded nucleic acid sequence. In still other embodiments, the template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220,674, filed Jul. 25, 2008, and alternate functional circular constructs are also described in US Pat. App. Pub. No. 20090298075, the full disclosures of each of which are incorporated herein by reference in their entirety for all purposes and in particular for all teachings related to template nucleic acid constructs. Briefly, such alternate constructs include template sequences that possess a central double stranded portion that is linked at each end by an appropriate linking oligonucleotide, such as a hairpin loop segment (SMRTbells™). Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

In some aspects, the template nucleic acid used in the compositions of the present invention includes: a double stranded nucleic acid segment having a first and second end; a first hairpin oligonucleotide connecting each strand of the single template nucleic acid at the first end; and a second hairpin oligonucleotide connecting each strand of the single template nucleic acid at the second end. In some embodiments, the first hairpin and second hairpin oligonucleotide are identical. In other embodiments, the first hairpin and second hairpin oligonucleotides are not identical—in other words, the template nucleic acid, despite being an alternate circular construct, is nevertheless asymmetrical. In further embodiments, the first hairpin oligonucleotide includes a primer binding site whereas the second hairpin oligonucleotide includes a capture adapter (or vice versa). The capture adapter is generally of a sequence that can be used to enrich a population for the hairpins of choice—for example, in some embodiments, the capture adapter comprises a polyA sequence, thereby allowing capture using beads or column chromatography utilizing polyT sequences. In some embodiments, the capture adapter comprises at least one methoxy residue. In some embodiments, the capture adapter is complementary to an oligonucleotide attached to a bead, which can in further embodiments be a magnetic bead that can be used to enrich a population for template nucleic acids containing the capture adapter. In some embodiments in which the population of templates includes templates with different adapters or in which each template comprises a different adapter at each end, different beads can be used which contain oligonucleotides complementary to the different adapters. Thus, for templates with two different adapters, two different beads can be used. For populations containing a plurality of different adapters, a concomitant number of different types of beads can be used that are directed to those adapters. In other embodiments, the same bead can contain different oligonucleotides complementary to the different adapters in the population of templates, such that the same bead can capture different adapters (and their associated templates). In some embodiments, the first or second hairpin comprises a self-primed adapter sequence in which the primer is part of the adapter. In such embodiments, an additional oligonucleotide primer is not needed to allow a polymerase molecule to begin replicating the template. In some embodiments, the nucleic acid template contains only a single hairpin at one end or the other.

The polymerase enzymes of use in the methods and compositions described herein generally require a primer. While in most cases an oligonucleotide primer is used, in some cases a protein such as a terminal protein can acts as a primer. Oligonucleotide primers are generally complementary to a portion of the template nucleic acid. The primers can comprise naturally occurring RNA or DNA oligonucleotides. The primers may also be synthetic analogs. The primers may have alternative backbones as described above. The primers may also have other modifications, such as the inclusion of heteroatoms, the attachment of labels, such as dyes, or substitution with functional groups which will still allow for base pairing and for recognition by the enzyme. Primers can select tighter binding primer sequences, e.g., GC rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template. The primers can also be selected to influence the kinetics of the polymerase reaction through the use of length, nucleotide content, and/or any of the modifications discussed above.

In other embodiments, self-priming templates are employed. For example, a SMRTbell™ including a self-primed adapter sequence can be employed, as noted above. As another example, a double-stranded template including at least one nick or gap can be employed (e.g., a nicked or gapped double-stranded plasmid).

Nucleic Acid Polymerases

Many of the methods and compositions of the present disclosure utilize polymerase enzymes (also referred to herein as "polymerases"). Any suitable polymerase enzyme can be used in the systems and methods disclosed herein. Suitable polymerases include DNA dependent DNA polymerases, DNA dependent RNA polymerases, RNA dependent DNA polymerases (reverse transcriptases), and RNA dependent RNA polymerases. In certain embodiments, the polymerases used in the methods and compositions of the present invention are strand-displacing polymerases.

As disclosed in further detail herein, polymerases of use in the presently disclosed methods may include modifications that improve certain characteristics of the enzyme, including processivity, resistance to photodamage, and conduciveness to immobilization. In certain aspects, polymerases used in the methods and systems disclosed herein include a linker, motif (e.g., a biotin ligase recognition sequence), or domain through which the polymerases (and any other molecules they are complexed with, such as template nucleic acids) can be immobilized onto a surface, e.g., through binding to a biotin-binding protein of the invention.

DNA polymerases are sometimes classified into six main groups based upon various phylogenetic relationships, e.g., with E. coli Pol I (class A), E. coli Pol II (class B), E. coli Pol III (class C), Euryarchaeotic Pol II (class D), human Pol beta (class X), and E. coli UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures of homologous polymerases. For example, the crystal structure of Φ29 polymerase is available.

In addition to wild type polymerases, chimeric polymerases made from a mosaic of different sources can be used. For example, Φ29 polymerases made by taking sequences from more than one parental polymerase into account can be used as a starting point for mutation to produce the polymerases used in methods described herein. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. For example, polymerases have been modified to confer improvements in specificity, processivity, and improved retention time of labeled nucleotides in polymerase-DNA-nucleotide complexes (e.g., WO 2007/076057 Polymerases For Nucleotide Analogue Incorporation by Hanzel et al. and WO 2008/051530 Polymerase Enzymes And Reagents For Enhanced Nucleic Acid Sequencing by Rank et al.), to alter branch fraction and translocation (e.g., US Pub. No. 20100075332 entitled "Engineering Polymerases And Reaction Conditions For Modified Incorporation Properties"), to increase photostability (e.g., US Pub. No. 20100093555 entitled "Enzymes Resistant to Photodamage"), and to improve surface-immobilized enzyme activities (e.g., WO 2007/075987 Active Surface Coupled Polymerases by Hanzel et al. and WO 2007/076057 Protein Engineering Strategies To Optimize Activity Of Surface Attached Proteins by Hanzel et al.). In some cases, the polymerase is modified in order to more effectively incorporate desired nucleotide analogs, e.g. analogs having four or more phosphates in their polyphosphate chain. Enzymes mutated to more readily accept nucleotide analogs having such properties are described, for example in the applications described above and in US 20120034602 Recombinant Polymerases for Improved Single Molecule Sequencing; US 20100093555 Enzymes Resistant to Photodamage; US 20110189659 Generation of Modified Polymerases for Improved Accuracy in Single Molecule Sequencing; US 20100112645 Generation of Modified Polymerases for Improved Accuracy in Single Molecule Sequencing; US 2008/0108082 Polymerase enzymes and reagents for enhanced nucleic acid sequencing; and US 20110059505 Polymerases for Nucleotide Analogue Incorporation. Each of these references is incorporated herein by reference in its entirety for all purposes.

Many polymerases that are suitable, e.g., for use in sequencing, labeling and amplification technologies, are available. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot) com provides comparisons of many different commercially available polymerases.

DNA polymerases that can be employed, e.g., in single molecule sequencing or other techniques of use with methods and compositions of the invention, include, e.g., Taq polymerases, exonuclease deficient Taq polymerases, E. coli DNA Polymerase 1, Klenow fragment, reverse transcriptases, Φ29-related polymerases including wild type Φ29 polymerase and derivatives of such polymerases such as exonuclease deficient forms, T7 DNA polymerase, T5 DNA polymerase, an RB69 polymerase, etc.

In one aspect, the polymerase of use in the methods and compositions described herein is a modified Φ29-type DNA polymerase. For example, the modified recombinant DNA polymerase can be homologous to a wild type or exonuclease deficient Φ29 DNA polymerase, e.g., as described in U.S. Pat. Nos. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases (including polymerases with two biotinylation sites that constitute a bis-biotin tag) are described, for example, in U.S. Patent application publications 2007-0196846, 2008-0108082, 2010-0075332, 2010-0093555, 2010-0112645, 2011-0189659, 2012-0034602, 2013-0217007, 2014-0094374, and 2014-0094375, each of which is incorporated herein by reference in its entirety for all purposes.

In further embodiments, the polymerase enzyme used in the methods described herein includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Many native DNA polymerases have a proof-reading exonuclease function which can yield substantial data analysis problems in processes that utilize real time observation of incorporation events as a method of identifying sequence information, e.g., single molecule sequencing applications. Even where exonuclease activity does not introduce such problems in single molecule sequencing, reduction of exonuclease activity can be desirable since it can increase accuracy (in some cases at the expense of readlength).

Accordingly, polymerases for use in the above techniques optionally include one or more mutations (e.g., substitutions, insertions, and/or deletions) relative to the parental polymerase that reduce or eliminate endogenous exonuclease activity. For example, relative to wild type Φ29 DNA polymerase, one or more of positions N62, D12, E14, T15, H61, D66, D169, K143, Y148, and H149 is optionally mutated to reduce exonuclease activity in a recombinant Φ29 polymerase. Exemplary mutations that can reduce exonuclease activity in a recombinant Φ29 polymerase include, e.g., N62D, N62H, D12A, T15I, E14I, E14A, D66A, K143D, D145A and D169A substitutions, as well as addition of an exogenous feature at the C-terminus (e.g., a polyhistidine tag). See, e.g., US patent application publication 2014/0094375, incorporated herein by reference in its entirety for all purposes, for the sequence of wild type Φ29 polymerase.

Nucleotide Analogs

As discussed, various polymerases can incorporate one or more nucleotide analogs into a growing oligonucleotide chain. Upon incorporation, the analog can leave a residue that is the same as or different than a natural nucleotide in the growing oligonucleotide (the polymerase can incorporate any non-standard moiety of the analog, or can cleave it off during incorporation into the oligonucleotide). A "nucleotide analog" herein is a compound, that, in a particular application, functions in a manner similar or analogous to a naturally occurring nucleoside triphosphate (a "nucleotide"), and does not otherwise denote any particular structure. A nucleotide analog is an analog other than a standard naturally occurring nucleotide, i.e., other than A, G, C, T, or U, though upon incorporation into the oligonucleotide, the resulting residue in the oligonucleotide can be the same as (or different from) an A, G, C, T, or U residue.

Many nucleotide analogs are available and can be incorporated by polymerases. These include analog structures with core similarity to naturally occurring nucleotides, such as those that comprise one or more substituent on a phosphate, sugar, or base moiety of the nucleoside or nucleotide relative to a naturally occurring nucleoside or nucleotide. In one embodiment, the nucleotide analog includes three phosphate containing groups; for example, the analog can be a labeled nucleoside triphosphate analog and/or an α-thiophosphate nucleotide analog having three phosphate groups. In one embodiment, a nucleotide analog can include one or more extra phosphate containing groups, relative to a nucleoside triphosphate. For example, a variety of nucleotide analogs that comprise, e.g., from 4-6 or more phosphates are described in detail in US patent application publication 2007-0072196, incorporated herein by reference in its entirety for all purposes. Other exemplary useful analogs, including tetraphosphate and pentaphosphate analogs, are described in U.S. Pat. No. 7,041,812, incorporated herein by reference in its entirety for all purposes.

For example, the analog can include a labeled compound of the formula:

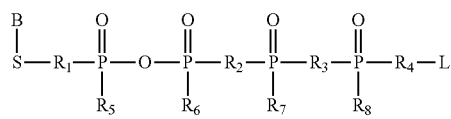

wherein B is a nucleobase (and optionally includes a label); S is selected from a sugar moiety, an acyclic moiety or a carbocyclic moiety (and optionally includes a label); L is an optional detectable label; $R_1$ is selected from O and S; $R_2$, $R_3$ and $R_4$ are independently selected from O, NH, S, methylene, substituted methylene, C(O), C(CH$_2$), CNH$_2$, CH$_2$CH$_2$, and C(OH)CH$_2$R where R is 4-pyridine or 1-imidazole, provided that $R_4$ may additionally be selected from

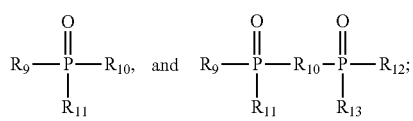

$R_5$, $R_6$, $R_7$, $R_8$, $R_{11}$ and $R_{13}$ are, when present, each independently selected from O, BH$_3$, and S; and $R_9$, $R_{10}$ and $R_{12}$ are independently selected from O, NH, S, methylene, substituted methylene, CNH$_2$, CH$_2$CH$_2$, and C(OH)CH$_2$R where R is 4-pyridine or 1-imidazole. In some cases, phosphonate analogs may be employed as the analogs, e.g., where one of $R_2$, $R_3$, $R_4$, $R_9$, $R_{10}$ or $R_{12}$ are not O, e.g., they are methyl etc. See, e.g., US patent application publication 2007-0072196, previously incorporated herein by reference in its entirety for all purposes.

The base moiety incorporated into the analog is generally selected from any of the natural or non-natural nucleobases or nucleobase analogs, including, e.g., purine or pyrimidine bases that are routinely found in nucleic acids and available nucleic acid analogs, including adenine, thymine, guanine, cytosine, uracil, and in some cases, inosine. As noted, the base optionally includes a label moiety. For convenience, nucleotides and nucleotide analogs are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

In the analogs, the S group is optionally a sugar moiety that provides a suitable backbone for a synthesizing nucleic acid strand. For example, the sugar moiety is optionally selected from a D-ribosyl, 2' or 3' D-deoxyribosyl, 2',3'-D-dideoxyribosyl, 2', 3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties can be incorporated as the "S" group in place of a sugar moiety, including, e.g., those described in U.S. Patent Application Publication No. 2003/0124576, which is incorporated herein by reference in its entirety for all purposes.

For most cases, the phosphorus containing chain in the analogs, e.g., a triphosphate in conventional NTPs, is preferably coupled to the 5' hydroxyl group, as in natural nucleoside triphosphates. However, in some cases, the phosphorus containing chain is linked to the S group by the 3' hydroxyl group.

L generally refers to a detectable labeling group that is coupled to the terminal phosphorus atom via the R4 (or $R_{10}$ or $R_{12}$ etc.) group. The labeling groups employed in the analogs of the invention may comprise any of a variety of detectable labels. Detectable labels generally denote a chemical moiety that provides a basis for detection of the analog compound separate and apart from the same compound lacking such a labeling group. Examples of labels include, e.g., optical labels, e.g., labels that impart a detectable optical property to the analog, electrochemical labels, e.g., labels that impart a detectable electrical or electrochemical property to the analog, and physical labels, e.g., labels that impart a different physical or spatial property to the analog, e.g., a mass tag or molecular volume tag. In some cases individual labels or combinations may be used that impart more than one of the aforementioned properties to the analogs of the invention.

Optionally, the labeling groups incorporated into the analogs comprise optically detectable moieties, such as luminescent, chemiluminescent, fluorescent, fluorogenic, chromophoric and/or chromogenic moieties, with fluorescent and/or fluorogenic labels being preferred. A variety of different label moieties are readily employed in nucleotide analogs. Such groups include, e.g., fluorescein labels, rhodamine labels, cyanine labels (i.e., Cy3, Cy5, and the like, generally available from the Amersham Biosciences division of GE Healthcare), and the Alexa family of fluorescent dyes and other fluorescent and fluorogenic dyes available from Molecular Probes/Invitrogen, Inc. and described in 'The Handbook—A Guide to Fluorescent Probes and Labeling Technologies, Eleventh Edition' (2010) (available from Invitrogen, Inc./Molecular Probes). A variety of other fluorescent and fluorogenic labels for use with nucleoside polyphosphates, and which would be applicable to the nucleotide analogs incorporated by polymerases, are described in, e.g., U.S. Patent Application Publication No. 2003/0124576, previously incorporated herein by reference in its entirety for all purposes.

Additional details regarding labels, analogs, and methods of making such analogs can be found in US patent application publication 2007-0072196, WO 2007/041342 Labeled Nucleotide Analogs and Uses Therefor, WO 2009/114182 Labeled Reactants and Their Uses, US patent application publication 2009-0208957 Alternate Labelling Strategies for Single Molecule Sequencing, U.S. patent application Ser. No. 13/218,412 Functionalized Cyanine Dyes, U.S. patent application Ser. No. 13/218,395 Functionalized Cyanine Dyes, U.S. patent application Ser. No. 13/218,428 Cyanine Dyes, U.S. patent application Ser. No. 13/218,382 Scaffold-Based Polymerase Enzyme Substrates, US patent application publication 2010-0167299 Phospholink Nucleotides for Sequencing Applications, US patent application publication 2010-0152424 Modular Nucleotide Compositions and Uses Therefor, U.S. patent application 61/599,149 Polymerase Enzyme Substrates with Protein Shield, U.S. patent application Ser. No. 13/767,619 "Polymerase Enzyme Substrates with Protein Shield," U.S. patent application Ser. No. 14/452,497 "Protected Fluorescent Reagent Compounds," U.S. Pat. Nos. 7,968,702 and 9,062,091, and U.S. patent application publications 2017/0145495, 2017/0145496, and 2017/0145502, each of which is incorporated herein by reference in its entirety for all purposes.

Nucleic Acid Sequencing

The methods, systems, and compositions of the invention are particularly useful for single molecule sequencing methods, and specifically single molecule sequencing by incorporation in real time, because the methods and compositions of the present disclosure provide a way to increase survival of surface-associated nucleic acid/polymerase complexes in such methods Immobilization of nucleic acids into a high density array of reaction regions can be accomplished using biotin-binding proteins of the invention. In specific embodiments, the methods result in loading an array of reaction regions such that a single nucleic acid (or a single polymerase enzyme complexed with a nucleic acid template and optionally a primer) occupies each of a plurality of the reaction regions, thus allowing for single molecule sequencing from those reaction regions. Sequence analysis can be performed after distribution of the nucleic acids to and their immobilization in the array regions.

In some aspects, the present invention includes methods of analyzing the sequence of template nucleic acids. In such aspects, the sequence analysis typically employs template dependent synthesis in identifying the nucleotide sequence of the template nucleic acid. Nucleic acid sequence analysis that employs template dependent synthesis identifies individual bases, or groups of bases, as they are added during a template mediated synthesis reaction, such as a primer extension reaction, where the identity of the base is required to be complementary to the template sequence to which the primer sequence is hybridized during synthesis. Other such processes include ligation driven processes, where oligo- or polynucleotides are complexed with an underlying template sequence, in order to identify the sequence of nucleotides in that sequence. Typically, such processes are enzymatically mediated using nucleic acid polymerases, such as DNA polymerases, RNA polymerases, reverse transcriptases, and the like, or other enzymes such as in the case of ligation driven processes, e.g., ligases.

Sequence analysis using template dependent synthesis can include a number of different processes. For example, in embodiments utilizing sequence by synthesis processes, individual nucleotides or nucleotide analogs are identified iteratively as they are added to the growing primer extension product.

For sequencing processes that rely upon monitoring of the incorporation of nucleotides into growing nascent strands being synthesized by the complex, the progress of the reaction through these steps can of significant importance. In particular, for certain "real-time" nucleotide incorporation monitoring processes, the detectability of the incorporation event is improved based upon the amount of time the nucleotide is incorporated into and retained within the synthesis complex during its ultimate incorporation into a primer extension product. By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al., Science 299:682-686, January 2003, and Eid, J. et al., Science, 323(5910), 133-138 (2009), the full disclosures of which are incorporated herein by reference in their entirety for all purposes.

In some aspects, the methods of the present invention include steps from any single molecule sequencing methods known in the art. See, e.g., Rigler, et al., DNA-Sequencing at the Single Molecule Level, Journal of Biotechnology, 86(3): 161 (2001); Goodwin, P. M., et al., Application of Single Molecule Detection to DNA Sequencing. Nucleosides & Nucleotides, 16(5-6): 543-550 (1997); Howorka, S., et al., Sequence-Specific Detection of Individual DNA Strands using Engineered Nanopores, Nature Biotechnology, 19(7): 636-639 (2001); Meller, A., et al., Rapid Nanopore Discrimination Between Single Polynucleotide Molecules, Proceedings of the National Academy of Sciences of the United States of America, 97(3): 1079-1084 (2000); Driscoll, R. J., et al., Atomic-Scale Imaging of DNA Using Scanning Tunneling Microscopy. Nature, 346(6281): 294-296 (1990).

In some embodiments, methods of single molecule sequencing known in the art include detecting individual nucleotides as they are incorporated into a primed template, i.e., sequencing by synthesis. Such methods often utilize exonucleases to sequentially release individual fluorescently labeled bases as a second step after DNA polymerase has formed a complete complementary strand. See Goodwin et al., "Application of Single Molecule Detection to DNA Sequencing," Nucleos. Nucleot. 16: 543-550 (1997).

In general, for sequencing methods utilizing compositions of the present invention, individual polymerase compositions are provided within separate discrete regions of a support. For example, in some cases, individual complexes may be provided within individual confinement structures, including nanoscale structures such as nanoscale wells. In further examples, zero mode waveguide cores or any of the reaction regions discussed herein serve as the reaction regions for sequencing methods utilizing compositions of the present invention. Examples of waveguides and processes for immobilizing individual complexes therein are described in, e.g., Published International Patent Application No. WO 2007/123763, the full disclosure of which is incorporated herein by reference in its entirety for all purposes and in particular for all teachings related to providing individual complexes into individual confinement structures. In some cases the nucleic acids (e.g., polymerase/template complexes) can be provided onto or proximal to structures or regions that allow for electronic single molecule sequencing. Such structures can include nanoscale electronic structures such as electrodes, capacitors, or field effect transducers (nanoFETs). NanoFETs include those having carbon nanotube gates. Such structures and their use for single molecule sequencing are described, for example, in U.S. Patent Application Publication No. 2015/0065353 which is incorporated herein in its entirety for all purposes and in particular for all teachings related to structures for use in single molecule sequencing.

Incorporation of labeled nucleotide analogs by polymerases is particularly useful in a variety of different nucleic acid analyses, including real-time monitoring of DNA polymerization. The label can itself be incorporated, or more preferably, can be released during incorporation of the analog. For example, analog incorporation can be monitored in real time by monitoring label release during incorporation of the analog by the polymerase. The portion of the analog that is incorporated can be the same as a natural nucleotide, or can include features of the analog that differ from a natural nucleotide.

In general, label incorporation or release can be used to indicate the presence and composition of a growing nucleic acid strand, e.g., providing evidence of template replication/amplification and/or sequence of the template. Signaling from the incorporation can be the result of detecting labeling groups that are liberated from the incorporated analog, e.g., in a solid phase assay, or can arise upon the incorporation reaction. For example, in the case of FRET labels where a bound label is quenched and a free label is not, release of a label group from the incorporated analog can give rise to a fluorescent signal. Alternatively, the enzyme may be labeled with one member of a FRET pair proximal to the active site, and incorporation of an analog bearing the other member will allow energy transfer upon incorporation. The use of enzyme bound FRET components in nucleic acid sequencing applications is described, e.g., in U.S. Patent Application Publication No. 2003/0044781, incorporated herein by reference.

In one example reaction of interest, a polymerase reaction can be isolated within an extremely small observation volume that effectively results in observation of individual polymerase molecules. As a result, the incorporation event provides observation of an incorporating nucleotide analog that is readily distinguishable from non-incorporated nucleotide analogs. In a preferred aspect, such small observation volumes are provided by immobilizing the polymerase enzyme within an optical confinement, such as a Zero Mode Waveguide (ZMW). For a description of ZMWs and their application in single molecule analyses, and particularly nucleic acid sequencing, see, e.g., U.S. Patent Application Publication No. 2003/0044781 and U.S. Pat. No. 6,917,726, each of which is incorporated herein by reference in its entirety for all purposes. See also Levene et al. (2003) "Zero-mode waveguides for single-molecule analysis at high concentrations" Science 299:682-686, Eid et al. (2009) "Real-time DNA sequencing from single polymerase molecules" Science 323:133-138, and U.S. Pat. Nos. 7,056,676, 7,056,661, 7,052,847, and 7,033,764, the full disclosures of which are incorporated herein by reference in their entirety for all purposes.

In general, a polymerase enzyme is complexed with the template strand in the presence of one or more nucleotides and/or one or more nucleotide analogs. For example, in certain embodiments, labeled analogs are present representing analogous compounds to each of the four natural nucleotides, A, T, G and C, e.g., in separate polymerase reactions, as in classical Sanger sequencing, or multiplexed together, e.g., in a single reaction, as in multiplexed sequencing approaches. When a particular base in the template strand is encountered by the polymerase during the polymerization reaction, it complexes with an available analog that is complementary to such nucleotide, and incorporates that analog into the nascent and growing nucleic acid strand. In one aspect, incorporation can result in a label being released, e.g., in polyphosphate analogs, cleaving between the α and β phosphorus atoms in the analog, and consequently releasing the labeling group (or a portion thereof). The incorporation event is detected, either by virtue of a longer presence of the analog and, thus, the label, in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a zero mode waveguide. For additional information on single molecule sequencing monitoring incorporation of phosphate-labeled analogs in real time, see, e.g., Eid et al. (2009) "Real-time DNA sequencing from single polymerase molecules" Science 323:133-138.

In a first exemplary technique, a nucleic acid synthesis complex, including a polymerase enzyme, a template sequence and a complementary primer sequence, is provided immobilized within an observation region that permits illumination and observation of a small volume that includes the complex without excessive illumination of the surrounding volume. By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume. In particular, when a nucleotide is incorporated into DNA by the polymerase, it is retained within the observation volume for a prolonged period of time, and upon continued illumination yields a prolonged fluorescent signal. By comparison, randomly diffusing and not incorporated nucleotides remain within the observation volume for much shorter periods of time, and thus produce only transient signals, many of which go undetected due to their extremely short duration.

In particularly preferred exemplary systems, the confined illumination volume is provided through the use of arrays of optically confined apertures termed zero mode waveguides (ZMWs). See, e.g., U.S. Pat. No. 6,917,726, which is incorporated herein by reference in its entirety for all purposes. For sequencing applications, the DNA polymerase is typically provided immobilized upon the bottom of the ZMW, although another component of the complex (e.g., a primer or template) is optionally immobilized on the bottom of the ZMW to localize the complex. See, e.g., Korlach et al. (2008) PNAS U.S.A. 105(4):1176-1181 and US patent application publication 2008-0032301, each of which is incorporated herein by reference in its entirety for all purposes.

In operation, the fluorescently labeled nucleotides (e.g., analogs corresponding to A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuse away from the complex following incorporation of the associated nucleotide, nor do such labels interfere with the incorporation event. See, e.g., Korlach et al. (2008) Nucleosides, Nucleotides and Nucleic Acids 27:1072-1083.

In a second exemplary technique, the immobilized complex and the nucleotides to be incorporated are each provided with interactive labeling components. Upon incorporation, the nucleotide borne labeling component is brought into sufficient proximity to the complex borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal quenching. Upon incorporation and cleavage of the terminal phosphate groups, e.g., bearing a donor fluorophore, the quenching is removed and the resulting characteristic fluorescent signal of the donor is observable.

In exploiting the foregoing processes, where the incorporation reaction occurs too rapidly, it may result in the incorporation event not being detected, i.e., the event speed exceeds the detection speed of the monitoring system. The missed detection of incorporated nucleotides can lead to an increased rate of errors in sequence determination, as omissions in the real sequence. In order to mitigate the potential for missed pulses due to short reaction or product release times, in one aspect, the current invention can result in increased reaction and/or product release times during incorporation cycles. Similarly, very short interpulse distances can occasionally cause pulse merging. An advantage of employing polymerases with reduced reaction rates, e.g., polymerases exhibiting decreased rates and/or two slow-step kinetics as described in US patent application publications 2009-0286245 and 2010-0112645, is an increased frequency of longer, detectable, binding events. This advantage may also be seen as an increased ratio of longer, detectable pulses to shorter, non-detectable pulses, where the pulses represent binding events.

The sequencing processes, e.g., using the substrates described above and the compositions of the invention, are generally exploited in the context of a fluorescence optical system that is capable of illuminating the various complexes on the substrate, and obtaining, detecting and separately recording fluorescent signals from these complexes. Such systems typically employ one or more illumination sources that provide excitation light of appropriate wavelength(s) for the labels being used. An optical train directs the excitation light at the reaction region(s) and collects emitted fluorescent signals and directs them to an appropriate detector or detectors. Additional components of the optical train can provide for separation of spectrally different signals, e.g., from different fluorescent labels, and direction of these separated signals to different portions of a single detector or to different detectors. Other components may provide for spatial filtering of optical signals, focusing and direction of the excitation and or emission light to and from the substrate. An exemplary system is also described in Lundquist et al., Published U.S. Patent Application No. 2007-0036511, Optics Letters, Vol. 33, Issue 9, pp. 1026-1028, the full disclosure of which is incorporated herein by reference in its entirety for all purposes.

Fluorescence reflective optical trains can be used in the applications of the systems of the invention. For a discussion on the advantages of such systems, see, e.g., U.S. patent application Ser. No. 11/704,689, filed Feb. 9, 2007, Ser. No. 11/483,413, filed Jul. 7, 2006, and Ser. No. 11/704,733, filed Feb. 9, 2007, the full disclosures of which are incorporated herein by reference in their entirety for all purposes.

In the context of the nucleic acid sequencing methods described herein, it will be appreciated that the signal sources each represent sequencing reactions, and particularly, polymerase mediated, template dependent primer extension reactions, where in preferred aspects, each base incorporation event results in a prolonged illumination (or localization) of one of four differentially labeled nucleotides being incorporated, so as to yield a recognizable pulse (peak) that carries a distinguishable spectral profile or color.

In other embodiments, methods and compositions of the present invention are utilized in sequencing methods utilizing nanopores. In exemplary embodiments, a single nucleic acid is loaded into each of a plurality of nanopores. In certain embodiments, the nucleic acids are attached proximal to the nanopore. As will be appreciated, helicases and/or exonucleases as well as polymerases can be used in nanopore sequencing. Complexes of these enzymes with nucleic acids can be loaded to nanopores as detailed herein, and the nucleic acid or enzyme component of the complex can be attached to or proximal to the nanopore. Methods of nanopore sequencing are known in the art and disclosed for example in US Published App. Nos. 2013/0327644 and 2014/0051068, which are hereby incorporated by reference for all purposes and in particular for all teachings, written description, figures and figure legends related to nanopore sequencing.

The methods described herein can further include computer implemented processes, and/or software incorporated onto a computer readable medium instructing such processes, as set forth in greater detail below. As such, signal data generated by the reactions and optical systems described above, is input or otherwise received into a computer or other data processor, and subjected to one or more of the various process steps or components set forth below. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or Macintosh® type computers running Intel quadcore processors, to workstations, laboratory equipment, or high speed servers, running UNIX, LINUX, Windows®, or other systems. Logic processing of the invention may be performed entirely by general purposes logic processors (such as CPUs) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

In some cases, the compositions, methods, and systems of the invention can be used as part of an integrated sequencing system, for example, as described in US 20120014837 Illumination of Integrated Analytical Systems, US 20120021525 Optics Collection and Detection System and Method, US 20120019828 Integrated Analytical System and Method, 61/660,776 filed Jun. 17, 2012 Arrays of Integrated Analytical Devices and Methods for Production, US 20130338010, and US 20120085894 Substrates and Optical Systems and Methods of Use Thereof, which are incorporated herein by reference in their entirety for all purposes.

In certain embodiments, the sequencing compositions described herein will be provided in whole, or in part, in kit form enabling one to carry out the processes described herein. Such kits will typically comprise one or more components of the reaction complex, such as the polymerase enzyme and primer sequences. Such kits will also typically include a biotin-binding protein, buffers, and reagents for loading of the polymerase and/or a template as in the processes described herein. The kits will also optionally include other components for carrying out sequencing applications in accordance with those methods described herein. In particular, such kits may include ZMW array substrates for use in observing individual reaction complexes as described herein.

In further exemplary embodiments, kits of the present disclosure include (alone, or in any combination with the above described components of kits) components for use in the loading methods described herein. Such components may include in any combination one or more of the following: at least one biotin-binding protein as described herein, a nucleic acid condensing agent (e.g., in a prepared solution), standard buffer for covering the surface, polymerase enzymes, nucleic acid templates, primer sequences, magnetic beads or other particles for loading the nucleic acids, and any other composition described herein associated with loading polymerase compositions to a surface and/or conducting a sequencing reaction. The kits will typically include instructions for carrying out the desired processes, as also described or referenced herein, e.g., for immobilizing nucleic acids and/or performing sequence by incorporation reactions.

Substrates and Surfaces

Substrates of use in methods of the invention are known in the art and discussed herein, and as will be appreciated, any of the substrates discussed herein can be used in any combination for any embodiments discussed herein.

In exemplary embodiments, methods of the invention utilize substrates that include one or more reaction regions (also referred to herein as "array regions") arranged in the form of an array on an inert substrate material, also referred to herein as a "solid support" or "surface", that allows for combination of reactants (e.g., in a sequencing reaction, binding reaction, etc.) in a defined space. Arrays can be regular or irregular, e.g., random. The substrates and array regions can also allow for detection, e.g., of the sequencing reaction event. As described above, nucleic acids or polymerase complexes can be deposited in the reaction regions such that individual nucleic acids (or polymerase reactions) are independently optically observable. A reaction region can be a localized area on the substrate material that facilitates interaction of reactants, e.g., in a nucleic acid sequencing reaction. A reaction region may in certain embodiments be a nanoscale well (also referred to herein as a nanowell), and in further embodiments the nanowell is a ZMW. A nanoscale well typically has dimensions in the nanometer range, i.e., less than 1 micrometer. In some embodiments, a nanoscale well has a cross-sectional diameter of less than 1000, 900, 800, 700, 600, or 500 nm, e.g., less than 400, 350, 300, 250, or 200 nm. In some embodiments, a nanoscale well has a depth of less than 1000, 900, 800, 700, 600, or 500 nm, e.g., less than 400, 350, 300, 250, or 200 nm. As discussed herein, the sequencing reactions contemplated by the invention can in some embodiments occur on numerous individual nucleic acid samples in tandem, in particular simultaneously sequencing numerous nucleic acid samples, e.g., derived from genomic and chromosomal DNA. The apparatus of the invention can therefore include an array having a sufficient number of array regions/reaction regions to carry out such numerous individual sequencing reactions. In one embodiment, the array comprises at least 1,000 reaction regions. In another embodiment, the array comprises greater than 400,000 reaction regions, preferably between 400,000 and 20,000,000 reaction regions. In a more preferred embodiment, the array comprises between 1,000,000 and 16,000,000 reaction regions, e.g., 1,000,000, 2,000,000, 3,000,000, 4,000,000, 5,000,000, 6,000,000, 7,000,000, 8,000,000, 9,000,000, or 10,000,000 reaction regions.

The reaction regions on the array may take the form of a cavity or well in the substrate material, having a width and depth, into which reactants can be deposited. One or more of the reactants typically are bound to the substrate material in the reaction region and the remainder of the reactants are in a medium which facilitates the reaction and which flows through or contacts the reaction region. When formed as cavities or wells, the chambers are preferably of sufficient dimension and order to allow for (i) the introduction of the necessary reactants into the chambers, (ii) reactions to take place within the chamber and (iii) inhibition of mixing of reactants between chambers. The shape of the well or cavity is preferably circular or cylindrical, but can be multisided so as to approximate a circular or cylindrical shape. In another embodiment, the shape of the well or cavity is substantially hexagonal. The cavity can have a smooth wall surface. In an additional embodiment, the cavity can have at least one irregular wall surface. The cavities can have, e.g., a planar bottom or a concave bottom.

The reaction regions may in some situations take the form of a nanopore. Such reaction regions, including arrays of nanopores, are known in the art and described for example in US Published App. Nos. 2013/0327644 and 2014/0051068, which are hereby incorporated by reference in their entirety for all purposes and in particular for all teachings related to nanopore arrays.

Any material can be used as the solid support material, as long as the surface allows for stable attachment of nucleic acids or polymerase enzyme complexes and optionally detection of nucleotide incorporation. The solid support material can be planar or can be cavitated, e.g., in a cavitated terminus of a fiber optic or in a microwell etched, molded, or otherwise micromachined into the planar surface, e.g. using techniques commonly used in the construction of microelectromechanical systems. See e.g., Rai-Choudhury, HANDBOOK OF MICROLITHOGRAPHY, MICROMACHINING, AND MICROFABRICATION, VOLUME 1: MICROLITHOGRAPHY, Volume PM39, SPIE Press (1997); Madou, CRC Press (1997), Aoki, Biotech. Histochem. 67: 98-9 (1992); Kane et al., Biomaterials. 20: 2363-76 (1999); Deng et al., Anal. Chem. 72:3176-80 (2000); Zhu et al., Nat. Genet. 26:283-9 (2000). In some embodiments, the solid support is optically transparent, e.g., glass.

Suitable substrates include chips having arrays of nanoscale wells or zero mode waveguides. Exemplary substrates include substrates having a metal or metal oxide layer on a silica-based layer, with nanoscale wells disposed through the metal or metal oxide layer to or into the silica-based layer. Such substrates are described, for example in U.S. patent application Ser. Nos. 10/259,268, 14/187,198, 14/107,730, 13/920,037, and U.S. Pat. Nos. 8,994,946, 8,906,670, 8,993,307, 8,802,600, 7,907,800, and 7,302,146, which are incorporated herein by reference in their entirety for all purposes and in particular for all teachings related to substrates. Biotinylation of such substrates (e.g., of the base of the wells) is described, e.g., in U.S. Pat. Nos. 7,763,423 and 8,802,600 and U.S. patent application publication 2017-0184580 (which are incorporated herein by reference in their entirety for all purposes), as is loading and immobilization of nucleic acids, polymerases, and other molecules on such substrates.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1: SG1 Modification of Streptavidin

Streptavidin (e.g., wild type or mutant) is modified with SG1 as shown in FIG. 1A. An ice-chilled solution of SG1-NHS in dimethylacetamide (100 mM, 75-100 eq.) is added to an ice-chilled solution of streptavidin (0.5-1 mM, 1 eq.) in 0.2 M sodium bicarbonate, targeting the final organic/aqueous ratio of ~0.5. The mixture is kept at 0° C. for 3-7 days. The product is purified by anion exchange chromatography using 5-20 mL GE Q Sepharose HP column. The fractions containing the desired SG1-modified streptavidin are concentrated using membrane filtration.

Example 2: Succinylation of Streptavidin

Streptavidin is succinylated as shown in FIG. 2. An ice-chilled solution of succinic anhydride in dimethylacetamide (200 mM, 100 eq.) is added to an ice-chilled solution of streptavidin (1.4 mM, 1 eq.) in 0.2 M sodium bicarbonate, targeting the final organic/aqueous ratio of ~0.7. The mixture is kept overnight at 0° C. The product is purified by anion exchange chromatography using 5 mL GE Q Sepharose HP column. The fractions containing the desired succinylated streptavidin are concentrated using membrane filtration.

Example 3: Two Step Click Modification of Streptavidin

As shown in FIG. 3, SGC-modified streptavidin is prepared using the procedure described in Example 1 but starting from streptavidin and SGC-NHS instead of SG1-NHS. The azido groups of the resulting SGC-modified streptavidin (0.6 mM, 1 eq.) are further reacted with SG1-BCN (73.5 eq.) at room temperature overnight. The product is purified by anion exchange chromatography using 5 mL GE Q Sepharose HP column. The fractions containing the desired SG1-clicked SGC-streptavidin are concentrated using membrane filtration.

Example 4: Immobilization of Polymerase/Nucleic Acid Complexes with Modified Streptavidins for Single Molecule Sequencing The following sets forth a series of experiments that demonstrate that immobilization of polymerase-nucleic acid complexes using modified and/or mutated streptavidins can confer advantages in single molecule sequencing, including increased readlength. Without limitation to any particular mechanism, it is thought that use of modified and/or mutated streptavidins improves survival of the surface-associated polymerase.

Formulation of Polymerase with Streptavidin

Mutant Φ29 polymerases containing two biotin-tag sequences are cloned and purified (e.g., basically as described in U.S. Pat. No. 9,399,766). Aliquots of the polymerases are formulated with streptavidin at a 1:10 polymerase:tetrameric streptavidin molar ratio. (A large excess of streptavidin is used to prevent 2 polymerase:1 streptavidin tetramer complexes from forming.) The final salt concentration at this step is ~150 mM NaCl to allow downstream purification through the binding of polymerase to heparin columns. For example, streptavidin-formulated polymerase can be high-throughput purified via heparin-packed tips using a Biomek robotic platform to remove the excess streptavidin (operating under the principle that polymerase will bind heparin under low salt, and can be eluted with 1M NaCl). Glycerol is added to 55% to allow long term storage at −20° C. The streptavidin-formulated samples are run on a denaturing gel and compared to a known concentration standard for quantification and quality control. The formulated polymerases are then incubated with appropriate nucleic acid primer/templates and used with commercially available reagents for sequencing on either the RSII or Sequel™ systems from Pacific Biosciences of California, following protocols described in the commercial literature.

Performance of Polymerases Formulated with SG1-Modified Streptavidin

Performance of mutant Φ29 polymerases immobilized via either streptavidin or SG1-modified streptavidin is assessed in single molecule sequencing reactions.

Table 3 presents data from an 8 hour movie on a single Sequel™ chip with a polymerase formulated with either unmodified streptavidin (SA) or SG1-modified streptavidin. The polymerase formulations are multiplexed on identifiably different templates with similar characteristics (i.e., length and base composition). The SG1-modified formulations demonstrate a readlength advantage.

TABLE 3

| Polymerase + | Readlength median # bases | Template number |
| --- | --- | --- |
| SA | 35688 | 1 |
| SA | 37642 | 2 |
| SA (SG1) | 50940 | 3 |
| SA (SG1) | 48782 | 4 |
| SA (SG1) | 54297 | 5 |

Table 4 presents data for three different Φ29 mutant polymerases (polymerases 1-3), each formulated with either unmodified streptavidin (SA) or different samples of SG1-modified streptavidin. Data is from an 8 hour movie on a single Sequel™ chip. The polymerase formulations are multiplexed on identifiably different templates with similar characteristics (i.e., length and base composition). The SG1-modified formulations again demonstrate a readlength advantage.

TABLE 4

| Polymerase variant | Streptavidin | Readlength (median) | Readlength (ratio)* |
| --- | --- | --- | --- |
| Pol 1 | Unmodified | 18812 | 0.98 |
| Pol 1 | Unmodified | 15727 | 0.82 |
| Pol 1* | Unmodified | 19120 | 1 |
| Pol 1 | Unmodified | 18669 | 0.98 |
| Pol 1 | SA (SG1) sample 2 | 29808 | 1.56 |
| Pol 1 | SA (SG1) sample 3 | 28319 | 1.48 |
| Pol 1 | SA (SG1) sample 4 | 22712 | 1.19 |
| Pol 1 | SA (SG1) sample 5 | 29608 | 1.55 |
| Pol 2 | Unmodified | 21089 | 1.17 |
| Pol 2 | Unmodified | 18127 | 1.01 |
| Pol 2* | Unmodified | 17970 | 1 |
| Pol 2 | Unmodified | 16220 | .9 |
| Pol 2 | SA (SG1) sample 1 | 28131 | 1.57 |
| Pol 2 | SA (SG1) sample 2 | 27695 | 1.54 |
| Pol 2 | SA (SG1) sample 3 | 24280 | 1.35 |
| Pol 2 | SA (SG1) sample 4 | 29150 | 1.62 |
| Pol 2 | SA (SG1) sample 5 | 27235 | 1.52 |
| Pol 3 | Unmodified | 23399 | 1.03 |
| Pol 3 | Unmodified | 23181 | 1.02 |
| Pol 3* | Unmodified | 22638 | 1 |
| Pol 3 | Unmodified | 22953 | 1.01 |
| Pol 3 | Unmodified | 22908 | 1.01 |
| Pol 3 | SA (SG1) sample 1 | 39906 | 1.76 |
| Pol 3 | SA (SG1) sample 2 | 38003 | 1.68 |
| Pol 3 | SA (SG1) sample 4 | 35283 | 1.56 |
| Pol 3 | SA (SG1) sample 5 | 37591 | 1.66 |

*Ratio calculated for each different polymerase variant, relative to the indicated sample Charge on Streptavidin Correlates with Readlength Performance of a mutant Φ29 polymerase immobilized via streptavidins having different net charges is assessed in single molecule sequencing.

Table 5 presents data from an 8 hour movie on a single Sequel™ chip with a polymerase formulated with either unmodified streptavidin (SA), succinylated streptavidin, SGC-modified streptavidin, or SG1-modified streptavidin. The streptavidins comprise the wild type sequence of SEQ ID NO:1 (SA), a lysine to arginine mutation of the lysine near the biotin binding site (SA-K108R), lysine to arginine mutations of all four lysines (K67R, K108R, K119R, and K121R; SA-4KtoR), or a polyglutamate tail (SA-10E). The polymerase formulations are multiplexed on identifiably different templates with similar characteristics (i.e., length and base composition). Benefits from placing additional negative charge on streptavidin are apparent.

TABLE 5

| Streptavidin variant (modification) | Retention time on anion exchange column (min) | Readlength (median) |
| --- | --- | --- |
| SA-K108R | 2.75 | 36220 |
| SA | 2.76 | 35688 |
| SA (Succinylated) | 6.82 | 40498 |
| SA-10E | 7.56 | 38625 |
| SA-4KtoR (SG1) | 8.32 | 29970 |
| SA (SGC) | 9.2 | 47871 |
| SA-K108R (SG1) | 11.2 | 42628 |
| SA (SG1) | 11.93 | 49907 |
| SA-10E (SG1) | 11.93 | 49842 |

Example 5: SG1 Modification of Avidin and Neutravidin and Immobilization of Polymerase/Nucleic Acid Complexes for Single Molecule Sequencing Avidin (ThermoFisher Scientific) and neutravidin (EMD) are modified with SG1. An ice-chilled solution of avidin or neutravidin (0.5-1 mM, 1 eq.) in 0.5 M sodium bicarbonate is added to an ice-chilled solid SG1-NHS (100 eq.). The mixture is kept at 0° C. for 3-7 days. The product is purified by anion exchange chromatography. The fractions containing the desired SG1-modified avidin or neutravidin are concentrated using membrane filtration.

SG1-modified avidin, neutravidin, and streptavidin are formulated with a mutant Φ29 polymerase basically as described above, as are unmodified avidin, neutravidin, and streptavidin. The formulated polymerases are then incubated with appropriate nucleic acid primer/templates and used with commercially available reagents for sequencing on a Sequel™ system from Pacific Biosciences of California, following protocols described in the commercial literature.

Table 6 presents data from an 8 hour movie on a single Sequel™ chip with a polymerase formulated with unmodified streptavidin, avidin, or neutravidin or with SG1-modified streptavidin, avidin, or neutravidin. The polymerase formulations are multiplexed on identifiably different templates with similar characteristics (i.e., length and base composition). Avidin and SG1-modified avidin display loading deficiencies compared to modified and unmodified streptavidin and neutravidin. The SG1-modified formulations of avidin, neutravidin, and streptavidin demonstrate rate and readlength advantages over the corresponding unmodified formulations.

TABLE 6

| Biotin-binding protein | nReads | Readlength (median) | Pol rate | Accuracy (median) |
|---|---|---|---|---|
| Streptavidin | 9849 | 33804 | 2.14 | 87.1% |
| SG1-Streptavidin | 26860 | 55344 | 2.37 | 87.3% |
| Avidin | 94 | 40237 | 1.97 | 86.2% |
| SG1-Avidin | 1239 | 50572 | 2.32 | 87.2% |
| Neutravidin | 37690 | 44374 | 2.00 | 87.3% |
| SG1-Neutravidin | 9937 | 51242 | 2.41 | 87.4% |

Example 6: Modification of Streptavidin with PEGs and Sulfonated PEGs and Immobilization of Polymerase/Nucleic Acid Complexes for Single Molecule Sequencing Streptavidin is modified with mPEG9, SGC-PEGS-OH, propargyl-PEG8, PEGS-PEGS-SG1, azido-PEGS, and PEG8-BCN-SG1 as schematically illustrated in FIGS. 5-8. mPEG9-NHS, propargyl-PEGS-OH, propargyl-PEG8-NHS, and azido-PEG8-NHS are purchased from BroadPharm (San Diego, Calif.).

As schematically illustrated in FIGS. 5, 7, and 8, the corresponding PEG-NHS ester (200 eq.) is added to an ice-chilled solution of streptavidin (1-2 mM, 1 eq.) in 0.5 M sodium bicarbonate. The mixture is kept at 0° C. for 3-7 days. The pegylated streptavidin product is separated from the reagents using membrane filtration.

The azido group in SGC-modified streptavidin is reacted with propargyl-PEG9-alcohol under Cu(I) catalyzed "click" reaction as schematically illustrated in FIG. 6. Propargyl-PEG9-alcohol (300 eq.) is added to a solution of SGC-modified streptavidin (0.6 mM, 1 eq.) in the formulation buffer (20 mM Tris HCl, pH 7.5, 100 mM KOAc) followed by the Cu(I) solution prepared from aqueous solutions of copper(II) sulfate (100 mM, 2 eq.), TPTA ligand (tris((1-PEG3-1,2,3-triazol-4-yl)methyl)amine, 200 mM, 6 eq.), and sodium ascorbate (1 M, 10 eq.). The mixture is kept at room temperature for 10 hours. The streptavidin-(SGC-PEGS-OH)$_n$ product is separated from the reagents using membrane filtration.

The propargyl group in propargyl-PEGS-modified streptavidin is reacted with SG1-PEG8-azide as schematically illustrated in FIG. 7. SG1-PEG8-azide (257 eq.) is added to a solution of propargyl-PEGS-modified streptavidin (0.95 mM, 1 eq.) in the formulation buffer (20 mM Tris HCl, pH 7.5, 100 mM KOAc) followed by the Cu(I) solution prepared from aqueous solutions of copper(II) sulfate (100 mM, 2 eq.), TPTA ligand (200 mM, 6 eq.), and sodium ascorbate (1 M, 10 eq.). The mixture is kept at room temperature for 10 hours. The streptavidin-(PEGS-PEGS-SG1)$_n$ product is purified by anion exchange chromatography. The fractions containing the product are concentrated using membrane filtration.

The azido group in azido-PEGS-modified streptavidin is reacted with SG1-BCN as schematically illustrated in FIG. 8. SG1-BCN (109 eq.) is added to a solution of azido-PEGS-modified streptavidin (0.97 mM, 1 eq.) in the formulation buffer (20 mM Tris HCl, pH 7.5, 100 mM KOAc). The mixture is kept at room temperature for 24 h. The streptavidin-(PEGS-BCN-SG1)$_n$ product is purified by anion exchange chromatography. The fractions containing the product are concentrated using membrane filtration.

Modified streptavidins are formulated with a mutant Φ29 polymerase basically as described above. The formulated polymerases are then incubated with appropriate nucleic acid primer/templates and used with commercially available reagents for sequencing on a Sequel™ system from Pacific Biosciences of California, following protocols described in the commercial literature.

Table 7 presents data from an 8 hour movie on a single Sequel™ chip. The polymerase formulations are multiplexed on identifiably different templates with similar characteristics (i.e., length and base composition).

TABLE 7

| Modification on streptavidin | nReads | Readlength (median) | Pol rate | Accuracy (median) |
|---|---|---|---|---|
| none | 9849 | 33804 | 2.14 | 87.1% |
| SG1 | 26860 | 55344 | 2.37 | 87.3% |
| mPEG9 | 32147 | 35718 | 2.27 | 87.1% |
| PEG8-propargyl | 28632 | 49101 | 2.24 | 87.3% |
| PEG8-N3 | 28933 | 43110 | 2.38 | 87.2% |
| SGC-PEG9-OH | 16603 | 58619 | 2.27 | 87.3% | mPEG9-modified streptavidin performs similarly to unmodified streptavidin. Azido- and propargyl-modified streptavidins display increased readlengths. SGC-PEG9-OH-modified streptavidin performs similarly to SG1-modified streptavidin. In a subsequent sequencing run, PEGS-BCN-SG1-modified streptavidin and PEGS-PEGS-SG1-modified streptavidin also perform similarly to SG1-modified streptavidin. In general, addition of a PEG moiety appears to have little impact on sequencing performance, since modification with a group containing both a charged moiety and PEG is similar to modification with a group containing the charged moiety without PEG.

Example 7: Synthesis of SG1-SGA-NHS Ester

Synthesis and NHS ester activation of SG1-SGA is schematically illustrated in FIG. 10A. In step 1, to a DMA solution of 4-(2-aminoethoxy)-3,5-bis(3-sulfopropoxy)benzoic acid (SGA) is added a solution of SG1-NHS (100 mM, 1 eq) in DMA, followed by aqueous NaHCO$_3$ (0.4 N), targeting a final organic/aqueous ration of ~0.5. The mixture is kept at room temperature overnight. The product is purified by preparative HPLC using Waters C18 reverse phase 19×100 column to give a colorless gum.

In step 2, to a DMA solution of SG1-SGA-COOH (30 mM) is added CDI (4 eq). After stirring at room temperature for 1 hour, NHS (6 eq) is added. The reaction mixture is stirred at room temperature overnight. Ethyl acetate is added to precipitate the product, which is isolated by centrifugation and dried under high vacuum.

Streptavidin is modified with SG1-SGA-NHS, modified streptavidin is formulated with a mutant Φ29 polymerase, and single molecule sequencing is performed basically as described above.

Example 8: Synthesis of 3,5-Disulfobenzoic Acid NHS Ester

Figure 9A:
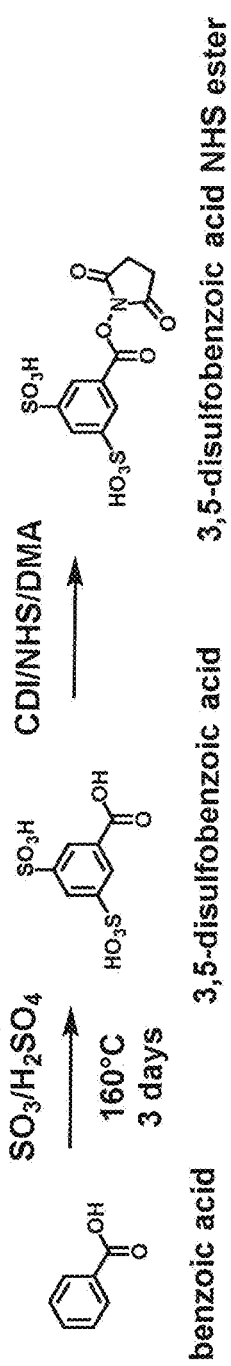
FIG. 9A schematically illustrates synthesis of an N-hydroxysuccinimide ester of 3,5-disulfobenzoic acid.
Figure 9B:
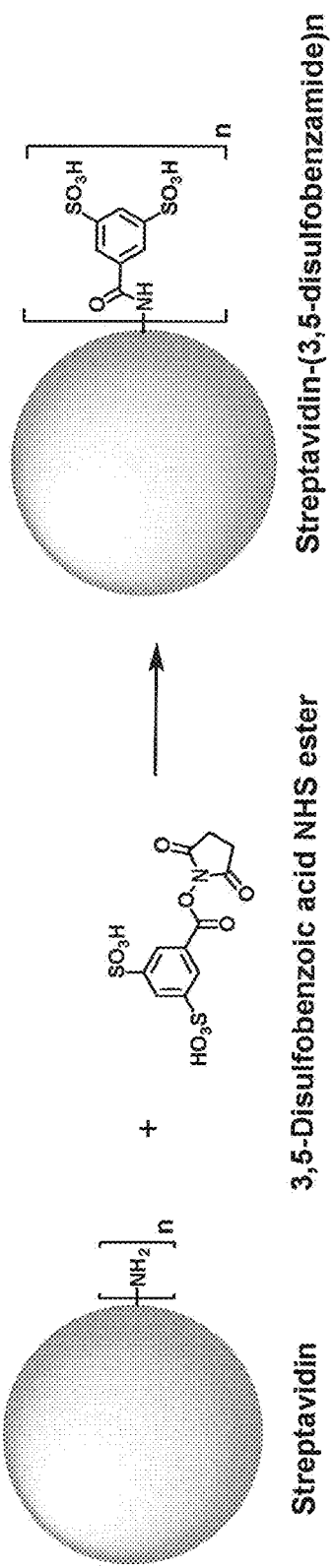
FIG. 9B schematically illustrates reaction of a free primary amino group in streptavidin with an N-hydroxysuccinimide ester of 3,5-disulfobenzoic acid.

Synthesis of 3,5-disulfobenzoic acid NHS ester is schematically illustrated in FIG. 9A. A solution of benzoic acid in fuming sulfuric acid (conc. ~2.0 M) is heated at 160° C. for 3 days. The resulting mixture is slowly added into a cold NaOH aqueous solution. The product is first purified by anion exchange chromatography using a 5-20 mL GE Q Sepharose HP column, then by reverse phase preparative HPLC using a Waters C18 reverse phase 30×100 column. The product is obtained as a white solid (3TEA salt). $^1$H NMR (D20): δ 8.41 (s, 2H), 8.30 (s, 1H), 8.20 (q, 18H), 1.28 (t, 30H). NHS ester activation is performed basically as described above.

Streptavidin is modified with the 3,5-disulfobenzoic acid NHS ester, modified streptavidin is formulated with a mutant Φ29 polymerase, and single molecule sequencing is performed basically as described above.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A composition comprising a modified biotin-binding protein that comprises one or more covalently attached sulfonate moieties.

2. The composition of claim 1, wherein the biotin-binding protein is a tetravalent biotin-binding protein.

3. The composition of claim 1, wherein the biotin-binding protein is streptavidin.

4. The composition of claim 1, wherein the biotin-binding protein comprises three or more covalently attached sulfonate moieties.

5. The composition of claim 1, wherein the biotin-binding protein comprises 12 or more covalently attached sulfonate moieties.

6. The composition of claim 1, wherein the biotin-binding protein comprises 45 or more covalently attached sulfonate moieties.

7. The composition of claim 1, wherein the biotin-binding protein comprises one or more covalently attached 3,4,5-tris(3-sulfopropoxy)benzoyl moieties.

8. The composition of claim 1, wherein the biotin-binding protein comprises 15 or more covalently attached 3,4,5-tris(3-sulfopropoxy)benzoyl moieties.

9. The composition of claim 1, wherein the biotin-binding protein is a tetravalent biotin-binding protein comprising 45 or more covalently attached sulfonate moieties.

10. The composition of claim 9, wherein the biotin-binding protein is streptavidin.

11. The composition of claim 1, wherein the biotin-binding protein is a tetravalent biotin-binding protein comprising 15 or more covalently attached 3,4,5-tris(3-sulfopropoxy)benzoyl moieties.

12. The composition of claim 11, wherein the biotin-binding protein is streptavidin.

13. The composition of claim 1, wherein the biotin-binding protein comprises one or more covalently attached 3,5-disulfobenzoyl or 2-sulfobenzoyl moieties.

14. The composition of claim 1, wherein the biotin-binding protein comprises one or more covalently attached polyethylene glycol (PEG) moieties.

15. The composition of claim 1, wherein the biotin-binding protein comprises one or more amino acid substitutions that decrease its calculated net charge relative to a parental biotin-binding protein.

16. The composition of claim 1, wherein the biotin-binding protein is bound to a nucleic acid polymerase.

17. The composition of claim 16, wherein the nucleic acid polymerase is complexed with a nucleic acid.

18. The composition of claim 1, wherein the biotin-binding protein is immobilized on a solid support.

19. The composition of claim 1, wherein the biotin-binding protein is immobilized on the base of a nanoscale well.

20. The composition of claim 1, wherein the composition is present in a nucleic acid sequencing system.

21. A system for sequencing nucleic acids, the system comprising
 a chip comprising a plurality of polymerase enzyme complexes bound thereto, each polymerase enzyme complex individually optically resolvable, each polymerase enzyme complex comprising a polymerase enzyme, a template nucleic acid, and optionally a primer hybridized to the template nucleic acid, wherein the polymerase enzyme complexes are bound to the chip through a modified biotin-binding protein that comprises one or more covalently attached sulfonate moieties;
 sequencing reagents in contact with the surface comprising reagents for carrying out nucleic acid synthesis including one or more labeled nucleotide analogs;
 an illumination system for illuminating the polymerase enzyme complexes;
 an optical detection system for detecting fluorescence from the labeled nucleotide analogs while they are interacting with the polymerase enzyme complexes; and
 a computer for analyzing the signals detected by the detection system to determine the sequential addition of nucleotides to a nucleic acid strand complementary to a strand of the template nucleic acid.

22. The composition of claim 1, wherein the biotin-binding protein is a tetrameric biotin-binding protein.

23. The composition of claim 1, wherein the biotin-binding protein is traptavidin.

* * * * *